US012790310B2

(12) United States Patent
Knopff et al.

(10) Patent No.: US 12,790,310 B2
(45) Date of Patent: Nov. 10, 2026

(54) PROCESS FOR PREPARING 3-(CYCLOHEX-1-EN-1-YL)PROPANAL DERIVATIVES

(71) Applicant: Firmenich SA, Satigny (CH)

(72) Inventors: Oliver Knopff, Satigny (CH); Philippe Dupau, Satigny (CH); Jean-Jacques Riedhauser, Satigny (CH); Nicolas Poirier, Satigny (CH); Dilver Peña FUENTES, Rostock (DE); Armin Börner, Rostock (DE); Luigi Marinoni, Satigny (CH)

(73) Assignee: Firmenich SA, Satigny (CH)

( * ) Notice: Subject to any disclaimer, the term of this patent is extended or adjusted under 35 U.S.C. 154(b) by 627 days.

(21) Appl. No.: 18/246,179

(22) PCT Filed: Aug. 30, 2021

(86) PCT No.: PCT/EP2021/073905
§ 371 (c)(1),
(2) Date: Mar. 21, 2023

(87) PCT Pub. No.: WO2022/049036
PCT Pub. Date: Mar. 10, 2022

(65) Prior Publication Data

US 2023/0365523 A1 Nov. 16, 2023

(30) Foreign Application Priority Data

Sep. 1, 2020 (EP) .................................... 20193779

(51) Int. Cl.

| | |
|---|---|
| ***C07C 45/59*** | (2006.01) |
| ***B01J 31/20*** | (2006.01) |
| ***B01J 31/22*** | (2006.01) |
| ***B01J 31/24*** | (2006.01) |
| ***C07C 45/65*** | (2006.01) |
| ***C07C 47/42*** | (2006.01) |
| ***C07C 67/283*** | (2006.01) |
| ***C07C 67/293*** | (2006.01) |
| ***C07C 69/75*** | (2006.01) |
| ***C07D 317/12*** | (2006.01) |

(52) U.S. Cl.
CPC ............ *C07D 317/12* (2013.01); *B01J 31/20* (2013.01); *B01J 31/2234* (2013.01); *B01J 31/2457* (2013.01); *C07C 45/59* (2013.01); *C07C 45/65* (2013.01); *C07C 47/42* (2013.01); *C07C 67/283* (2013.01); *C07C 67/293* (2013.01); *C07C 69/75* (2013.01); *B01J 2231/321* (2013.01); *B01J 2531/004* (2013.01); *B01J 2531/822* (2013.01); *C07C 2601/16* (2017.05)

(58) Field of Classification Search
USPC .......................................................... 560/232
See application file for complete search history.

(56) References Cited

U.S. PATENT DOCUMENTS

| | | | |
|---|---|---|---|
| 4,085,272 | A | 4/1978 | Weiss |
| 4,327,749 | A | 5/1982 | Schreck et al. |
| 2013/0090390 | A1 | 4/2013 | Singer |

FOREIGN PATENT DOCUMENTS

| | | |
|---|---|---|
| EP | 1 054 053 | 11/2000 |
| EP | 1 529 770 | 5/2005 |
| GB | 803203 | 10/1958 |
| JP | 47-010371 | 5/1977 |
| JP | 62-012726 | 1/1987 |
| JP | 06-040954 | 2/1994 |
| WO | WO 2009/126584 | 10/2009 |
| WO | WO 2014/056851 | 4/2014 |
| WO | WO 2017/046071 | 3/2017 |
| WO | WO 2018/167200 | 9/2018 |
| WO | WO 2019/015974 | 1/2019 |
| WO | WO 2019/185599 | 10/2019 |

OTHER PUBLICATIONS

Brummond et al., Nov. 6, 2009, Rh(I)-Catalyzed Cyclocarbonylation of Allenol Esters To Prepare Acetoxy 4-Alkylidenecyclopent-3-en-2-ones, The Journal of Organic Chemistry, 74(21):8314-8320.

Dunne et al., 1970, Complexes of terpenes with transition metals. Part III. Dimerisation by means of tetrakis(triphenylphosphine)palladium, Journal of the Chemical Society, Section C: Organic Chemistry, pp. 2203-2206.

Ehlinger et al., 1980, Silicon in Synthesis. 10. The (Trimethylsilyl)allyl Anion: A β-Acyl Anion Equivalent for the Conversion of Aldehydes and Ketones into .gamma.-Lactones, Journal of the American Chemical Society, 102(15):5004-5011.

(Continued)

*Primary Examiner* — Ana Z Muresan

(74) *Attorney, Agent, or Firm* — Knobbe, Martens, Olson & Bear, LLP

(57) ABSTRACT

The present invention relates to the field of perfumery. More particularly, it concerns valuable new chemical intermediates for producing perfuming ingredients. Moreover, the present invention comprises also a process for producing compound of formula (I).

(I)

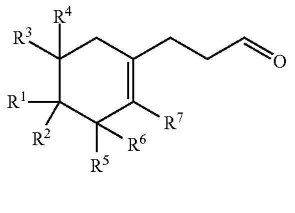

14 Claims, No Drawings

(56) References Cited

OTHER PUBLICATIONS

Gillespie et al., 1955, A Synthesis of (±)-Phellandral, Journal Of The Chemical Society, pp. 665-669.
Hayashi et al., 1991, Catalytic Asymmetric Elimination Forming Chiral 1,3-Dienes via π-Allylpalladium Intermediate, Tetrahedron Asymmetry, 2(3):195-198.
Hennion et al., 1956, The Controlled Semi-Hydrogenation of tert-Ethynyl Carbinols and Their Acetate Esters, The Journal of Organic Chemistry, 21(10):1142-1144.
Holemann et al., 2004, Synthesis of New Furan Derivatives and 4-Hydroxy Aldehydes from 4-Hydroxy 1-Enol Ethers, Synthesis, 2004(12):1963-1970.
Horiuchi et al., 1996, Asymmetric hydroformylation of conjugated dienes catalysed by [(R)-2-diphenylphosphino-1, 1'-dinaphthalen-2'-yl] [(S)-1,1'-dinap hthalene-2,2'-diyl]phosphite-rhodium( I), Chemical Communications, 2:155-156.
Horiuchi et al., 1997, Asymmetric Hydroformylation of Conjugated Dienes Catalyzed by Chiral Phosphine-Phosphite-Rh(I) Complex, Tetrahedron, 53(23):7795-7804.
Kim et al., 1992, Mercurinium ion mediated ring expansion of 1-alkenyl-1-cycloalkanols, Tetrahedron Letters, 33(30):4325-4328.
Li et al., 2012, Asymmetric Syntheses of 8-Oxabicyclo[3,2,1 ]octanes: A Cationic Cascade Cyclization, Angewandte Chemie International Edition, 51(32):8041-8045.
Nazarov et al., Aug. 1958, The Simplest Analogs of Corticosteroids. III. The introduction of Dihydroxyacetone, Glycerol and Dihydroxypropanecarboxylic Acid Side Chains into Derivatives of Cis- and Trans-Decalins, Journal of General Chemistry Ussr, 28(8):2227-2236.
Nazarov et al., Jul. 1958, The Simplest Analogs of Corticosteroids, Journal of General Chemistry USSR, 28(7):1838-1849.
Nozaki et al., 1997, Highly enantioselective hydroformylation of olefins catalyzed by Rhodium(I) complexes of new chiral phosphine-phosphite ligands, Journal of the American Chemical Society, 119(19):4413-4423.
Ojima et al., 2000, The Hydroformylation Reaction, Organic Reactions, vol. 56, 214 pp.
Rodriguez et al., 1989, Isomerisation de diènes-1,5 fonctionnalisés par le fer pentacarbonyle, Journal of Organometallic Chemistry, 359(3):343-369.
Su et al., 2018, Radical Deoxychlorination of Cesium Oxalates for the Synthesis of Alkyl Chlorides, Organic Letters, 20(16):4912-4916.
Watkins et al., 2011, Regioselective Rhodium-Catalyzed Hydroformylation of 1,3-Dienes to Highly Enantioenriched β,γ-Unsaturated Aldehyes with Diazaphospholane Ligands, Organic Letters, 13(1):164-167.
Winter, 2004, Spirocyclic Ethers Related to Ambrox™: Synthesis and Structure-Odor Relationships, 87(7):1616-1627.
International search report and written opinion dated Apr. 14, 2022 in application No. PCT/EP2021/073905.
Britelli et al., 1981, New Furoxan Chemistry. 1. Synthesis of diacylfuroxans by reaction of ethynyl acetates with nitrosyl fluoride/nitrosoium tetrafluoroborate, J. Org. Chem., 46(2):312-315.
Fiaud et a., 1990, Substrate Leaving Group Control of the Enantioselectivity in the Palladium-Catalyzed Asymmetric Allylic Substitution of 4-Alkyl-I-vinylcyclohexyl Derivatives, J. Org. Chem. 55:4840-4846.
Gorlich et al., 1958, Athinierung bicyclischer ketone, Chemische Berichte, 91(11): 2388-2394.
Porey et al., Jan. 7, 2020, Alkyne linchpin strategy for drug: pharmacophore conjugation: experimental and computational realization of a meta-selective inverse sonogashira coupling, J. Am. Chem. Soc., 142:3762-3774.
CAS RN 2155021-02-4, File Registry (STN), entered Dec. 10, 2017, 1 p.
Sadhukhan et al., 2017, An expeditious approach to a, a-Dihalo-a'-acetoxyketones from propargylic acetates, ChemistrySelect, 2:8500-8503.
Seiche et al., 2005, Bidentate Ligands by Self-Assembly through Hydrogen Bonding: A General Room Temperature/Ambient Pressure Regioselective Hydroformylation of Terminal Alkenes, Adv. Synth. Catal., 347:1488-1494.

PROCESS FOR PREPARING 3-(CYCLOHEX-1-EN-1-YL)PROPANAL DERIVATIVES

This present application is a U.S. national phase entry under 35 U.S.C. § 371 of PCT Application No. PCT/EP2021/073905, filed Aug. 30, 2021, which claims priority to European Patent Application No. 20193779.4, filed Sep. 1, 2020. The entire contents of these applications are explicitly incorporated herein by this reference.

TECHNICAL FIELD

The present invention relates to the field of perfumery. More particularly, it concerns valuable new chemical intermediates for producing perfuming ingredients. Moreover, the present invention comprises also a process for producing compound of formula (I).

BACKGROUND OF THE INVENTION

In the perfumery industry, there is a constant need to provide compounds imparting novel organoleptic notes. In particular, there is an interest towards aldehydic notes which represent one of the key organoleptic facets of the lily of the valley odor. So, compounds imparting said note are particularly sought after to reconstitute the delicate floral odor of muguet which does not survive even the mildest of extraction methods to yield an essential oil. 3-(cyclohex-1-en-1-yl) propanal derivatives represent compounds imparting note of the muguet-aldehydic olfactive family, such as, for example, 3-(4,4-dimethyl-1-cyclohexen-1-yl)propanal reported in EP 1529770 or 3-[4-(2-methyl-2-propanyl)-1-cyclohexen-1-yl] propanal reported in EP 1054053. However, the access to these derivatives is tedious and requires Grignard reagents, radical chemistry, hydrogenation of dienal or pyrolysis providing the desired compounds with low yield and/or selectivity.

Being products of industrial interest, there is always a need for new processes showing an improved yield or productivity.

The compounds of formula (II), (III) and (IV) which are an object of the present invention, have never been reported or suggested in the context of the preparation of compounds of formula (I). Only a few of said compounds of formula (II) and (III) have been reported in the prior art but none of them as an intermediate towards compounds of formula (I).

So, the prior arts although reporting some derivative of formula (II) and (III) cannot be considered as suggesting the present invention.

SUMMARY OF THE INVENTION

The invention relates to a novel process allowing the preparation of compound of formula (I) with a high yield and high selectivity starting from novel compound of formula (II). The invention process represents a new efficient route toward compound of formula (I).

So, the first object of the present invention is a process for the preparation of a compound of formula (I)

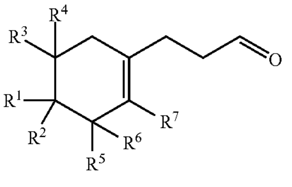

in the form of any one of its stereoisomers or a mixture thereof, and wherein each $R^1$, $R^2$, $R^3$, $R^4$, $R^5$, $R^6$ and $R^7$, independently from each other, represent a hydrogen atom, a $C_{1-6}$ alkyl group or a $C_{2-6}$ alkenyl group, each optionally substituted by a hydroxy or $C_{1-3}$ alkoxy group; or two groups among $R^1$, $R^2$, $R^3$, $R^4$, $R^5$, $R^6$ and $R^7$ are taken together and form $C_{3-8}$ cycloalkyl or $C_{5-8}$ cycloalkenyl group and the others groups have the same meaning as defined above;

comprising a hydroformylation and an elimination step starting from compound of formula (II)

(II)

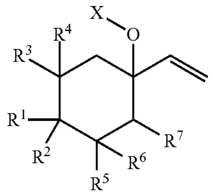

in the form of any one of its stereoisomers or a mixture thereof, and wherein $R^1$, $R^2$, $R^3$, $R^4$, $R^5$, $R^6$ and $R^7$ have the same meaning as defined in formula (I) and X represents a C(O)R group or a $Si(R')_3$ group wherein R is a hydrogen atom, a $C_{1-4}$ alkyl group, a $C_{1-4}$ alkoxy group or a phenyl group, R', independently from each other, are a $C_{1-4}$ alkyl group.

A second object of the present invention is a compound of formula (III)

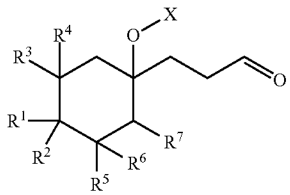

in the form of any one of its stereoisomers or a mixture thereof, and wherein X represents a C(O)R group or a $Si(R')_3$ group wherein R is a hydrogen atom, a $C_{1-4}$ alkyl group, a $C_{1-4}$ alkoxy group or a phenyl group, R', independently from each other, are a $C_{1-4}$ alkyl group; each $R^1$, $R^2$, $R^3$, $R^4$, $R^5$, $R^6$ and $R^7$, independently from each other, represent a hydrogen atom, a $C_{1-6}$ alkyl group or a $C_{2-6}$ alkenyl group, each optionally substituted by a hydroxy or $C_{1-3}$ alkoxy group; or two groups among $R^1$, $R^2$, $R^3$, $R^4$, $R^5$, $R^6$ and $R^7$ are taken together and form $C_{3-8}$ cycloalkyl or $C_{5-8}$ cycloalkenyl group and the others groups have the same meaning as defined above; provided that 1-(3-oxopropyl)cyclohexyl acetate is excluded.

Another object of the present invention is compound of formula (IV')

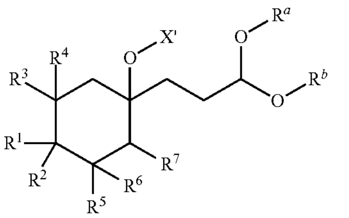

in the form of any one of its stereoisomers or a mixture thereof, and wherein X' is a hydrogen atom, a $C_{1-3}$ alkyl group, a $C_{2-3}$ alkenyl group, a benzyl group or a C(O)R group or a $Si(R')_3$ group wherein R is a hydrogen atom, a $C_{1-4}$ alkyl group, a $C_{1-4}$ alkoxy group or a phenyl group, R', independently from each other, are a $C_{1-4}$ alkyl group; each $R^1$, $R^2$, $R^3$, $R^4$, $R^5$, $R^6$ and $R^7$, independently from each other, represent a hydrogen atom, a $C_{1-6}$ alkyl group or a $C_{2-6}$ alkenyl group, each optionally substituted by a hydroxy or $C_{1-3}$ alkoxy group; or two groups among $R^1$, $R^2$, $R^3$, $R^4$, $R^5$, $R^6$ and $R^7$ are taken together and form $C_{3-8}$ cycloalkyl or $C_{5-8}$ cycloalkenyl group and the others groups have the same meaning as defined above; $R^a$ and $R^b$, independently from each other, represent a $C_{1-4}$ alkyl group or $R^a$ and $R^b$ are taken together and represent a $C_{2-6}$ alkanediyl group; provided that 1-(2-(1,3-dioxolan-2-yl)ethyl)-4-isobutyl-2-methylcyclohexan-1-ol, 1-(2-(1,3-dioxolan-2-yl)ethyl)-4-(tert-butyl)-2-methylcyclohexan-1-ol, 1-(3,3-diethoxypropyl)cyclohexan-1-ol, 1-(2-(1,3-dioxolan-2-yl)ethyl)-4-isopropyl-2-methylcyclohexan-1-ol, 1-(2-(1,3-dioxolan-2-yl)ethyl)-4-(tert-butyl)cyclohexan-1-ol and 1-(2-(1,3-dioxan-2-yl)ethyl)-4-(tert-butyl)cyclohexan-1-ol are excluded.

Another object of the present invention is a compound of formula (V')

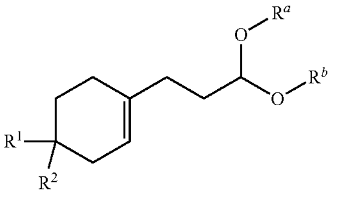

in the form of any one of its stereoisomers or a mixture thereof, and wherein; each $R^1$ and $R^2$, independently from each other, represent a hydrogen atom, a $C_{1-6}$ alkyl group or a $C_{2-6}$ alkenyl group, each optionally substituted by a hydroxy or $C_{1-3}$ alkoxy group; $R^a$ and $R^b$, independently from each other, represent a $C_{1-4}$ alkyl group or $R^a$ and $R^b$ are taken together and represent a $C_{2-6}$ alkanediyl group A further object of the present invention is a compound of formula (IX)

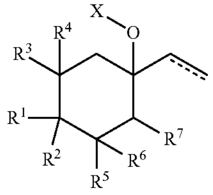

in the form of any one of its stereoisomers or a mixture thereof, and wherein the dotted line represents a double or a triple bond; X represents a C(O)R group or a $Si(R')_3$ group wherein R is a hydrogen atom, a $C_{1-4}$ alkyl group, a $C_{1-4}$ alkoxy group or a phenyl group, R', independently from each other, are a $C_{1-4}$ alkyl group; each $R^1$, $R^2$, $R^3$, $R^4$, $R^5$, $R^6$ and $R^7$, independently from each other, represent a hydrogen atom, a $C_{1-6}$ alkyl group or a $C_{2-6}$ alkenyl group, each optionally substituted by a hydroxy or $C_{1-3}$ alkoxy group; or two groups among $R^1$, $R^2$, $R^3$, $R^4$, $R^5$, $R^6$ and $R^7$ are taken together and form $C_{3-8}$ cycloalkyl or $C_{5-8}$ cycloalkenyl group and the others groups have the same meaning as defined above; provided that 1-vinylcyclohexyl acetate, 1-ethynylcyclohexyl acetate, 1-vinylcyclohexyl propionate, 4-methyl-1-vinylcyclohexyl acetate, 2-methyl-1-vinylcyclohexyl acetate, 1-ethynyl-2-methylcyclohexyl acetate, 2-ethyl-1-vinylcyclohexyl acetate, 2-isopropyl-1-vinylcyclohexyl acetate, 2-secbutyl-1-vinylcyclohexyl acetate, 2-isopropyl-5-methyl-1-vinylcyclohexyl acetate, 2-allyl-1-vinylcyclohexyl acetate, 4-tert-butyl-1-vinylcyclohexyl acetate, 1-vinyldecahydronaphthalen-1-yl acetate and 1-ethynyldecahydronaphthalen-1-yl acetate are excluded.

DESCRIPTION OF THE INVENTION

It has now been surprisingly found that valuable perfuming ingredients 3-(cyclohex-1-en-1-yl)propanal derivatives of formula (I) can be obtained from new chemical intermediates, as defined herein below in formula (II), (III), (IV). The invention's process represents a new route toward compounds of formula (I) with overall higher yield, compared to the methods known from the prior art.

So, the first object of the invention is a process for the preparation of a compound of formula (I)

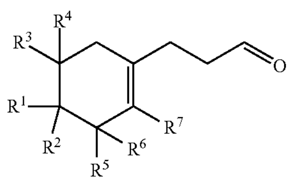

in the form of any one of its stereoisomers or a mixture thereof, and wherein each $R^1$, $R^2$, $R^3$, $R^4$, $R^5$, $R^6$ and $R^7$, independently from each other, represent a hydrogen atom, a $C_{1-6}$ alkyl group or a $C_{2-6}$ alkenyl group, each optionally substituted by a hydroxy or $C_{1-3}$ alkoxy group; or two groups among $R^1$, $R^2$, $R^3$, $R^4$, $R^5$, $R^6$ and $R^7$ are taken together and form $C_{3-8}$ cycloalkyl or $C_{5-8}$ cycloalkenyl group and the others groups have the same meaning as defined above;

comprising a hydroformylation and an elimination step starting from compound of formula (II)

(II)

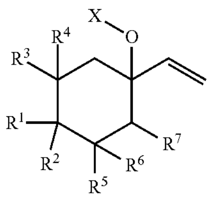

in the form of any one of its stereoisomers or a mixture thereof, and wherein $R^1$, $R^2$, $R^3$, $R^4$, $R^5$, $R^6$ and $R^7$ have the same meaning as defined in formula (I) and X represents a C(O)R group or a $Si(R')_3$ group wherein R is a hydrogen atom, a $C_{1-4}$ alkyl group, a $C_{1-4}$ alkoxy group or a phenyl group, R', independently from each other, are a $C_{1-4}$ alkyl group.

For the sake of clarity, by the expression "any one of its stereoisomers or a mixture thereof", or the similar, it is meant the normal meaning understood by a person skilled in the art, i.e. that the compound of formula (I) and (II) can be a pure enantiomer or a mixture of enantiomers. In other words, the compound of formula (I) and (II) may possess at least one stereocenter which can have two different stereochemistries (e.g. R or S). The compounds of formula (I) and (II) may even be in the form of a pure enantiomer or in the form of a mixture of enantiomers. The compounds of formula (I) and (II) may even be in the form of a pure diastereoisomer or in the form of a mixture of diastereoisomer when compounds of formula (I) and (II) possess more than one stereocenter. The compounds of formula (I) and (II) can be in a racemic form or scalemic form. Therefore, the compounds of formula (I) and (II) can be one stereoisomer or in the form of a composition of matter comprising, or consisting of, various stereoisomers.

The term "optionally" is understood that a certain group to be optionally substituted can or cannot be substituted with a certain functional group.

For the sake of clarity, by the expression "comprising a hydroformylation and an elimination step", it is meant that the hydroformylation reaction and the elimination reaction may be performed in any order. In other words, the invention process may comprise a hydroformylation step followed by an elimination step or the invention process may comprise an elimination step followed by a hydroformylation step.

The terms "alkyl" and "alkenyl" are understood as comprising branched and linear alkyl and alkenyl groups. The terms "alkenyl" and "cycloalkenyl" are understood as comprising 1, 2 or 3 olefinic double bonds, preferably 1 or 2 olefinic double bonds. The terms "cycloalkyl" and "cycloalkenyl" are understood as comprising a monocyclic or fused, spiro and/or bridged bicyclic or tricyclic cycloalkyl and cycloalkenyl, groups, preferably monocyclic cycloalkyl and cycloalkenyl groups.

For the sake of clarity, by the expression "two groups among $R^1$, $R^2$, $R^3$, $R^4$, $R^5$, $R^6$ and $R^7$ are taken together and form $C_{3-8}$ cycloalkyl or $C_{5-8}$ cycloalkenyl group", it is meant that the carbon atom(s) to which both groups are bonded is/are included into the $C_{5-8}$ cycloalkyl or $C_{5-8}$ cycloalkenyl group.

According to any embodiment of the invention, at least one group among $R^1$, $R^2$, $R^3$, $R^4$, $R^5$, $R^6$ and $R^7$ may be a $C_{1-6}$ alkyl group or a $C_{2-6}$ alkenyl group, each optionally substituted by a hydroxy or $C_{1-3}$ alkoxy group, and the others may be, independently from each other, a hydrogen atom, a $C_{1-6}$ alkyl group or a $C_{2-6}$ alkenyl group, each optionally substituted by a hydroxy or $C_{1-3}$ alkoxy group. Particularly, at least three groups among $R^1$, $R^2$, $R^3$, $R^4$, $R^5$. $R^6$ and $R^7$ may be a hydrogen atom, the others, may be, independently from each other, a hydrogen atom, a $C_{1-6}$ alkyl group or a $C_{2-6}$ alkenyl group, each optionally substituted by a hydroxy or $C_{1-3}$ alkoxy group. Particularly, four groups among $R^1$, $R^2$, $R^3$, $R^4$, $R^5$, $R^6$ and $R^7$ may be a hydrogen atom, the others, may be, independently from each other, a hydrogen atom, a $C_{1-6}$ alkyl group or a $C_{2-6}$ alkenyl group, each optionally substituted by a hydroxy or $C_{1-3}$ alkoxy group. Particularly, one, two, three or four groups among $R^1$, $R^2$, $R^3$, $R^4$, $R^5$, $R^6$ and $R^7$ may be a $C_{1-6}$ alkyl group or a $C_{2-6}$ alkenyl group, each optionally substituted by a hydroxy or $C_{1-3}$ alkoxy group, and the others may be a hydrogen atom. Even more particularly, one or two groups among $R^1$, $R^2$, $R^3$, $R^4$, $R^5$, $R^6$ and $R^7$ may be a $C_{1-6}$ alkyl group or a $C_{2-6}$ alkenyl group, each optionally substituted by a hydroxy or $C_{1-3}$ alkoxy group, and the others may be a hydrogen atom.

According to any embodiment of the invention, $R^3$, $R^4$, $R^5$, $R^6$ and $R^7$, independently from each other, may be a hydrogen atom or a $C_{1-4}$ alkyl group, optionally substituted by a hydroxy or $C_{1-3}$ alkoxy group. Particularly, $R^3$, $R^4$, $R^5$, $R^6$ and $R^7$, independently from each other, may be a hydrogen atom or a $C_{1-3}$ alkyl group. Particularly, $R^3$, $R^4$, $R^5$, $R^6$ and $R^7$, independently from each other, may be a hydrogen atom.

According to a particular embodiment of the invention, $R^1$, $R^2$, $R^3$, $R^6$ and $R^7$, independently from each other, may be a hydrogen atom and $R^4$, and $R^5$ may be a hydrogen atom or a $C_{1-3}$ alkyl group. Particularly, $R^1$, $R^2$, $R^3$, $R^6$ and $R^7$, independently from each other, may be a hydrogen atom and $R^4$ may be a hydrogen atom and $R^5$ may be a $C_{1-3}$ alkyl group or $R^4$ may be a $C_{1-3}$ alkyl group and $R^5$ may be a hydrogen atom.

According to any embodiment of the invention, the compound of formula (I) is of formula (I')

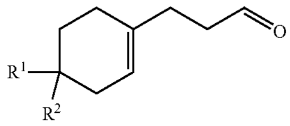

in the form of any one of its stereoisomers or a mixture thereof, and wherein each $R^1$ and $R^2$ have the same meaning as defined above;

and said compound of formula (II) is of formula (II')

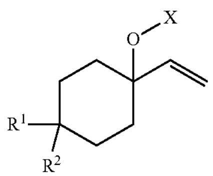

in the form of any one of its stereoisomers or a mixture thereof, and wherein each X, $R^1$ and $R^2$ have the same meaning as defined above.

According to any embodiment of the invention, $R^1$ may be a $C_{1-4}$ alkyl group or a $C_{2-4}$ alkenyl group. Particularly, $R^1$ may be a methyl, an ethyl, a propyl, an iso-propyl, an iso-butyl, a sec-butyl, a tert-butyl or a n-butyl group. Particularly, $R^1$ may be a methyl, an ethyl, a propyl, an iso-propyl, an iso-butyl, a sec-butyl or a n-butyl group. Even more particularly, $R^1$ may be a methyl group.

According to any embodiment of the invention, $R^2$ may be a hydrogen atom or a $C_{1-3}$ alkyl group or a $C_{2-3}$ alkenyl group. Particularly, $R^2$ may be a hydrogen atom, a methyl, an ethyl, a propyl or an iso-propyl group. Even more particularly, $R^2$ may be a methyl group.

According to a particular embodiment of the invention, when $R^2$ is a hydrogen atom, preferably $R^1$ is not a tert-butyl group.

According to any embodiment of the invention, X may be a C(O)R group wherein R may be a hydrogen atom or a $C_{1-4}$ alkyl group. Particularly, X may be a C(O)R group wherein R may be a $C_{1-3}$ alkyl group. Even more particularly, X may be an acetate group.

According to a particular embodiment of the invention, the invention's process comprises a hydroformylation followed by an elimination step starting from compound of formula (II). The hydroformylation of compound of formula (II) provides a compound of formula (III)

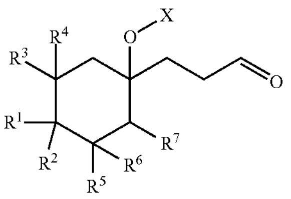

in the form of any one of its stereoisomers or a mixture thereof, and wherein X, $R^1$, $R^2$, $R^3$, $R^4$, $R^5$, $R^6$ and $R^7$ have the same meaning as defined above.

The hydroformylation may provide, as a side product, compound of formula (III')

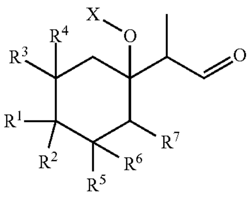

in the form of any one of its stereoisomers or a mixture thereof, and wherein X, $R^1$, $R^2$, $R^3$, $R^4$, $R^5$, $R^6$ and $R^7$ have the same meaning as defined above. At most 40 wt % of compound of formula (III') may be formed. Particularly, at most 35 wt % of compound of formula (III') may be formed. Particularly, at most 30 wt % of compound of formula (III') may be formed. Particularly, at most 20 wt % of compound of formula (III') may be formed. Particularly, at most 10 wt % of compound of formula (III') may be formed. Particularly, at most 5 wt % of compound of formula (III') may be formed. Even more particularly, the hydroformylation does not provide compound of formula (Ill').

For the sake of clarity, by the expression "hydroformylation", or the similar, it is meant the normal meaning understood by a person skilled in the art, i.e. the reaction is performed in a presence of a metal catalyst such as Rhodium, Cobalt or Platinum complex, preferably a Rhodium complex, carbon monoxide, hydrogen and optionally a ligand such as the one comprising a phosphorous atom.

According to any embodiment of the invention, the hydroformylation is performed in a presence of a Rhodium complex. The Rhodium complexes that can be used in the present invention include but are not limited to $Rh(acac)(CO)_2$, $RhCl_3$, $Rh_2AcO_4$, $[Rh(OAc)(COD)]_2$, $Rh_4(CO)_{12}$, $Rh_6(CO)_{16}$, $RhCl(CO)(PPh_3)_2$, $Rh(C_2H_4)_2(acac)$, $[Rh(Cl)(COD)]_2$, $[Rh(Cl)(COE)_2]_2$, $[Rh(OAc)(CO)_2]_2$, Rh(acac)(COD), $HRh(CO)(PPh_3)_3$, $RhCl(PPh_3)_3$, $[Rh(NBD)_2]BF_4$, $[Rh(OMe)(COD)]_2$ and $[Rh(OH)(COD)]_2$ wherein acac represents an acetyl acetonate group, Ac an acetyl group, COD a 1,5-cyclooctadiene group, COE a cyclooctene group, Ph a phenyl group. Particularly, the Rhodium complex may be selected from the group consisting of $Rh(acac)(CO)_2$, $[Rh(OAc)(COD)]_2$, $RhCl(CO)(PPh_3)_2$, $Rh(C_2H_4)_2(acac)$, $[Rh(Cl)(COD)]_2$, $[Rh(Cl)(COE)_2]_2$, $[Rh(OAc)(CO)_2]_2$, Rh(acac)(COD), $HRh(CO)(PPh_3)_3$, $RhCl(PPh_3)_3$, $[Rh(NBD)_2]BF_4$, $[Rh(OMe)(COD)]_2$, and $[Rh(OH)(COD)]_2$. Even more particularly, the Rhodium complex may be selected from the group consisting of $Rh(acac)(CO)_2$, Rh(acac)(COD), $HRh(CO)(PPh_3)_3$, $[Rh(OMe)(COD)]_2$ and $[Rh(OH)(COD)]_2$. Said complex can be added into the reaction medium of the invention's process in a large range of concentrations. As non-limiting examples, one can cite as complex concentration values those ranging from about 0.0005 mol % to about 5 mol %, relative to the amount of substrate, preferably from 0.001 mol % to about 5 mol %, relative to the amount of substrate. Preferably, the complex concentration will be comprised between 0.0025 mol % to 2 mol %. It goes without saying that the optimum concentration of the complex will depend, as the person skilled in the art knows, on the nature of the latter, on the nature of the substrate, on the nature of the ligand, on the reaction temperature as well as on the desired time of reaction.

According to any embodiment of the invention, the hydroformylation is performed in a presence of a mono- or bidentate phosphorous ligand. Particularly, the phosphorous ligand may be a bidentate phosphorous ligand. Particularly, the mono- or bidentate phosphorous ligand is not selected from the group consisting of [1-[2-(12,14-dioxa-13-phosphapentacyclo[$13.8.0.0^{2,11}.0^{3,8}.0^{18,23}$]tricosa-1(15),2(11),3,5,7,9,16,18,20,22-decaen-13-yloxy)naphthalen-1-yl]naphthalen-2-yl]-diphenylphosphane or diazaphospholane ligand.

According to any embodiment of the present invention, the hydroformylation may be performed in a presence of a monodentate phosphorous ligand of formula $PR^8{}_3$, wherein $R^8$ is a $C_1$-$C_{12}$ group, such as linear, branched or cyclic alkyl, alkoxy or aryloxy group optionally substituted, substituted or unsubstituted phenyl, diphenyl, 2-furanyl, naphthyl or di-naphthyl group, or two $R^8$ groups are taken together and form a phosphatrioxa-adamantane and the other $R^8$ group has the same meaning as above. More particularly $R^8$ may represent a substituted or unsubstituted phenyl, diphenyl, naphthyl or di-naphthyl group. Possible substituents are those cited below for the group $R^9$. Preferably, the monodentate phosphorous ligand is a triphenylphosphine.

According to any one of the above embodiments, the hydroformylation may be performed in presence of a bidentate phosphorous ligand of formula $(R^9)_2P\text{-}Q\text{-}P(R^9)_2$ (A)

wherein each $R^9$, taken separately, represents a $C_{6-10}$ aromatic group optionally substituted or a cyclohexyl group optionally substituted, or the two $R^9$ bonded to the same P atom, taken together, represent a 1,1'-biphenyl-2,2'-dioxy optionally substituted; and Q represents a group of formula (i)

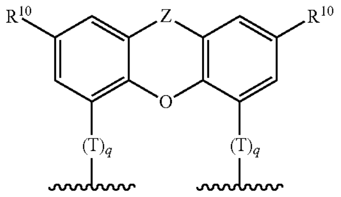

wherein q is 0 or 1, each T, independently from each other, represent an oxygen atom or a $CH_2$ group, each $R^{10}$, independently from each other, represents a hydrogen atom or a $C_{1-8}$ alkyl group, and Z represents an oxygen or sulfur atom or a $C(R^{11})_2$, $Si(R^{12})_2$ or $NR^{11}$ group, in which $R^{11}$ is a hydrogen atom or a $R^{12}$ group, $R^{12}$ representing a $C_{1-4}$ linear or branched alkyl group, preferably methyl group; or (ii)

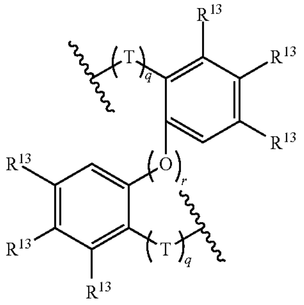

in the form of any one of its enantiomers, and wherein q is 0 or 1, r is 0 or 1, each T, independently from each other, represent an oxygen atom or a $CH_2$ group, $R^{13}$ independently from each other, represent a hydrogen atom or a $C_{1-4}$ alkyl optionally substituted by one to three halogen atom or alkoxy group;

(iii)

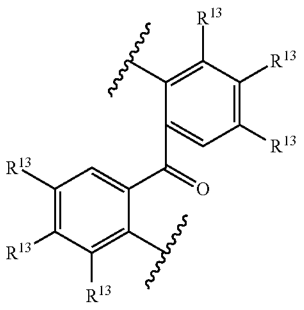

in the form of any one of its enantiomers, and wherein $R^{13}$ have the same meaning as above;

and the wavy lines indicate the position of the bond between said Q group and the rest of the compound (A).

According to any one of the above embodiments, Q may be a group of formula (i) or (ii).

According to any one of the above embodiments, each $R^9$ may be a $C_{6-10}$ aromatic group optionally substituted or a cyclohexyl group optionally substituted.

According to any one of the above embodiments, by "aromatic group or ring" it is meant a phenyl or naphthyl group, and in particular a phenyl group.

According to any one of the above embodiments, each $R^9$ may be a phenyl group, a cyclohexyl group, a 3,5-dimethyl-phenyl, a 3,5-di($CF_3$)-phenyl, a 3,5-dimethyl-4-methoxy-phenyl group.

According to any one of the above embodiments, the $R^{10}$ may be a hydrogen atom.

According to any one of the above embodiments, Z may be a $CMe_2$, $SiMe_2$, NH or NMe group. Particularly, Z may be a $CMe_2$ group.

According to any one of the above embodiments, non-limiting examples of possible substituents of $R^9$ are one, two, three or four groups selected amongst the halogen atoms, or $C_{1-10}$ alkoxy, alkyl, alkenyl, pyridyl or perhalo-hydrocarbon group. Two substituents may be taken together to form a $C_{4-8}$ cycloalkyl group. The expression "perhalo-hydrocarbon" has here the usual meaning in the art, e.g. a group such as $CF_3$ for instance. In particular said substituents are one or two halogen atoms, such as F or Cl, or $C_{1-4}$ alkoxy or alkyl groups, or $CF_3$ groups.

According to any one of the above embodiments, said $R^9$, may be non-substituted.

According to any one of the above embodiments, the ligand of formula (A) can be in a racemic or optically active form.

Non limiting example of bidendate phosphorous ligand may include 2,2'-bis((di(1H-pyrrol-1-yl)phosphanyl)oxy)-1,1'-binaphthalene, 1,1'-((naphthalen-2-yloxy)phosphanediyl)bis(1H-pyrrole), 2,2'-bis((di(1H-pyrrol-1-yl)phosphanyl)oxy)-1,1'-biphenyl, (9,9-dimethyl-9H-xanthene-4,5-diyl)bis(diphenylphosphine), 2,2'-bis((di(1H-pyrrol-1-yl)phosphaneyl)oxy)-5,5',6,6',7,7',8,8'-octahydro-1,1'-binaphthalene, 1,1',1'',1'''-(((2,7-di-tert-butyl-9,9-dimethyl-9H-xanthene-4,5-diyl)bis(oxy))bis(phosphanetriyl))tetrakis(1H-pyrrole), 6,6'-[(3,3'-Di-tert-butyl-5,5'-dimethoxy-1,1'-biphenyl-2,2'-diyl)bis(oxy)]bis(dibenzo[d,f][1,3,2]dioxaphosphepin), (Oxydi-2,1-phenylene)bis(diphenylphosphine), 2,2'-Bis(diphenylphosphinomethyl)-1,1'-biphenyl, 4,6-bis(diphenylphosphanyl)-10H-phenoxazine, 2-((3,3'-di-tert-butyl-2'-((4,8-di-tert-butyl-2,10-dimethoxydibenzo[d,f][1,3,2]dioxaphosphepin-6-yl)oxy)-5,5'-dimethoxy-[1,1'-biphenyl]-2-yl)oxy)-4H-naphtho[2,3-d][1,3,2]dioxaphosphinin-4-one, 2-((3,3'-di-tert-butyl-2'-((4,8-di-tert-butyl-2,10-dimethoxydibenzo[d,f][1,3,2]dioxaphosphepin-6-yl)oxy)-5,5'-dimethoxy-[1,1'-biphenyl]-2-yl)oxy)-8-methyl-4H-benzo[d][1,3,2]dioxaphosphinin-4-one, (1S,1'S)-(−)-(2,7-di-tert-butyl-9,9-dimethyl-9H-xanthene-4,5-diyl)bis((1-naphthyl) (phenyl)phosphine), (1S,1'S)-(−)-(2,7-di-tert-butyl-9,9-dimethyl-9H-xanthene-4,5-diyl)bis((4-methylphenyl) (phenyl)phosphine), 8-methyl-2-((3,3',5,5'-tetra-tert-butyl-2'-((2,4,8,10-tetra-tert-butyldibenzo[d,f][1,3,2]dioxaphosphepin-6-yl)oxy)-[1,1'-biphenyl]-2-yl)oxy)-4H-benzo[d][1,3,2]dioxaphosphinin-4-one, 2-((3,3'-di-tert-butyl-2'-((4,8-di-tert-butyl-2,10-dimethoxydibenzo[d,f][1,3,2]dioxaphosphepin-6-yl)oxy)-5,5'-dimethoxy-[1,1'-biphenyl]-2-yl)oxy)-8-isopropyl-5-methyl-4H-benzo[d][1,3,2]dioxaphosphinin-4-one, (1S,1'S)-(+)-(9,9-Dimethyl-9H-xanthene-4,5-diyl)bis((2-methoxyphenyl)(phenyl) phosphine), (1S,1'S)-(+)-(2,7-di-tert-butyl-9,9-dimethyl-9H-xanthene-4,5-diyl)bis((2-methoxyphenyl)(phenyl)phosphine), (1S,1'S)-(+)-(9,9-Dimethyl-9H-xanthene-4,5-diyl)bis((2-methylphenyl) (phenyl) phosphine), (1S,1'S)-(−)-(9,9-Dimethyl-9H-xanthene-4,5-diyl)bis(naphthalen-2-yl(phenyl)phosphine), (1S,1'S)-(−)-(9,9-Dimethyl-9H-xanthene-4,5-diyl)bis((4-methoxyphenyl)(phenyl) phosphine), (1S,1'S)-(−)-(2,7-di-tert-butyl-9,9-dimethyl-9H-xanthene-4,5-diyl)bis((2-naphthyl) (phenyl)phosphine), (1S,1'S)-(−)-(9,9-Dimethyl-9H-xanthene-4,5-diyl)bis(naphthalen-1-yl(phenyl)phosphine), (1S,1'S)-(+)-(2,7-di-tert-butyl-9,9-dimethyl-9H-xanthene-4,5-diyl)bis((2-isopropoxyphenyl)(phenyl)phosphine), (1S,1'S)-(+)-(2,7-di-tert-butyl-9,9-dimethyl-9H-xanthene-4,5-diyl)bis((2-isopropylphenyl)(phenyl)phosphine) or (1S,1'S)-(−)-(2,7-di-tert.-butyl-9,9-dimethyl-9H-xanthen-4,5-diyl) bis((dibenzo[b,d]-furan-4-yl)(phenyl)phosphine), (2,7-di-tert-butyl-9,9-dimethyl-9H-xanthene-4,5-diyl)bis((4-methoxyphenyl)(phenyl)phosphane), (4,4',6,6'-Tetramethoxybiphenyl-2,2'-diyl) bis{bis[3,5-bis (trifluoromethyl)phenyl]phosphine}.

Particularly, the ligand is a bidentate phosporous ligand which may be selected from the group consisting of (9,9-dimethyl-9H-xanthene-4,5-diyl)bis(diphenylphosphine), 1,1',1'',1'''-(((2,7-di-tert-butyl-9,9-dimethyl-9H-xanthene-4,5-diyl)bis(oxy))bis(phosphanetriyl))tetrakis(1H-pyrrole), 6,6'-[(3,3'-Di-tert-butyl-5,5'-dimethoxy-1,1'-biphenyl-2,2'-diyl)bis(oxy)]bis(dibenzo[d,f][1,3,2]dioxaphosphepin), (Oxydi-2,1-phenylene)bis(diphenylphosphine), 2,2'-Bis(diphenylphosphinomethyl)-1,1'-biphenyl, 4,6-bis(diphenylphosphanyl)-10H-phenoxazine, 2-((3,3'-di-tert-butyl-2'-((4,8-di-tert-butyl-2,10-dimethoxydibenzo[d,f][1,3,2] dioxaphosphepin-6-yl)oxy)-5,5'-dimethoxy-[1,1'-biphenyl]-2-yl)oxy)-4H-naphtho[2,3-d][1,3,2]dioxaphosphinin-4-one, 2-((3,3'-di-tert-butyl-2'-((4,8-di-tert-butyl-2,10-dimethoxydibenzo[d,f][1,3,2]dioxaphosphepin-6-yl)oxy)-5,5'-dimethoxy-[1,1'-biphenyl]-2-yl)oxy)-8-methyl-4H-benzo [d][1,3,2]dioxaphosphinin-4-one, (1S,1'S)-(−)-(2,7-di-tert-butyl-9,9-dimethyl-9H-xanthene-4,5-diyl)bis((1-naphthyl) (phenyl)phosphine) or (1S,1'S)-(−)-(2,7-di-tert-butyl-9,9-dimethyl-9H-xanthene-4,5-diyl)bis((4-methylphenyl) (phenyl)phosphine).

The phosphorous ligand can be added into the reaction medium of the invention's process in a large range of concentrations. As non-limiting examples, one can cite as phosphorous ligand concentration values those ranging from about 0.001 mol % to about 50 mol %, relative to the amount of the of substrate, preferably from 0.005 mol % to about 50 mol %, relative to the amount of the of substrate, preferably from about 0.005 mol % to about 15 mol %, relative to the amount of the of substrate. The optimum concentration of the phosphorous ligand will depend, as the person skilled in the art knows, on the nature of the latter, on the nature of the substrate, on the nature of the metal complex, on the reaction temperature as well as on the desired time of reaction.

According to any one of the above embodiments, carbon monoxide and hydrogen gas may be generated in situ by known methods by the person skilled in the art, e.g. from methyl formate, formic acid, or formaldehyde. The $CO/H_2$ gas volume ratio is comprised between 2/1 to 1/5, preferably between 1/1 to 1/5 or preferably between 2/1 to 1/2, preferably between 1.5/1 to 1/1.5 and more preferably the ratio is 1/1.

The reaction can be carried out in the presence or absence of a solvent. When a solvent is required or used for practical reasons, then any solvent current in such reaction type can be used for the purposes of the invention. Non-limiting examples include $C_{6-12}$ aromatic solvents such as toluene, 1,3-diisopropylbenzene, cumene or pseudocumene, or mixtures thereof, alcoholic solvents such as methanol, ethanol, 2-methylbutan-2-ol or mixtures thereof, hydrocarbon solvents such as cyclohexane, heptane or mixtures thereof, esteric solvent such as n-butyl acetate, iso-propyl acetate, ethyl acetate or ethereal solvents such as methyl tetrahydrofuran, tetrahydrofuran or mixtures thereof. The choice of the solvent is function of the nature of the substrate and/or catalyst and the person skilled in the art is well able to select the solvent most suitable in each case to optimize the reaction.

The hydroformylation reaction can be carried out at a temperature in the range comprised between 50° C. and 150° C., more preferably in the range comprised between 80° C. and 130° C., or even between 90° C. and 110° C. Of course, a person skilled in the art is also able to select the preferred temperature according to the melting and boiling point of the starting and final products as well as the desired time of reaction or conversion.

The hydroformylation can be carried out at a $CO/H_2$ pressure comprised between 1 bar and 50 bar, preferably in the range of between 10 bar and 50 bar, more preferably in the range of between 25 bar and 35 bar. Of course, a person skilled in the art is well able to adjust the pressure as a function of the catalyst load and of the dilution of the substrate in the solvent.

According to any embodiment of the invention, the aldehyde group of compound of formula (III) may be protected before the elimination step or the elimination step may be performed directly on compound of formula (III) providing compound of formula (I). When the elimination step is performed on compound of formula (III), the elimination is performed under acidic conditions or under thermal pyrolysis. The acid may be selected from the group consisting of pTsOH, MsOH, TfOH, $H_2SO_4$, $H_3PO_4$, $KHSO_4$, $NaHSO_4$, oxalic acid, formic acid, $BF_3{\cdot}Et_2O$, $BF_3{\cdot}AcOH$, Alox acidic (Axsorb A2-5, $Al_2O_3$ 504C), Amberlyst 15, $SiO_2$, TFA, Wayphos, polyphosphoric acid, Zeolite (CBV 21A sold by Zeolist, CBV 780 sold by Zeolist, CP814E sold by Zeolist), boric acid, $Al_2(SO_4)_3$, CSA, Pyridinium p-toluenesulfonate, $ZnBr_2$, K10-S300 (Bentonite) sold by Clariant, F24 X (Bentonite) sold by Clariant, Siral® 40 HPV sold by Sasol, HCl, HBr, $Zn(SO_4)_2$, $ZnCl_2$ $MgI_2$, and a mixture thereof. The thermal pyrolysis may be carried out at a temperature comprised in the range between 300° C. and 600° C.

The elimination reaction on the aldehydic substrate can be carried out in the presence or absence of a solvent. When a solvent is required or used for practical reasons, then any solvent current in such reaction type can be used for the purposes of the invention. Non-limiting examples include $C_{6-12}$ aromatic solvents such as toluene, xylene, 1,3-diisopropylbenzene, cumene or pseudocumene, or mixtures thereof, chlorinated solvents such as dichloromethane, dichloroethane or mixtures thereof, hydrocarbon solvents such as cyclohexane or heptane. The choice of the solvent is function of the nature of the substrate and/or catalyst and the person skilled in the art is well able to select the solvent most suitable in each case to optimize the reaction.

The elimination step, on the aldehydic substrate, under acidic conditions can be carried out at a temperature in the range comprised between 20° C. and 110° C. Of course, a person skilled in the art is also able to select the preferred temperature according to the melting and boiling point of the starting and final products as well as the desired time of reaction or conversion.

According to any embodiment of the invention, the process comprises the step of a) hydroformylation of compound of formula (II) to obtain compound of formula (III)

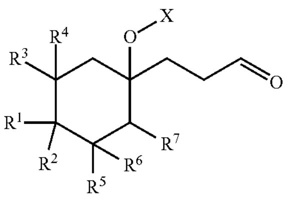

in the form of any one of its stereoisomers or a mixture thereof, and wherein X, $R^1$, $R^2$, $R^3$, $R^4$, $R^5$, $R^6$ and $R^7$ have the same meaning as defined above b) protection of the aldehyde group of compound formula (III) obtained in step a) in the form of an acetal of formula (IV)

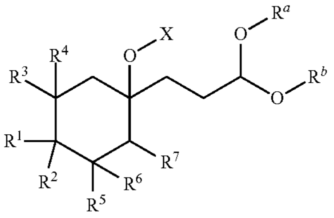

in the form of any one of its stereoisomers or a mixture thereof, and wherein X, $R^1$, $R^2$, $R^3$, $R^4$, $R^5$, $R^6$ and $R^7$ have the same meaning as defined above and $R^a$ and $R^b$, independently from each other, represent a $C_{1-4}$ alkyl group or $R^a$ and $R^b$ a taken together and represent a $C_{2-6}$ alkanediyl group;

c) elimination of the OX group of the compound of formula (IV) followed by an isomerisation to from a compound of formula (V)

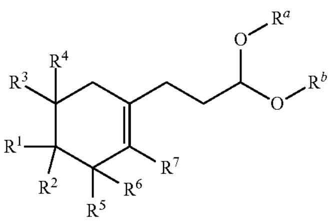

in the form of any one of its stereoisomers or a mixture thereof, and wherein $R^1$, $R^2$, $R^3$, $R^4$, $R^5$, $R^6$, $R^7$, $R^a$ and $R^b$ have the same meaning as defined above; and d) deprotection of the acetal group to obtain compound of formula (I).

The term "alkanediyl" is understood as comprising branched and linear alkanediyl group.

According to any embodiment of the invention, $R^a$ and $R^b$ may be taken together and represent a $C_{2-6}$ alkanediyl group. Particularly, $R^a$ and $R^b$ may be taken together and represent a $C_{2-4}$ alkanediyl group. Even more particularly, $R^a$ and $R^b$ are taken together and represent a $(CH_2)_n$ group wherein n may be 2 or 3; preferably n may be 2.

According to any embodiment of the invention, the protection of the aldehyde group of compound formula (III) obtained in step a) in the form of an acetal of formula (IV) may be carried out under normal condition known by the person skilled in the art, i.e. with an $C_{1-4}$ trialkyl orthoformate, $C_{1-4}$ alcohol and $C_{2-6}$ diol and in the presence of an acid. Specific and non-limiting examples of acid may be selected from the group consisting of $H_2SO_4$, $KHSO_4$, $NaHSO_4$, $H_3PO_4$, $NaHSO_4$, Amberlyst 15, pTsOH, MsOH, TfOH, CSA, oxalic acid, formic acid, TFA, $BF_3 \cdot Et_2O$, $BF_3 \cdot AcOH$, $HBF_4$, wayphos, $SiO_2$, Pyridinium p-toluenesulfonate, Zeolite and $Al_2(SO_4)_3$, F24 X (Bentonite), boric acid and a mixture thereof.

Specific and non-limiting examples of $C_{1-4}$ trialkyl orthoformate, $C_{1-4}$ alcohol and $C_{2-6}$ diol may be selected from the group consisting of trimethyl orthoformate, triethyl orthoformate, methanol, ethanol, ethylene glycol, 1,2-butanediol, 2,3-butanediol, 2,3-dimethyl-3-hydroxy-2-butanol, diglycerol, trans-1,2-cyclohexandiol, neopentylglycol, 1,3-propanediol, 2-methyl-2-propyl-1,3-propanediol, 1,2-propanediol, 2-methyl-1,2-propanediol, 2,2-dimethyl-1,3-propanediol. Particularly, the acetal formation may be carried out with a $C_{2-6}$ diol, particularly with ethylene glycol.

The $C_{1-4}$ trialkyl orthoformate, $C_{1-4}$ alcohol or $C_{2-6}$ diol can be added into the reaction medium of the invention's process in a large range of concentrations. As non-limiting examples, one can cite as $C_{1-4}$ trialkyl orthoformate or $C_{2-5}$ diol concentration values those ranging from about 1 to about 2 equivalents, relative to the amount of the of substrate. As non-limiting examples, one can cite as $C_{1-4}$ alcohol concentration values those ranging from about 2 to about 4 equivalents, relative to the amount of the of substrate. The optimum concentration of the $C_{1-4}$ trialkyl orthoformate, $C_{1-4}$ alcohol or $C_{2-6}$ diol will depend, as the person skilled in the art knows, on the nature of the latter, on the nature of the substrate, on the reaction temperature as well as on the desired time of reaction.

The acid, used in step for protecting of the aldehyde group of formula (III) in the form of an acetal, can be added into the reaction medium of the invention's process in a large range of concentrations. As non-limiting examples, one can cite as acid concentration values those ranging from about 0.1 to about 5 mol %, relative to the amount of the of substrate. The optimum concentration of said acid will depend, as the person skilled in the art knows, on the nature of the latter, on the nature of the substrate, on the reaction temperature as well as on the desired time of reaction.

According to any one of the invention's embodiments, the invention's process to form compound of formula (IV) is carried out at a temperature comprised between 25° C. and 120° C. In particular, the temperature is in the range between 50° C. and 110° C. Of course, a person skilled in the art is also able to select the preferred temperature as a function of the melting and boiling point of the starting and final products as well as the desired time of reaction or conversion.

The acetal formation can be carried out in the presence or absence of a solvent. When a solvent is required or used for practical reasons, then any solvent current in such reaction type can be used for the purposes of the invention. Non-limiting examples include $C_{6-12}$ aromatic solvents such as xylene, toluene, 1,3-diisopropylbenzene, cumene or pseudocumene, or mixtures thereof, hydrocarbon solvents such as cyclohexane, heptane or mixtures thereof. The choice of the solvent is function of the nature of the substrate and/or catalyst and the person skilled in the art is well able to select the solvent most suitable in each case to optimize the reaction.

According to any embodiment of the invention, the elimination of the OX group group of the compound of formula (IV) followed by an isomerisation to from a compound of formula (V) may be carried out under normal conditions known by the person skilled in the art, i.e. such as for example pyrolysis followed by isomerisation under acidic conditions or in presence of metal catalyst in elemental form or supported such as such as Rhodium, Ruthenium, Iridium, Platinum or Palladium complex. The elimination may form the exo isomer (with a double bond in the alkyl chain), the endo isomer (with a double bond inside the ring—desired compounds) or a mixture thereof. The isomerisation allows converting the exo isomer into the endo isomer. Particularly, the elimination and isomerisation may be a one pot process performed in the presence of an acid. The acid may be a Lewis acid or a Bronsted acid. Specific and non-limiting examples of acid may be selected from the group consisting of p-TsOH, MsOH, TfOH, $H_2SO_4$, $H_3PO_4$, $KHSO_4$, $NaHSO_4$, oxalic acid, formic acid, $BF_3{\cdot}Et_2O$, $BF_3{\cdot}AcOH$, Alox acidic (Axsorb A2-5, $Al_2O_3$ 504C), Amberlyst 15, $SiO_2$, TFA, Wayphos, polyphosphoric acid, Zeolite (CBV 21A sold by Zeolist, CBV 780 sold by Zeolist, CP814E sold by Zeolist), boric acid, $Al_2(SO_4)_3$, CSA, Pyridinium p-toluenesulfonate, $ZnBr_2$, K10-S300 (Bentonite) sold by Clariant, F24 X (Bentonite), Siral® 40 HPV sold by Sasol, HCl, HBr, $Zn(SO_4)_2$, $ZnCl_2$ $MgI_2$ and a mixture thereof.

The acid, used in the one pot elimination/isomerisation reaction, can be added into the reaction medium of the invention's process in a large range of concentrations. As non-limiting examples, one can cite as acid concentration values those ranging from about 1 mol % to about 20 mol %, relative to the amount of the of substrate, preferably from 2 mol % to about 10 mol %, relative to the amount of the of substrate, preferably from about 3 mol % to about 6 mol %, relative to the amount of the of substrate. The optimum concentration of the acid will depend, as the person skilled in the art knows, on the nature of the latter, on the nature of the substrate, on the reaction temperature as well as on the desired time of reaction.

According to any one of the invention's embodiments, the invention's process to form compound of formula (V) is carried out at a temperature comprised between RT and 160° C. In particular, the temperature is in the range between 90° C. and 140° C. Of course, a person skilled in the art is also able to select the preferred temperature as a function of the melting and boiling point of the starting and final products as well as the desired time of reaction or conversion.

The one pot elimination/isomerisation reaction can be carried out in the presence or absence of a solvent. When a solvent is required or used for practical reasons, then any solvent current in such reaction type can be used for the purposes of the invention. Non-limiting examples include $C_{6-12}$ aromatic solvents such as xylene, toluene, 1,3-diisopropylbenzene, cumene or pseudocumene, or mixtures thereof, hydrocarbon solvents such as cyclohexane, heptane or mixtures thereof, esteral or ethereal solvents such as butyl acetate, diisopropyl ether, dioxane, dimethoxyethane or a mixture thereof. The choice of the solvent is function of the nature of the substrate and/or catalyst and the person skilled in the art is well able to select the solvent most suitable in each case to optimize the reaction.

According to a particular embodiment, the protection, elimination and isomerization reactions may be carried out in one pot.

According to any embodiments of the invention, the deprotection of the acetal group to obtain compound of formula (I) may be carried out under normal condition known by the person skilled in the art, i.e. with a large molar excess of carboxylic acid in water. Specific and non-limiting examples of carboxylic acids may be selected from the group consisting of acetic acid, propionic acid, citric acid, formic acid, TFA, oxalic acid or a mixture thereof.

The carboxylic acid, used in the deprotection, can be added into the reaction medium of the invention's process in a large range of concentrations. As non-limiting examples, one can cite as acid concentration values those ranging from about 5 to about 20 equivalents, relative to the amount of the of substrate, preferably from 5 to about 10 equivalents, relative to the amount of the of substrate The optimum concentration of the acid will depend, as the person skilled in the art knows, on the nature of the latter, on the nature of the substrate, on the reaction temperature as well as on the desired time of reaction.

According to any one of the invention's embodiments, the deprotection to form compound of formula (I) may be carried out at a temperature comprised between 40° C. and 120° C. In particular, the temperature is in the range between 70° C. and 90° C. Of course, a person skilled in the art is also able to select the preferred temperature as a function of the melting and boiling point of the starting and final products as well as the desired time of reaction or conversion.

According to any one of the invention's embodiments, the deprotection to form compound of formula (I) can be carried out in the presence or absence of a solvent. When a solvent is required or used for practical reasons, then any solvent current in such reaction type can be used for the purposes of the invention. Non-limiting examples include $C_{6-12}$ aromatic solvents such as toluene, xylene, 1,3-diisopropylbenzene, cumene or pseudocumene, or mixtures thereof, alcoholic solvents such as methanol, ethanol, 2-methylbutan-2-ol or mixtures thereof, hydrocarbon solvents such as cyclohexane, heptane or mixtures thereof, esteric solvents such as n-butyl acetate, iso-propyl acetate, ethyl acetate or ethereal solvents such as methyl tetrahydrofuran, tetrahydrofuran or mixtures thereof. The choice of the solvent is a function of the nature of the substrate and of the carboxylic derivative and the person skilled in the art is well able to select the solvent most convenient in each case to optimize the reaction.

According to a particular embodiment, the protection, elimination, isomerization and deprotection reactions may be carried out in one pot.

According to a particular embodiment of the invention, the invention process comprises an elimination step followed by a hydroformylation starting from compound of formula (II). The invention's process comprises the step of a) the elimination of the OX' group of compound of formula (II")

(II")

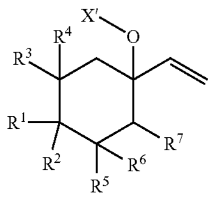

in the form of any one of its stereoisomers or a mixture thereof, wherein X' is a hydrogen atom, a $C_{1-3}$ alkyl group, a $C_{2-3}$ alkenyl group, a benzyl group or a C(O)R group or a $Si(R')_3$ group wherein R is a hydrogen atom, a $C_{1-4}$ alkyl group, a $C_{1-4}$ alkoxy group or a phenyl group, R', independently from each other, are a $C_{1-4}$ alkyl group; and wherein $R^1$, $R^2$, $R^3$, $R^4$, $R^5$, $R^6$ and $R^7$ have the same meaning as defined to obtain compound of formula (VI)

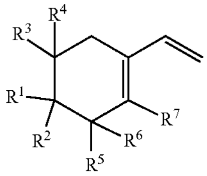

in the form of any one of its stereoisomers or a mixture thereof, and wherein $R^1$, $R^2$, $R^3$, $R^4$, $R^5$, $R^6$ and $R^7$ have the same meaning as defined above; and b) hydroformylation of compound of formula (VI) to obtain compound of formula (I).

The elimination and hydroformylation conditions are similar to those mentioned above. The elimination of the OX' group of compound of formula (II'), when X' is a hydrogen atom, may also be carried out in presence of phosphoryl chloride and an amine such as pyridine or in presence of mesyl chloride and triethylamine.

The invention's process for the preparation of a compound of formula (I) may be carried out under batch and/or continuous conditions. Particularly, the elimination step may be carried out under continuous conditions.

The compound of formula (II), (III), (IV) and (V') are, generally, novel compounds and present a number of advantages as explained above and shown in the Examples.

Therefore, another object of the present invention is a compound of formula (III)

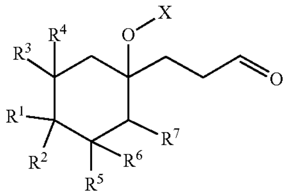

in the form of any one of its stereoisomers or a mixture thereof, and wherein X represents a C(O)R group or a $Si(R')_3$ group wherein R is a hydrogen atom, a $C_{1-4}$ alkyl group, a $C_{1-4}$ alkoxy group or a phenyl group, R', independently from each other, are a $C_{1-4}$ alkyl group; each $R^1$, $R^2$, $R^3$, $R^4$, $R^5$, $R^6$ and $R^7$, independently from each other, represent a hydrogen atom, a $C_{1-6}$ alkyl group or a $C_{2-6}$ alkenyl group, each optionally substituted by a hydroxy or $C_{1-3}$ alkoxy group; or two groups among $R^1$, $R^2$, $R^3$, $R^4$, $R^5$, $R^6$ and $R^7$ are taken together and form $C_{3-8}$ cycloalkyl or $C_{5-8}$ cycloalkenyl group and the others groups have the same meaning as defined above; provided that 1-(3-oxopropyl)cyclohexyl acetate is excluded.

Another object of the present invention is compound of formula (IV')

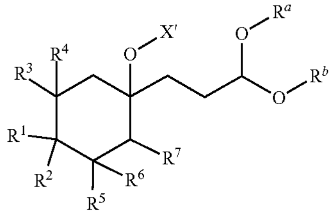

in the form of any one of its stereoisomers or a mixture thereof, and wherein X' is a hydrogen atom, a $C_{1-3}$ alkyl group, a $C_{2-3}$ alkenyl group, a benzyl group or a C(O)R group or a $Si(R')_3$ group wherein R is a hydrogen atom, a $C_{1-4}$ alkyl group, a $C_{1-4}$ alkoxy group or a phenyl group, R', independently from each other, are a $C_{1-4}$ alkyl group; each $R^1$, $R^2$, $R^3$, $R^4$, $R^5$, $R^6$ and $R^7$, independently from each other, represent a hydrogen atom, a $C_{1-6}$ alkyl group or a $C_{2-6}$ alkenyl group, each optionally substituted by a hydroxy or $C_{1-3}$ alkoxy group; or two groups among $R^1$, $R^2$, $R^3$, $R^4$, $R^5$, $R^6$ and $R^7$ are taken together and form $C_{3-8}$ cycloalkyl or $C_{5-8}$ cycloalkenyl group and the others groups have the same meaning as defined above; $R^a$ and $R^b$, independently from each other, represent a $C_{1-4}$ alkyl group or $R^a$ and $R^b$ are taken together and represent a $C_{2-6}$ alkanediyl group; provided that 1-(2-(1,3-dioxolan-2-yl)ethyl)-4-isobutyl-2-methylcyclohexan-1-ol, 1-(2-(1,3-dioxolan-2-yl)ethyl)-4-(tert-butyl)-2-methylcyclohexan-1-ol, 1-(2-(1,3-dioxolan-2-yl)ethyl)-4-isopropyl-2-methylcyclohexan-1-ol, 1-(3,3-diethoxypropyl)cyclohexan-1-ol, 1-(2-(1,3-dioxolan-2-yl)ethyl)-4-(tert-butyl)cyclohexan-1-ol and 1-(2-(1,3-dioxan-2-yl)ethyl)-4-(tert-butyl)cyclohexan-1-ol are excluded. Particularly, the compound of formula (IV') is of formula (IV)

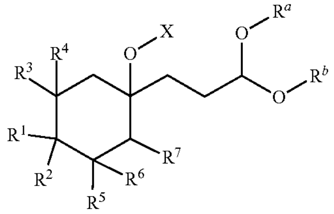

in the form of any one of its stereoisomers or a mixture thereof, and wherein X represents a C(O)R group or a $Si(R')_3$ group wherein R is a hydrogen atom, a $C_{1-4}$ alkyl group, a $C_{1-4}$ alkoxy group or a phenyl group, R', independently from each other, are a $C_{1-4}$ alkyl group; each $R^1$, $R^2$, $R^3$, $R^4$, $R^5$, $R^6$ and $R^7$, independently from each other, represent a hydrogen atom, a $C_{1-6}$ alkyl group or a $C_{2-6}$ alkenyl group, each optionally substituted by a hydroxy or $C_{1-3}$ alkoxy group; or two groups among $R^1$, $R^2$, $R^3$, $R^4$, $R^5$, $R^6$ and $R^7$ are taken together and form $C_{3-8}$ cycloalkyl or $C_{5-8}$ cycloalkenyl group and the others groups have the same meaning as defined above; $R^a$ and $R^b$, independently from each other, represent a $C_{1-4}$ alkyl group or $R^a$ and $R^b$ are taken together and represent a $C_{2-6}$ alkanediyl group.

Another object of the present invention is a compound of formula (V')

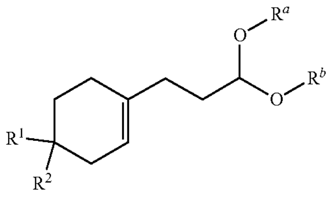

in the form of any one of its stereoisomers or a mixture thereof, and wherein; each $R^1$ and $R^2$, independently from each other, represent a hydrogen atom, a $C_{1-6}$ alkyl group or a $C_{2-6}$ alkenyl group, each optionally substituted by a hydroxy or $C_{1-3}$ alkoxy group; $R^a$ and $R^b$, independently from each other, represent a $C_{1-4}$ alkyl group or $R^a$ and $R^b$ are taken together and represent a $C_{2-6}$ alkanediyl group.

Another object of the present invention is a process for the preparation of a compound of formula (II)

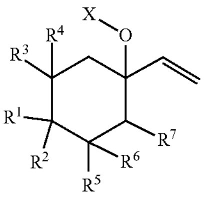

in the form of any one of its stereoisomers or a mixture thereof, and wherein wherein X represents a C(O)R group or a $Si(R')_3$ group wherein R is a hydrogen atom, a $C_{1-4}$ alkyl group, a $C_{1-4}$ alkoxy group or a phenyl group, R', independently from each other, are a $C_{1-4}$ alkyl group; each $R^1$, $R^2$, $R^3$, $R^4$, $R^5$, $R^6$ and $R^7$, independently from each other, represent a hydrogen atom, a $C_{1-6}$ alkyl group or a $C_{2-6}$ alkenyl group, each optionally substituted by a hydroxy or $C_{1-3}$ alkoxy group; or two groups among $R^1$, $R^2$, $R^3$, $R^4$, $R^5$, $R^6$ and $R^7$ are taken together and form $C_{3-8}$ cycloalkyl or $C_{5-8}$ cycloalkenyl group and the others groups have the same meaning as defined above;

comprising the step of reducing compound of formula (VII)

(VII)

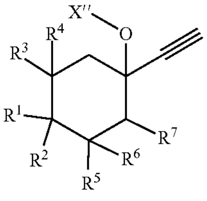

in the form of any one of its stereoisomers or a mixture thereof, wherein X" is a hydrogen atom, a C(O)R group or a $Si(R')_3$ group wherein R is a hydrogen atom, a $C_{1-4}$ alkyl group, a $C_{1-4}$ alkoxy group or a phenyl group, R', independently from each other, are a $C_{1-4}$ alkyl group; and wherein $R^1$, $R^2$, $R^3$, $R^4$, $R^5$, $R^6$ and $R^7$ have the same meaning as defined.

According to a particular embodiment, the invention's process comprises the steps of a) the reduction of compound of formula (VII')

(VII')

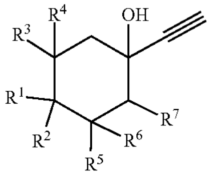

in the form of any one of its stereoisomers or a mixture thereof, wherein $R^1$, $R^2$, $R^3$, $R^4$, $R^5$, $R^6$ and $R^7$ have the same meaning as defined above;

into compound of formula (II''')

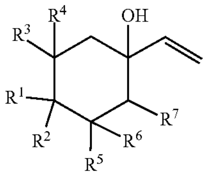

in the form of any one of its stereoisomers or a mixture thereof, wherein $R^1$, $R^2$, $R^3$, $R^4$, $R^5$, $R^6$ and $R^7$ have the same meaning as defined above; and b) the protection of compound (II''') to obtain compound of formula (II).

According to another particular embodiment, the invention's process comprises the steps of a) protecting compound of formula (VII')

(VII')

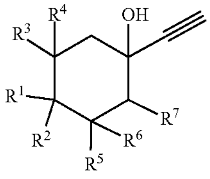

in the form of any one of its stereoisomers or a mixture thereof, wherein $R^1$, $R^2$, $R^3$, $R^4$, $R^5$, $R^6$ and $R^7$ have the same meaning as defined above;

into compound of formula (VII'')

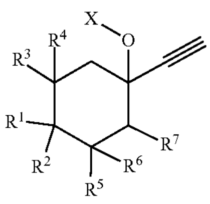

in the form of any one of its stereoisomers or a mixture thereof, wherein $R^1$, $R^2$, $R^3$, $R^4$, $R^5$, $R^6$ and $R^7$ have the same meaning as defined above; and X represents a C(O)R group or a $Si(R')_3$ group wherein R is a hydrogen atom, a $C_{1-4}$ alkyl group, a $C_{1-4}$ alkoxy group or a phenyl group, R', independently from each other, are a $C_{1-4}$ alkyl group; and b) the reduction of compound (VII") to obtain compound of formula (II).

For the sake of clarity, by the expression "wherein the dotted line represents a double or a triple bond", or the similar, it is meant the normal meaning understood by a person skilled in the art, i.e. that the whole bonding (solid and dotted line) between the carbon atoms connected by said dotted line, is a carbon-carbon double or a carbon-carbon triple bond.

According to any embodiment of the invention, the reduction is a hydrogenation. Particularly, the hydrogenation may be carried out in a presence of heterogeneous catalyst such as palladium in elemental metallic form. Particularly, said palladium may be supported on a carrying material. For the sake of clarity, by carrying material it is intended a material wherein it is possible to deposit such metal and which is inert toward the hydrogen source and the substrate. The supported palladium are known compounds and are commercially available. A person skilled in the art is able to select the way that it was deposit on the support, as the proportion of metal on support material, as the form (powder, granules, pellets, extrudates, mousses . . . ) and as the surface area of the support.

Particularly, the heterogeneous catalyst may be a Lindlar catalyst, palladium on Charcoal powder (know with the trademark Nanoselect™ LF 100, origin: BASF) or palladium on titanium silicate powder (know with the trademark Nanoselect™ LF 200, origin: BASF). The hydrogenation may be carried out under normal condition known by the person skilled in the art who will be able to set up the best conditions in order to convert compound of formula (VII') to compound of formula (II'") or in order to convert compound of formula (VII") into compound of formula (II).

The reduction may be carried out in the presence of additive such as 3,6-dithia-1,8-octanediol.

Palladium can be added into the reaction medium of the invention's process in a large range of concentrations. As non-limiting examples, one can cite as palladium concentration values those ranging from about 0.005 mol % to about 10 mol %, relative to the amount of the of substrate, preferably from 0.01 mol % to about 1 mol %, relative to the amount of the of substrate, preferably from about 0.01 mol % to about 0.2 mol %, relative to the amount of the of substrate, preferably from about 0.03 mol % to about 0.1 mol %, relative to the amount of the of substrate. The optimum concentration of the palladium will depend, as the person skilled in the art knows, on the nature of the latter, on the nature of the substrate, on the nature of the catalyst, on the reaction temperature as well as on the desired time of reaction.

The additive, such as 3,6-dithia-1,8-octanediol, can be added into the reaction medium of the invention's process in a large range of concentrations. As non-limiting examples, one can cite as additive concentration values from about 1 mol. % to 50 mol. % relative to the amount of palladium, preferably from 5 mol. % to 50 mol. % relative to the amount of palladium, preferably from 5 mol. % to 40 mol. % relative to the amount of palladium, preferably from 5 mol. % to 25 mol. % relative to the amount of palladium. The optimum concentration of the additive will depend, as the person skilled in the art knows, on the nature of the latter, on the nature of the substrate, on the nature of the catalyst, on the reaction temperature as well as on the desired time of reaction.

The hydrogenation can be carried out at a $H_2$ pressure comprised between 104 Pa and $3\times10^5$ Pa (0.1 to 3 bars). Particularly, the hydrogenation can be carried out at a $H_2$ pressure comprised between $3\times10^4$ Pa and 10W Pa (0.3 to 1 bars). Again, a person skilled in the art is well able to adjust the pressure as a function of the catalyst load.

According to any one of the invention's embodiments, the hydrogenation is carried out at a temperature comprised between 10° C. and 50° C. In particular, the temperature is in the range between 20° C. and 35° C. Of course, a person skilled in the art is also able to select the preferred temperature as a function of the melting and boiling point of the starting and final products as well as the desired time of reaction or conversion.

The hydrogenation can be carried out in the presence or absence of a solvent. When a solvent is required or used for practical reasons, then any solvent current in such reaction type can be used for the purposes of the invention. Non-limiting examples include $C_{6-12}$ aromatic solvents such as xylene, toluene, 1,3-diisopropylbenzene, cumene or pseudocumene, or mixtures thereof, hydrocarbon solvents such as cyclohexane, heptane or mixtures thereof, alcoholic solvents such as methanol, ethanol, 2-methylbutan-2-ol or mixtures thereof, ketone solvent such as acetone, acetophenone, butanone, cyclopentanone or mixtures thereof, etheral solvent such as diethyl ether, tert-butyl methyl ether, tetrahydrofuran, methyl tetrahydrofuran or a mixture thereof, esteral solvent such as ethyl acetate, isopropyl acetate or mixtures thereof. The choice of the solvent is function of the nature of the substrate and/or catalyst and the person skilled in the art is well able to select the solvent most suitable in each case to optimize the reaction.

According to any embodiment of the invention, the protection step may depend on the nature of the X group. The person skilled in the art is well aware of the conditions to apply in order to protect the alcohol in the form of an ester, X being C(O)R, or in the form of a silane, X being $Si(R')_3$ group. Typical conditions may be found in abundant literature in organic chemistry filed such as Protective Groups in Organic Synthesis, 3rd Edition. Theodora W. Green (The Rowland Institute for Science) and Peter G. M. Wuts (Pharmacia and Upjohn Company). John Wiley & Sons, Inc., New York, NY. 1999. xxi+779 pp. 15.5×23 cm. ISBN 0-471-16019-9.

According to any embodiment of the invention, the compound of formula (VII') may be prepared by an ethynylation reaction of ketone of formula (VIII)

(VIII)

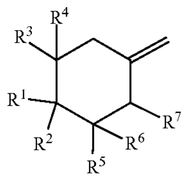

in the form of any one of its stereoisomers or a mixture thereof, and wherein each $R^1$, $R^2$, $R^3$, $R^4$, $R^5$, $R^6$ and $R^7$, independently from each other, represent a hydrogen atom, a $C_{1-6}$ alkyl group or a $C_{2-6}$ alkenyl group, each optionally substituted by a hydroxy or $C_{1-3}$ alkoxy group; or two groups among $R^1$, $R^2$, $R^3$, $R^4$, $R^5$, $R^6$ and $R^7$ are taken together and form $C_{3-8}$ cycloalkyl or $C_{5-8}$ cycloalkenyl group and the others groups have the same meaning as defined above. The person skilled in the art is well aware of the conditions to apply in order to obtain compound (VII') starting from compound (VIII). This kind of reaction has been largely reported in the prior art. So, the person skilled in the art will be able to set up the best conditions in order to convert compound of formula (VIII) into compound of formula (VII'). As non-limiting example, said reaction may be performed under the conditions reported in Angewandte Chemie, International Edition, 2020, 1666-1673, WO2009126584 or WO2014056851.

Another object of the present invention is a compound of formula (IX)

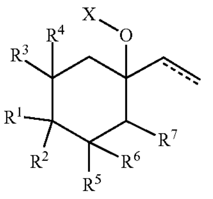

in the form of any one of its stereoisomers or a mixture thereof, and wherein the dotted line represents a double or a triple bond; X represents a C(O)R group or a $Si(R')_3$ group wherein R is a hydrogen atom, a $C_{1-4}$ alkyl group, a $C_{1-4}$ alkoxy group or a phenyl group, R', independently from each other, are a $C_{1-4}$ alkyl group; each $R^1$, $R^2$, $R^3$, $R^4$, $R^5$, $R^6$ and $R^7$, independently from each other, represent a hydrogen atom, a $C_{1-6}$ alkyl group or a $C_{2-6}$ alkenyl group, each optionally substituted by a hydroxy or $C_{1-3}$ alkoxy group; or two groups among $R^1$, $R^2$, $R^3$, $R^4$, $R^5$, $R^6$ and $R^7$ are taken together and form $C_{3-8}$ cycloalkyl or $C_{5-8}$ cycloalkenyl group and the others groups have the same meaning as defined above; provided that 1-vinylcyclohexyl acetate, 1-ethynylcyclohexyl acetate, 1-vinylcyclohexyl propionate, 4-methyl-1-vinylcyclohexyl acetate, 2-methyl-1-vinylcyclohexyl acetate, 1-ethynyl-2-methylcyclohexyl acetate, 2-ethyl-1-vinylcyclohexyl acetate, 2-isopropyl-1-vinylcyclohexyl acetate, 2-secbutyl-1-vinylcyclohexyl acetate, 2-isopropyl-5-methyl-1-vinylcyclohexyl acetate, 2-allyl-1-vinylcyclohexyl acetate, 4-tert-butyl-1-vinylcyclohexyl acetate, 1-vinyldecahydronaphthalen-1-yl acetate and 1-ethynyldecahydronaphthalen-1-yl acetate are excluded.

Herein disclosed is a process for the preparation of a compound of formula (X)

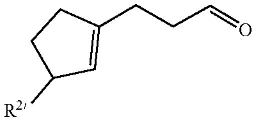

in the form of any one of its stereoisomers or a mixture thereof, and wherein each $R^{2'}$ represents a $C_{1-4}$ alkyl group;

comprising a hydroformylation and an elimination step starting from compound of formula (II)

(XI)

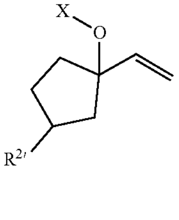

in the form of any one no its stereoisomers or a mixture thereof, and wherein $R^{2'}$ has the same meaning as defined in formula (I) and X represents a C(O)R group or a $Si(R')_3$ group wherein R is a hydrogen atom, a $C_{1-4}$ alkyl group, a $C_{1-4}$ alkoxy group or a phenyl group, R', independently from each other, are a $C_{1-4}$ alkyl group.

The process for preparing compound (X) is performed according to the same embodiments than compound the process for the preparation of compound of formula (I).

Typical manners to execute the invention's process are reported herein below in the examples.

EXAMPLES

The invention will now be described in further detail by way of the following examples, wherein the abbreviations have the usual meaning in the art, the temperatures are indicated in degrees centigrade (° C.). The preparation of precatalysts and ligands solutions were carried out under an inert atmosphere (Argon) using standard Schlenk techniques. The solvents were dried by conventional procedures and distilled under an argon atmosphere. NMR spectra were recorded at 20° C. on Bruker AV 300, AV 400, or AV 500 MHz spectrometers. Chemical shifts are reported in ppm relative to solvent signals (chloroform, $\delta_H$=7.26 ppm, $\delta_C$=77.0 ppm). The signal assignment was ensured by recording $^1H,^1H$-COSY, -NOESY, $^{13}C,^1H$-HSQC and -HMBC experiments. Gas chromatography was performed on an Agilent 7890 A Series equipped with a HP5 column (30 m×0.25 mm ID, 0.25 μm film) and tetradecane was used as internal standard.

Example 1

Preparation of 4,4-dimethyl-1-vinylcyclohexyl acetate Via Hydrogenation Followed by a Esterification a) Step 1: Preparation of 1-vinyl-4,4-dimethylcyclohexanol 1-ethynyl-4,4-dimethylcyclohexanol (CAS number: 68483-62-5), acetone (100 wt. %), Lindlar catalyst (0.5 wt. %, 0.036 mol. % Pd) and 3,6-dithia-1,8-octanediol (Lindlar catalyst poison, CAS number: 5244-34-8) (0.005 wt. %, 12 mol. % respect to Pd) were loaded altogether in an 100 mL or IL autoclave equipped with a mechanical stirring device, pressure and internal temperature sensors and a heating/cooling system for internal temperature regulation. Sealed autoclave was then purged under stirring with nitrogen (3 times 5 bars) before being stirred at 25° C. under 1 bar nitrogen pressure for 30 minutes. After this period, autoclave was purged under stirring with hydrogen (3 times 1 bar) before being pressurized to 1 bar hydrogen pressure via a hydrogen tank equipped with a way out pressure regulator and also an internal pressure sensor to follow and determine hydrogen consumption. The reaction mixture was then stirred (1000 rnd./min) at 25° C. under 1 bar hydrogen pressure, pressure being maintained to this value during the whole reaction. Right upon alkyne hydrogenation completion (2 to 3 hours) also determined by GC analysis on a short polar column (DB-Wax 10 m×0.1 mm×0.1 μm), stirring was stopped, the autoclave was depressurized and purged with nitrogen (3 times 5 bars). The reaction mixture was passed through some filtration equipment to remove Lindlar catalyst and transferred to a round-bottomed flask for solvent removal under vacuum. The desired 1-vinyl-4,4-dimethyl-cyclohexanol was obtained with more than 99.5% GC conversion in 93-95% GC purity and no residues were formed (determined by sample bulb to bulb distillation).

$^1$H-NMR analysis results in $CDCl_3$ were in accordance with data from literature (see *Angew. Chem. Int. Ed.* 2009, 48, 3146-3149)

$^{13}$C NMR (90 MHz, $CDCl_3$): δ 25.5, 29.4, 30.9, 33.7, 34.7, 71.5, 111.6, 146.1.

b) Step 2: Preparation of 4,4-dimethyl-1-vinylcyclohexyl acetate

To a stirred solution of 4,4-dimethyl-1-vinyl-cyclohexanol (13.6 g 96% purity, 84.8 mmol) and Acetic anhydride (26.77 g 254.3 mmol) in Toluene (30 mL) was added DMAP (104 mg, 0.85 mmol, 1 mol %) and triethylamine (8.6 g, 84.8 mmol) under $N_2$. The mixture was heated at 90° C. After 5 h, DMAP (104 mg, 0.85 mmol, 1 mol %) was added and the mixture was further stirred for another 5 h. The mixture was cooled with a cold-water bath (10° C.) and 30 mL of water were added slowly (hydrolysis of residual $Ac_2O$). After stirring for 30 min, 50 mL of diethyl ether were added. The phases were separated, and the organic phase was washed once with a 1M aqueous HCl solution (40 mL), then washed once with water (50 mL), and then twice with a saturated aqueous $NaHCO_3$ solution (50 mL). After a final wash with brine the organic phase was dried over sodium sulfate, filtered and evaporated under reduced pressure (45° C., 30 mbar). The crude was purified by flash chromatography (330 g $SiO_2$, eluent from cyclohexane 95/diisopropylether 5 to cyclohexane 9/AcOEt 1). 4,4-dimethyl-1-vinylcyclohexyl acetate was isolated (14.93 g, purity 97%, 78.4 mmol, yield 92.5%) as a colourless liquid (volatile).

$^1$H-NMR (300 MHz): 0.90, 0.94 (2×s, 6H, 4-$(CH_3)_2$), 1.19-1.27 (m, 2H, H-3a, H-5a), 1.36-1.45 (m, 2H, H-3b, H-5b), 1.62-1.72 (m, 2H, H-2a, H-6a), 2.0 (s, 1H, $COCH_3$), 2.05-2.14 (m, 2H, H-2b, H-6b), 5.12 (dd, 1H, $^2J_{2'a,2'b}$=0.9 Hz; $^3J_{1',2'a}$=11.0 Hz, H-2'a), 5.17 (dd, 1H, $^2J_{2'a,2'b}$=0.9 Hz; $^3J_{1',2'b}$=17.7 Hz, H-2'b), 6.11 (dd, 1H, $^3J_{1',2'a}$=11.0 Hz, $^3J_{1',2'b}$=17.7 Hz, H-1').

$^{13}$C-NMR (100.61 MHz): 22.1 ($COCH_3$), 25.6, 31.0 ($(CH_3)_2$), 29.3 (C-4), 30.8 (C-2, C-6), 34.7 (C-3, C-5), 81.6 (C-1), 113.6 (C-2'), 141.7 (C-1'), 169.9 (C═O).

Example 2

Preparation of 4,4-dimethyl-1-vinylcyclohexyl acetate Via Esterification Followed by a Hydrogenation a) Step 1: Preparation of 1-ethynyl-4,4-dimethylcyclohexyl acetate 1-ethynyl-4,4-dimethylcyclohexanol (CAS number: 68483-62-5), acetonitrile (100 wt. %) and acetic anhydride (1.3 equivalents) were loaded altogether in a round-bottomed flask equipped with a magnetic stirring bar and an internal temperature sensor. Reaction mixture was cooled down to 3° C. and solid Iron (III) p-toluenesulfonate hexahydrate (CAS number: 312619-41-3) (2 mol. %) was added portionwise in order to maintain temperature below 10° C. Reaction was followed by GC analysis on a short apolar column (DB-1 10m×0.1 mm×0.1 μm) and complete conversion was achieved in 3 hours under such conditions and crude product was obtained with 98% GC selectivity. Reaction mixture was warmed up to room temperature and light compounds were removed under vacuum. Et2O (160 wt. %) was added to concentrated crude product and solution was washed with 10% aqueous $Na_2CO_3$, water, 1% aqueous $H_2SO_4$ and water. After drying on $Na_2SO_4$, Et20 was removed under vacuum. Product was purified by flash distilled in the presence of Primol™ 352 as a ballast before further final light compounds removal by fractional distillation to afford desired pure 1-ethynyl-4,4-dimethylcyclohexyl acetate in 90% molar yield.

$^1$H NMR (500 MHz, $CDCl_3$): δ (ppm) 0.93 (s, 3H, $CH_3$), 0.95 (s, 3H, $CH_3$), 1.33-1.41 (m, 2H, $CH_2$), 1.42-1.52 (m, 2H, $CH_2$), 1.90-2.02 (m, 2H, $CH_2$), 2.02-2.14 (m, 5H, $CH_2$+$CH_3$), 2.58 (s, 1H, CH).

$^{13}$C NMR (125 MHz, $CDCl_3$): δ (ppm) 21.9 ($CH_3$), 27.2 (broad signal, $CH_3$), 29.1 (broad signal, $CH_3$), 29.3 (C), 32.8 ($CH_2$), 35.1 ($CH_2$), 73.9 (CH), 75.1 (C), 83.5 (C), 169.3 (CO).

b) Step 2: Preparation of 4,4-dimethyl-1-vinylcyclohexyl acetate 1-ethynyl-4,4-dimethylcyclohexyl acetate (unknown compound), acetone (100 wt. %), Lindlar catalyst (0.75 wt. %, 0.068 mol. % Pd) and 3,6-dithia-1,8-octanediol (Lindlar catalyst poison, CAS number: 5244-34-8) (0.00765 wt. %, 12 mol. % respect to Pd) were loaded altogether in an 100 mL or IL autoclave equipped with a mechanical sitting device, pressure and internal temperature sensors and a heating/cooling system for internal temperature regulation. The sealed autoclave was then purged under stirring with nitrogen (3 times 5 bars) before being stirred at 25° C. under 1 bar nitrogen pressure for 30 minutes. After this period, the autoclave was purged under stirring with hydrogen (3 times 1 bar) before being pressurized to 1 bar hydrogen pressure via an hydrogen tank equipped with a way out pressure regulator and also and internal pressure sensor to follow and determine hydrogen consumption. The reaction mixture was then stirred (1000 rnd./min) at 25° C. under 1 bar hydrogen pressure, pressure being maintained to this value during the whole reaction. Upon alkyne hydrogenation completion (5 to 7 hours) also determined by GC analysis on a short polar column (DB-Wax 10m×0.1 mm×0.1 μm), stirring was stopped, and the autoclave was depressurized and purged with nitrogen (3 times 5 bars). The reaction mixture was passed through some filtration equipment to remove the Lindlar catalyst and transferred to a round-bottomed flask for solvent removal under vacuum. The desired 4,4-dimethyl-1-vinylcyclohexyl acetate was obtained with more than complete GC conversion in 97.5% GC purity and no residues were formed (determined by sample bulb to bulb distillation).

Example 3

Preparation of 4,4-dimethyl-1-vinylcyclohex-1-ene 46.5 g (99.1% purity, 234.8 mmol of 4,4-dimethyl-1-vinylcyclohexyl acetate were added slowly (12 mL/h) from the top and under a $N_2$ flow to a heated pyrolysis column (pyrolysis oven at 500° C.), which was filled with 20 g quartz cylinder. When the addition was finished, the oven was cooled down. When 50° C. oven temperature were reached, the crude was transferred into a separation funnel and 50 mL of pentane were added. The mixture was washed twice with 50 mL of water and once with 100 mL of a saturated aqueous $NaHCO_3$ solution. The organic phase was dried over sodium sulfate and pentane was evaporated carefully (900 mbar, bath temperature of Rotavap from 40 to 80° C.). 35.1 g of a yellow liquid were obtained (conversion 99%, GC 98.1% purity). The crude was distilled (vigreux column, 50-20 mbar, bp 76° C.) and 29.23 g (99.0% purity, 232.42 mmol, 90.5% yield) of the volatile 4,4-dimethyl-1-vinylcyclohex-1-ene were obtained. $^1$H and analysis results in $CDCl_3$ were in accordance data from literature (see *Angew. Chem. Int. Ed.* 2009, 48, 3146-3149)

$^{13}$C NMR (90 MHz, $CDCl_3$): δ 21.6, 28.2, 29.0, 35.2, 39.8, 109.7, 128.8, 134.8, 139.9.

Example 4

Hydroformylation of 4,4-dimethyl-1-vinylcyclohexyl acetate 4,4-dimethyl-1-vinylcyclohexyl acetate (196 mg, 1.0 mmol), Ligand (3.5 mM in EtOAc, 2.0 mL) and Rh(acac)$(CO)_2$ (1.0 mM in EtOAc, 1.43 mL) were added to an autoclave (HEL 20 mL/200 bar). The autoclave was purged 3 times with 8 bar Argon and 4 times with 10 bar syngas ($H_2$:CO, 1:1) under stirring (500 rpm). The autoclave was then charged with 10 bar syngas and the reaction mixture was heated until the temperature reached 75° C. The autoclave was then further pressurized with syngas to 40 bar, the stirring rate adjusted at 900 rpm and the temperature was set to 80° C. The hydroformylation was continued compensating the gas uptake with $H_2$:CO (1:1). After 22 h the reaction mixture was cooled to room temperature, the pressure released, and the autoclave was purged 5 times with 12 bar Argon. The product analysis was performed by gas chromatography using tetradecane as internal standard.

The results obtained are shown in Table 1.

TABLE 1

Hydroformylation of 4,4-dimethyl-1-vinylcyclohexyl acetate catalysed by rhodium complexes with different ligands.

| Entry | Ligand | L/Rh | Conversion [1)] | Selectivity [1)] (1/2) | Yield [1)] (1) |
|---|---|---|---|---|---|
| 1 | Xantphos | 5 | 41% | 99/1 | 41% |
| 2 | Nixantphos | 5 | 46% | 99/1 | 46% |
| 3 | BISBI | 5 | 32% | 86/7 | 28% |
| 4 | BIPHEPHOS | 5 | 100% | 98/0.3 | 98% |
| 5 | DPEphos | 5 | 30% | 92/5 | 28% |

[1)] determined by GC; 1 being 4,4-dimethyl-1-(3-oxopropyl)cyclohexyl acetate and 2 being 4,4-dimethyl-1-(1-oxopropan-2-yl)cyclohexyl acetate 4,4-dimethyl-1-(3-oxopropyl)cyclohexyl acetate (1)

$^1$H-NMR (300 MHz): 0.86, 0.90 (2×s, 6H, 4-$(CH_3)_2$), 1.14-1.21 (m, 2H, H-3a, H-5a) 1.27-1.47 (m, 4H, H-3b, H-5b, H-2a, H-6a); 2.0 (s, 3H, $COCH_3$), 2.03-2.11 (m, 2H, H-2b, H-6b), 2.18-2.23 (m, 2H, H-3'), 2.37-2.43 (m, 2H, H-2'), 9.72 (t, 1H, $^3J_{1',2'}$=1.7 Hz, H-1').

$^{13}$C-NMR (100.61 MHz): 22.0 ($CH_3CO$), 25.3, 31.0 ($(CH_3)_2$), 29.3 (C-3'), 29.3 (C-4), 30.4 (C-2, C-6), 34.5 (C-3, C-5), 38.2 (C-2'), 82.6 (C-1), 170.3 ($COCH_3$), 201.8 (C-1').

4,4-dimethyl-1-(1-oxopropan-2-yl)cyclohexyl acetate (2)

$^1$H-NMR (500 MHz): 0.86, 0.89 (2×s, 6H, 4-$(CH_3)_2$), 1.03 (d, 3H, $^3J_{2',3'}$=7.1 Hz, 3'-$CH_3$), 1.17-1.23 (*, 2H, H-3a, H-5a), 1.31-1.43 (*, 2H, H-3b, H-5b), 1.54, 1.63 (2×ddd, 1H, $^3J_{2a,3b}$=$^3J_{6a,5b}$=4.0 Hz, $^3J_{2a,3a}$=$^3J_{5a,6a}$=13.0 Hz, $^2J_{2a,2b}$=$^2J_{6a,6b}$=14.0 Hz, H-2a', H-6a'), 2.0 (s, 1H, $COCH_3$), 2.04-2.09, 2.17-2.21 (*, 2H, H-2b, H-6b), 3.22 (dq, 1H, $^3J_{1',2'}$=1.6 Hz, $^3J_{2',3'}$=7.1 Hz, H-2'); 9.73 (d, 1H, $^3J_{1',2'}$=1.64 Hz, H-1'). *under signals of main product.

$^{13}$C-NMR (125.76 MHz): 8.5 (3'-$CH_3$), 21.7 ($CH_3CO$), 24.2, 32.0 ($(CH_3)_2$), 29.2 (C-4); 27.1, 28.9 (C-2, C-6), 34.1, 34.2 (C-3, C-5), 51.5 (C-2'), 83.7 (C-1), 170.4 ($COCH_3$), 202.3 (C-1').

Example 5

Hydroformylation of 4,4-dimethyl-1-vinylcyclohexyl acetate with Xantphos-Rh Catalyst a) General Procedure:

4,4-dimethyl-1-vinylcyclohexyl acetate (589 mg, 3.0 mmol), Xantphos (i.e. (9,9-dimethyl-9H-xanthene-4,5-diyl) bis(diphenylphosphine) (in EtOAc) and Rh(acac)$(CO)_2$ (in EtOAc) were added to an autoclave (HEL 20 mL/200 bar) according to Table 2. The autoclave was purged 3 times with 8 bar Argon and 4 times with 10 bar syngas ($H_2$:CO, 1:1) under stirring (500 rpm). The autoclave was then charged with 10 bar syngas and the reaction mixture was heated until the temperature reached 75° C. The autoclave was then further pressurized with syngas to 40 bar, the stirring rate adjusted at 900 rpm and the temperature was set to 80° C. The hydroformylation was continued compensating the gas uptake with $H_2$:CO (1:1). After the reaction time indicated in Table 2, the reaction mixture was cooled to room temperature, the pressure released, and the autoclave was purged 5 times with 12 bar Argon. Product analysis was performed by gas chromatography using tetradecane as internal standard.

The results obtained are shown in Table 2.

TABLE 2

Hydroformylation of 4,4-dimethyl-1-vinylcyclohexyl acetate catalysed by Xantphos-Rh catalyst at different catalyst loadings.

| Entry | Rh:L:S | V (solvent) | Reaction time | Conversion [1)] | Selectivity [1)] (1/2) | Yield [1)] (1) |
|---|---|---|---|---|---|---|
| 1 | 1:5:2 000 | 1.5 mL | 42 h | 85% | 99/0.9 | 84% |
| 2 | 1:5:4 000 | 1.0 mL | 72 h | 85% | 99/0.9 | 84% |

[1)] determined by GC; 1 being 4,4-dimethyl-1-(3-oxopropyl)cyclohexyl acetate and 2 being 4,4-dimethyl-1-(1-oxopropan-2-yl)cyclohexyl acetate Example 6

Hydroformylation of 4,4-dimethyl-1-vinylcyclohexyl acetate with BIPHEPHOS-Rh Catalyst a) General Procedure:

4,4-dimethyl-1-vinylcyclohexyl acetate (785 mg, 4.0 mmol), BIPHEPHOS (i.e. 6,6'-[(3,3'-Di-tert-butyl-5,5'-dimethoxy-1,1'-biphenyl-2,2'-diyl)bis(oxy)]bis(dibenzo[d,f][1,3,2]dioxaphosphepin)) (in EtOAc) and $Rh(acac)(CO)_2$ (in EtOAc) were added to an autoclave (HEL 20 mL/200 bar) according to Table 2. The autoclave was purged 3 times with 8 bar Argon and 4 times with 10 bar syngas ($H_2$:CO, 1:1) under stirring (500 rpm). The autoclave was then charged with 10 bar syngas and the reaction mixture was heated until the temperature reached 85° C. The autoclave was then further pressurized with syngas to 40 bar, the stirring rate adjusted at 900 rpm and the temperature was set to 90° C. The hydroformylation was continued compensating the gas uptake with $H_2$:CO (1:1). After the reaction time indicated in Table 2, the reaction mixture was cooled to room temperature, the pressure released, and the autoclave was purged 5 times with 12 bar Argon. Product analysis was performed by gas chromatography using tetradecane as internal standard.

The results obtained are shown in Table 3.

TABLE 3

Hydroformylation of 4,4-dimethyl-1-vinylcyclohexyl acetate catalyzed by BIPHEPHOS-Rh catalyst at different catalyst loadings.

| Entry | Rh:L:S | V (solvent) | Reaction time | Conversion [1] | Selectivity [1] (1/2) | Yield [1] (1) |
|---|---|---|---|---|---|---|
| 1 | 1:5:700 | 14 mL | 22 h | 100% | 98/0.3 | 98% |
| 2 | 1:5:700 | 9.6 mL | 7 h | 100% | 97/0.3 | 97% |
| 3 | 1:5:2 000 | 9.6 mL | 18 h | 99% | 98/0.2 | 97% |
| 4 | 1:5:2 000 | 4.0 mL | 18 h | 100% | 97/0.1 | 97% |
| 5 | 1:5:2 000 | 1.2 mL | 3.5 h | 100% | 96/0.1 | 96% |
| 6 | 1:5:4 000 | 1.2 mL | 12 h | 98% | >99/0.1 | 97% |
| 7 | 1:5:8 000 | 1.2 mL | 12 h | 97% | >99/0.2 | >96% |
| 8 | 1:5:20 000 | 1.2 mL | 22 h | 97% | 94/0.2 | 91% |
| 9 | 1:2.5:20 000 | 1.2 mL | 22 h | 96% | 98/0.2 | 94% |
| 10 | 1:2.5:20 000 | 0.4 mL | 22 h | 97% | >99/0.2 | >96% |
| 11 | 1:2:40 000 | 0.4 mL | 22 h | 97% | 97/0.2 | 94% |
| 12 | 1:2:80 000 | 0.4 mL | 22 h | 87% | 98/0.2 | 85% |
| 13 | 1:2:80 000 | 0.2 mL | 22 h | 86% | 99/0.2 | 85% |
| 14 | 1:2:80 000 | 0.2 mL | 36 h | 97% | >99/— | >96% |
| 15[2] | 1:2:80 000 | 0.2 mL | 36 h | 97% | >99/— | >96% |

[1] determined by GC; 1 being 4,4-dimethyl-1-(3-oxopropyl)cyclohexyl acetate and 2 being 4,4-dimethyl-1-(1-oxopropan-2-yl)cyclohexyl acetate

[2] $H_2$:CO (2:1)

Example 7

Hydroformylation of 4,4-dimethyl-1-vinylcyclohexyl acetate with BIPHEPHOS-Rh (Upscaling)

$Rh(CO)_2acac$ (6.0 mM in EtOAc, 16.4 mL), BIPHEPHOS (15 mM in EtOAc, 33 mL), 4,4-dimethyl-1-vinylcyclohexyl acetate (39.0 g, 98.9% purity, 196.5 mmol) and ethyl acetate (3 mL) were added to an autoclave (Premex 150 mL/200 bar) kept under Argon. The autoclave was charged with 10 bar syngas ($H_2$:CO, 1:1) and the reaction mixture was heated under vigorous stirring until the temperature reached 90° C. The autoclave was then further pressurized with syngas to 42 bar and the hydroformylation was continued compensating the gas uptake with $H_2$:CO (1:1). After 3.5 h the reaction mixture was cooled to room temperature, the pressure released and the autoclave was purged with Ar. The mixture (94.8 g, GC 98% linear aldehyde 1, <0.1% branched aldehyde 2), yield 97%. Selectivity branched/linear 1/2>98/0.1) was filtered and the solvent was evaporated under reduced pressure (150 mbar, 45° C.). After addition of 90 mL heptane and solvent evaporation (20 mbar, 45° C.) we could isolate 45.1 g (94.2% purity, 187.7 mmol, 95.5% yield) of 4,4-dimethyl-1-(3-oxopropyl)cyclohexyl acetate as a yellow liquid.

Example 8

Hydroformylation of 4,4-dimethyl-1-vinylcyclohexyl acetate with BIPHEPHOS Analogs-Rh Catalysts 4,4-dimethyl-1-vinylcyclohexyl acetate (491 mg, 2.5 mmol), Ligand (1.0 mM in EtOAc, 0.25 mL), $Rh(acac)(CO)_2$ (0.5 mM in EtOAc, 0.25 mL) and EtOAc (0.34 mL) were added to an autoclave (HEL 20 mL/200 bar). The autoclave was purged 3 times with 8 bar Argon and 4 times with 10 bar syngas ($H_2$:CO, 1:1) under stirring (500 rpm). The autoclave was then charged with 10 bar syngas and the reaction mixture was heated until the temperature reached 85° C. The autoclave was then further pressurized with syngas to 30 bar, the stirring rate adjusted at 900 rpm and the temperature was set to 90° C. The hydroformylation was continued compensating the gas uptake with $H_2$:CO (1:1). After 20 h the reaction mixture was cooled to room temperature, the pressure released, and the autoclave was purged 5 times with 12 bar Argon. Product analysis was performed by gas chromatography using tetradecane as internal standard.

The results obtained are shown in Table 4.

TABLE 4

Hydroformylation of 4,4-dimethyl-1-vinylcyclohexyl acetate catalyzed by rhodium complexes with different ligands.

| Entry | Ligand | L:Rh:S | Conversion [1] | Selectivity [1] (1/2) | Yield [1] (1) |
|---|---|---|---|---|---|
| 1 | L1[2] | 1:2:20000 | >99.2% | 97/0.2 | >96% |
| 2 | L2[3] | 1:2:20000 | >99.5% | 98/0.2 | >97% |

TABLE 4-continued

Hydroformylation of 4,4-dimethyl-1-vinylcyclohexyl acetate catalyzed by rhodium complexes with different ligands.

| Entry | Ligand | L:Rh:S | Conversion [1)] | Selectivity [1)] (1/2) | Yield [1)] (1) |
|---|---|---|---|---|---|
| 3 | L3[4)] | 1:2:20000 | 56% | 93/0.3 | 52% |
| 4 | L4[5)] | 1:2:20000 | 54% | 92/0.3 | 50% |

[1)] determined by GC; 1 being 4,4-dimethyl-1-(3-oxopropyl)cyclohexyl acetate and 2 being 4,4-dimethyl-1-(1-oxopropan-2-yl)cyclohexyl acetate

[2)] 2-((3,3'-di-tert-butyl-2'-((4,8-di-tert-butyl-2,10-dimethoxydibenzo[d,f][1,3,2]dioxaphosphepin-6-yl)oxy)-5,5'-dimethoxy-[1,1'-biphenyl]-2-yl)oxy)-4H-naphtho[2,3-d][1,3,2]dioxaphosphinin-4-one; prepared according to *Angew. Chem*, 2001, 113, 1739-1741.

[3)] 2-((3,3'-di-tert-butyl-2'-((4,8-di-tert-butyl-2,10-dimethoxydibenzo[d,f][1,3,2]dioxaphosphepin-6-yl)oxy)-5,5'-dimethoxy-[1,1'-biphenyl]-2-yl)oxy)-8-methyl-4H-benzo[d][1,3,2]dioxaphosphinin-4-one; prepared according to *Angew. Chem*, 2001, 113, 1739-1741.

[4)] 8-methyl-2-((3,3',5,5'-tetra-tert-butyl-2'-((2,4,8,10-tetra-tert-butyldibenzo[d,f][1,3,2]dioxaphosphepin-6-yl)oxy)-[1,1'-biphenyl]-2-yl)oxy)-4H-benzo[d][1,3,2]dioxaphosphinin-4-one; prepared according to *Angew. Chem*, 2001, 113, 1739-1741.

[5)] 2-((3,3'-di-tert-butyl-2'-((4,8-di-tert-butyl-2,10-dimethoxydibenzo[d,f][1,3,2]dioxaphosphepin-6-yl)oxy)-5,5'-dimethoxy-[1,1'-biphenyl]-2-yl)oxy)-8-isopropyl-5-methyl-4H-benzo[d][1,3,2]dioxaphosphinin-4-one; prepared according to *Angew. Chem*, 2001, 113, 1739-1741.

Example 9

Preparation of 3-(4,4-dimethylcyclohex-1-en-1-yl)propanal 3 g (GC 97% purity, 12.86 mmol) of 4,4-dimethyl-1-(3-oxopropyl)cyclohexyl acetate in 12 g cyclohexane were added slowly (12 mL/h) from the top and under a $N_2$ flow to a heated pyrolysis column (pyrolysis oven at 500° C.), which was filled with 20 g quartz cylinder (Raschig 4 mm). When the addition was finished, the oven was cooled down and 5 g cyclohexane were added to wash the quartz cylinder. One obtains 20 g of a mixture which was analysed by GC because of the volatility of the product (GC purity 75.7%->3-(4,4-dimethylcyclohex-1-en-1-yl)propanal estimated: 9.70 mmol, 75% yield, GC purity 14.4%->3-(4,4-dimethylcyclohexylidene)propanal estimated 0.31 mmol, 1.84 mmol, 14.3% yield and GC purity 4.3%->4,4-dimethyl-1-(3-oxopropyl)cyclohexyl acetate estimated 0.55 mmol, 4.3% yield).

After workup (wash with a saturated aqueous $NaHCO_3$ solution and water) the volatile product mixture could be purified via column chromatography.

3-(4,4-dimethylcyclohex-1-en-1-yl)propanal $^1$H-NMR (300.13 MHz): 0.86 (s, 6H, 4'-$(CH_3)_2$), 1.34 (t, 2H, $^3J_{5',6'}$=6.4 Hz, H-5'), 1.75 (m, 2H, H-3'), 1.88-1.94 (m, 2H, H-6'), 2.28 (m, 2H, H-3), 2.48-2.54 (m, 2H, H-2), 5.32 (m, 1H, H-2'), 9.74 (t, 1H, $^2J_{1,2}$=2.0 Hz, H-1).

$^{13}$C-NMR (75.47 MHz): 26.2 (C-6'), 28.1 ($CH_3$), 28.4 (C-4'), 29.7 (C-3), 35.5 (C-5'), 39.1 (C-3'), 41.9 (C-2), 120.9 (C-2'), 134.2 (C-1'), 202.7 (C-1).

3-(4,4-dimethylcyclohexylidene)propanal $^{13}$C NMR (125 MHz, $CDCl_3$): δ 25.0, 28.1, 30.6, 32.8, 40.0, 40.8, 42.6, 109.5, 145.6, 200.2.

Example 10

Preparation of 1-(2-(1,3-dioxolan-2-yl)ethyl)-4,4-dimethylcyclohexyl acetate 34.1 g (94.2% purity, 141.4 mmol) of 4,4-dimethyl-1-(3-oxopropyl)cyclohexyl acetate were stirred in the presence of 13.9 g (212.0 mmol, 1.5 eq) ethylenglycol and 962 mg $KHSO_4$ (7.1 mmol, 5 mol %) under Dean-Stark conditions in 50 mL toluene at 105-113° C. for 1 h (internal temperature, water was eliminated during 1 hour). The mixture was cooled down to room temperature and 150 mL diethyl ether were added. After washing with 75 mL water, 75 mL of a saturated aqueous $NaHCO_3$ solution and 75 ml of brine the organic phase was dried over $Na_2SO_4$ and the solvent was evaporated under reduced pressure (crude 39.5 g). Kugelrohr distillation of the crude gave 2 fractions containing 33.8 g (125.0 mmol) of 1-(2-(1,3-dioxolan-2-yl)ethyl)-4,4-dimethylcyclohexyl acetate and 1.71 g (8.15 mmol) (2-(2-(4,4-dimethylcyclohex-1-en-1-yl)ethyl)-1,3-dioxolane (94.2% yield, 133.15 mmol).

1-(2-(1,3-dioxolan-2-yl)ethyl)-4,4-dimethylcyclohexyl acetate $^1$H-NMR (500.15 MHz): 0.89 (s, 3H), 0.92 (s, 3H), 1.18-1.23 (m, 2H, 1.33-1.39 (m, 2H), 1.43-1.51 (m, 2H), 1.61-1.66 (m, 2H), 1.99-2.02 (m, 2H), 2.00 (s, 3H), 2.08-2.14, (m, 2H), 3.81-3.88 (m, 2H). 3.93-4.00 (m, 2H), 4.83 (t, 1H, J=4.8 Hz).

$^{13}$C NMR (150 MHz, $CDCl_3$): δ 22.2, 25.4, 29.4, 29.4, 30.5, 31.1, 34.6, 38.3, 82.8, 170.4, 201.9.

(2-(2-(4,4-dimethylcyclohex-1-en-1-yl)ethyl)-1,3-dioxolane $^{13}$C NMR (125 MHz, $CDCl_3$): δ 26.2, 28.2, 28.5, 31.8, 32.2, 35.7, 39.3, 64.9, 104.5, 120.1, 135.4.

Example 11

Preparation of (2-(2-(4,4-dimethylcyclohex-1-en-1-yl)ethyl)-1,3-dioxolane 66 mg (0.349 mmol, 5 mol %) pTsOH·$H_2O$ were heated under stirring and Dean-Stark conditions (reflux) at 110° C. for 30 min in 20 mL toluene. 1.9 g (98.7% purity, 6.93 mmol) 1-(2-(1,3-dioxolan-2-yl)ethyl)-4,4-dimethylcyclohexyl acetate, were added slowly during 1 hour. The mixture was further stirred for one hour for the isomerisation of the exo double bond to the endo double bond. After cooling down to room temperature 30 ml of diethylether were added. After washing with 5 mL of a saturated aqueous $NaHCO_3$ solution and 10 ml of brine the organic phase was dried over $Na_2SO_4$ and the solvent was evaporated under reduced pressure (crude 1.53 g). Kugelrohr distillation of the crude gave 2 fractions containing 1.29 g of (2-(2-(4,4-dimethylcyclohex-1-en-1-yl)ethyl)-1,3-dioxolane (6.13 mmol, 89% yield), 68 mg 2-(2-(4,4-dimethylcyclohexylidene)ethyl)-1,3-dioxolane (0.323 mmol, 4.6% yield) and 14 mg 3-(4,4-dimethylcyclohex-1-en-1-yl)propanal (0.0842 mmol, 1.2% yield).

(2-(2-(4,4-dimethylcyclohex-1-en-1-yl)ethyl)-1,3-dioxolane (endo)

$^1$H-NMR (500.15 MHz): 0.88 (s, 3H), 1.35 (t, 2H, J=6.5 Hz), 1.74-1.79 (m, 4H), 1.92-1.97 (m, 2H), 2.07 (t, 2H, J=8.3 Hz), 3.82-3.88 (m, 2H), 3.93-4.00 (m, 2H), 4.86 (t, 1H, J=4.9 Hz), 5.34 (m, 1H).

$^{13}$C NMR (125 MHz, $CDCl_3$): δ 26.2, 28.2, 28.5, 31.8, 32.2, 35.7, 39.3, 64.9, 104.5, 120.1, 135.4.

2-(2-(4,4-dimethylcyclohexylidene)ethyl)-1,3-dioxolane (exo)

$^{13}$C NMR (100 MHz, $CDCl_3$): δ 24.8, 28.2, 30.6, 32.3, 32.9, 40.1, 40.9, 64.9, 104.6, 114.0, 142.8.

3-(4,4-dimethylcyclohex-1-en-1-yl)propanal $^1$H-NMR (300.13 MHz): 0.86 (s, 6H, 4'-$(CH_3)_2$), 1.34 (t, 2H, $^3J_{5',6'}$=6.4 Hz, H-5'), 1.75 (m, 2H, H-3'), 1.88-1.94 (m, 2H, H-6'), 2.28 (m, 2H, H-3), 2.48-2.54 (m, 2H, H-2), 5.32 (m, 1H, H-2'), 9.74 (t, 1H, $^2J_{1,2}$=2.0 Hz, H-1).

$^{13}$C-NMR (75.47 MHz): 26.2 (C-6'), 28.1 ($CH_3$), 28.4 (C-4'), 29.7 (C-3), 35.5 (C-5'), 39.1 (C-3'), 41.9 (C-2), 120.9 (C-2'), 134.2 (C-1'), 202.7 (C-1).

Example 12

Preparation of (2-(2-(4,4-dimethylcyclohex-1-en-1-yl)ethyl)-1,3-dioxolane 2 g (7.39 mmol) 1-(2-(1,3-dioxolan-2-yl)ethyl)-4,4-dimethylcyclohexyl acetate were added slowly (12 mL/h) from the top and under a $N_2$ flow to a heated pyrolysis column (pyrolysis oven at 500° C.), which was filled with 18 g quartz cylinder (Raschig 4 mm). When the addition was finished, the oven was cooled down and 10 ml cyclohexane were added to wash the quartz cylinder. After the addition of further 20 mL of cyclohexane the mixture was washed twice with 10 mL of a saturated aqueous $NaHCO_3$ solution. The aqueous phases were combined and extracted once with 10 mL of cyclohexane. The combined organic phases was washed with brine and was dried over sodium sulfate. The solvent was evaporated under reduced pressure (Rotavap 10 mbar, 45° C.). 1.452 g of product were obtained (70.6% purity 2-(2-(4,4-dimethylcyclohex-1-en-1-yl)ethyl)-1,3-dioxolane, 4.87 mmol, 65.9% yield, 24.6% purity 2-(2-(4,4-dimethylcyclohexylidene)ethyl)-1,3-dioxolane, 1.70 mmol, 23.0% yield, 1.3% purity 3-(4,4-dimethylcyclohex-1-en-1-yl)propanal, 0.0148 mmol, 1.5% yield).

The quantity of 2-(2-(4,4-dimethylcyclohexylidene)ethyl)-1,3-dioxolane could be increased by heating in the presence of 5 mol % pTsOH·$H_2O$ in 15 mL toluene at 110° C. After 3 hours we obtained via GC analysis 94.0% 2-(2-(4,4-dimethylcyclohex-1-en-1-yl)ethyl)-1,3-dioxolane, 3.7% 2-(2-(4,4-dimethylcyclohexylidene)ethyl)-1,3-dioxolane and 0.2% 3-(4,4-dimethylcyclohex-1-en-1-yl)propanal.

Example 13

Preparation of 3-(4,4-dimethylcyclohex-1-en-1-yl)propanal 6.24 g (2-(2-(4,4-dimethylcyclohex-1-en-1-yl)ethyl)-1,3-dioxolane (91.7% purity, 27.20 mmol, containing 1.08 mmol 3-(4,4-dimethylcyclohex-1-en-1-yl)propanal), 9.25 g AcOH (155.7 mmol, 5.5 eq) and 9.25 g water (519 mmol, 19.1 eq) were heated under stirring in 9.1 mL heptane at 85° C. (reflux) for 3 hours. After cooling down to room temperature 25 mL diethyl ether were added. The acetic acid is neutralized with an aqueous 25% NaOH solution at 10° C. to pH 6. The organic phase is separated and washed with 15 mL of a saturated aqueous $NaHCO_3$ solution and 15 ml of brine. After drying over $Na_2SO_4$ the solvent was evaporated under reduced pressure (500-100 mbar, 40° C.). The crude (contains still some heptane) was purified by flash chromatography (220 g $SiO_2$, eluent from pentane to pentane 9/diisopropylether 1). 3.348 g (98% purity, 19.73 mmol, 69.8% yield) 3-(4,4-dimethylcyclohex-1-en-1-yl)propanal were obtained and 1.46 g (90.0% purity, 6.25 mmol, 22.1% yield) starting material (2-(2-(4,4-dimethylcyclohex-1-en-1-yl)ethyl)-1,3-dioxolane were recycled.

3-(4,4-dimethylcyclohex-1-en-1-yl)propanal was obtained in overall yield of at least 60% from 1-ethynyl-4,4-dimethylcyclohexanol following the sequence reported in examples 2, 6, 8, 9 and 11. Whereas, 3-(4,4-dimethylcyclohex-1-en-1-yl)propanal was obtained with a 27% overall yield starting from 4,4-dimethyl-cyclohexanol as reported in EP1529770. The invention's process allows producing 3-(cyclohex-1-en-1-yl)propanal derivatives with an improved yield.

Example 14

Hydroformylation of 4,4-dimethyl-1-vinylcyclohex-1-ene 4,4-dimethyl-1-vinylcyclohex-1-ene (136 mg, 1.0 mmol), Ligand (3.5 mM in EtOAc, 2.0 mL) and $Rh(acac)(CO)_2$ (1.0 mM in EtOAc, 1.43 mL) were added to an autoclave (HEL 20 mL/200 bar). The autoclave was purged 3 times with 8 bar Argon and 4 times with 10 bar syngas ($H_2$:CO, 1:1) under stirring (500 rpm). The autoclave was then charged with 10 bar syngas and the reaction mixture was heated until the temperature reached 75° C. The autoclave was then further pressurized with syngas to 40 bar, the stirring rate adjusted at 900 rpm and the temperature was set to 80° C. The hydroformylation was continued compensating the gas uptake with $H_2$:CO (1:1). After 22 h the reaction mixture was cooled to room temperature, the pressure released, and the autoclave was purged 5 times with 12 bar Argon. Product analysis was performed by gas chromatography.

The results obtained are shown in Table 5.

TABLE 5

Hydroformylation of 4,4-dimethyl-1-vinylcyclohex-1-ene catalyzed by rhodium complexes with different ligands.

| Entry | Ligand | Conv. (%) [1)] | Selectivity (%) [1)] 3 | 4 | 5 | 6 | 7 | l:b ratio (3/[4 + 5]) | Yield of (3) (%) [1)] |
|---|---|---|---|---|---|---|---|---|---|
| 1 | BIPHEPHOS | 90 | 74 | 9 | — | 14 | 3 | 8.2 | 66.6 |

[1)] determined by GC; 3 being 3-(4,4-dimethylcyclohex-1-en-1-yl)propanal, 4 being 2-(4,4-dimethylcyclohex-1-en-1-yl)propanal, 5 being 2-(4,4-dimethylcyclohexylidene)propanal, 6 being 6-ethylidene-3,3-dimethylcyclohex-1-ene and 7 being 1-ethyl-4,4-dimethylcyclohex-1-ene. 3-(4,4-dimethylcyclohex-1-en-1-yl)propanal (3)

$^{1}$H-NMR (300.13 MHz): 0.86 (s, 6H, 4'-($CH_3$)$_2$), 1.34 (t, 2H, $^{3}J_{5',6'}$=6.4 Hz, H-5'), 1.75 (m, 2H, H-3'), 1.88-1.94 (m, 2H, H-6'), 2.28 (m, 2H, H-3), 2.48-2.54 (m, 2H, H-2), 5.32 (m, 1H, H-2'), 9.74 (t, 1H, $^{2}J_{1,2}$=2.0 Hz, H-1).

$^{13}$C-NMR (75.47 MHz): 26.2 (C-6'), 28.1 ($CH_3$), 28.4 (C-4'), 29.7 (C-3), 35.5 (C-5'), 39.1 (C-3'), 41.9 (C-2), 120.9 (C-2'), 134.2 (C-1'), 202.7 (C-1).

2-(4,4-dimethylcyclohex-1-en-1-yl)propanal (4)

$^{1}$H-NMR (500.13 MHz): 0.89 (2×s, 6H, 4'-($CH_3$)$_2$), 1.16 (d, 3H, $^{3}J_{2,3}$=7.0 Hz, 3-$CH_3$), 1.37 (t, 2H, $^{3}J_{5',6'}$=6.4 Hz, H-5'), 1.85 (m, 2H, H-3'), 1.86-1.88, 1.96-2.02 (2×m, 2H, H-6'), 2.93 (q, 1H, $^{2}J_{1,2}$=1.7 Hz, $^{2}J_{2,3}$=7.0 Hz, H-2), 5.51 (m, 1H, H-2'), 9.49 (d, 1H, $^{2}J_{1,2}$=1.7 Hz, H-1).

$^{13}$C-NMR (125.76 MHz): 12.1 (3-$CH_3$), 25.0 (C-6'), 28.2 (4'-($CH_3$)$_2$), 28.4 (C-4'), 35.4 (C-5'), 39.4 (C-3'), 54.1 (C-2), 125.0 (C-2'), 132.7 (C-1'), 202.1 (C-1).

6-ethylidene-3,3-dimethylcyclohex-1-ene (6)

$^{1}$H-NMR (400.13 MHz, 2 isomers): 1.01, 1.02 (4×s, 6H, 4'-($CH_3$)$_2$), 1.50 (t, 2H, $^{3}J_{5',6'}$=6.2 Hz, H-5'), 1.67 (d, 3H, $^{3}J_{1,2}$=7.0 Hz, H-2), 2.29, 2.33 (2×t, 2H, 1H, $^{3}J_{5',6'}$=6.2 Hz, H-6'), 5.20, 5.33 (2×q, 1H, $^{3}J_{1,2}$=7.0 Hz, H-1), 5.40, 5.54 (2×d, 1H, $^{3}J_{2',3'}$=10.0 Hz, H-3'), 5.89, 5.95 (2×d, 1H, $^{3}J_{2',3'}$=10.0 Hz, H-2').

$^{13}$C-NMR (100.63 MHz, 2 isomers): 12.5, 13.1 (C-2), 21.7 (C-6'), 29.1, 29.2 (4'-$CH_3$), 32.0 (C-4'), 36.6, 37.4 (C-5'), 121.2 (C-1), 128.3 (C-2'), 135.3 (C-1'), 137.2, 139.6 (C-3').

1-ethyl-4,4-dimethylcyclohex-1-ene (7)

$^{1}$H-NMR (500.13 MHz): 0.89 (s, 6H, 4'-($CH_3$)$_2$), 0.99 (t, 3H, $^{3}J_{1,2}$=7.5 Hz, H-2), 1.36 (t, 2H, $^{3}J_{5',6'}$=6.5 Hz, H-5'), 1.77 (m, 2H, H-3'), 1.95 (m, 2H, H-1), 1.96 (m, 2H, H-6'), 5.30 (m, 1H, H-2').

$^{13}$C-NMR (125.76 MHz): 12.5 (C-2), 26.1 (C-1), 28.2 (2×$CH_3$), 28.6 (C-4'), 30.2 (C-6'), 35.8 (C-5'), 39.3 (C-3'), 118.3 (C-2'), 138.0 (C-1').

Example 15

Hydroformylation of 4,4-dimethyl-1-vinylcyclohex-1-ene with BIPHEPHOS-Rh Catalyst a) General Procedure:

4,4-dimethyl-1-vinylcyclohex-1-ene (136 mg, 1.0 mmol), BIPHEPHOS (in EtOAc) and Rh(acac)$(CO)_2$ (in EtOAc) were added to an autoclave (HEL 20 mL/200 bar) according to Table 6 (total volume of EtOAc=3.5 mL). The autoclave was purged 3 times with 8 bar Argon and 4 times with 10 bar syngas ($H_2$:CO, 1:1) under stirring (500 rpm). The autoclave was then charged with 10 bar syngas and the reaction mixture was heated until the temperature reached 95° C. The autoclave was then further pressurized with syngas to 20 bar, the stirring rate adjusted at 900 rpm and the temperature was set to 100° C. The hydroformylation was continued compensating the gas uptake with $H_2$:CO (1:1). After the reaction time indicated in Table 6 the reaction mixture was cooled to room temperature, the pressure released, and the autoclave was purged 5 times with 12 bar Argon. Product analysis was performed by gas chromatography using tetradecane as internal standard.

The results obtained are shown in Table 6.

TABLE 6

Hydroformylation of 4,4-dimethyl-1-vinylcyclohex-1-ene catalyzed by BIPHEPHOS-Rh catalyst at different catalyst loadings.

| Entry | R:L:S | Time (h) | Conv. (%) [1] | Selectivity (%) [1] 3 | 4 | 5 | 6 | 7 | l:b ratio (3/[4 + 5]) | Yield of (3) (%) [1] |
|---|---|---|---|---|---|---|---|---|---|---|
| 1 | 1:5:300 | 22 | 100 | 67 | 5 | 0.8 | 23 | 3 | 11.6 | 67.0 |
| 2 | 1:5:300 | 72 | 100 | 82 | 8 | 0.8 | 4 | 4 | 9.6 | 82.0 |
| 3 [2] | 1:5:300 | 72 | 100 | 84 | 5 | 1.5 | 4 | 5 | 12.9 | 84.0 |
| 4 | 1:5:500 | 22 | 100 | 66 | 5 | 0.5 | 25 | 3 | 12.0 | 66.0 |
| 5 | 1:5:500 | 72 | 100 | 80 | 6 | 1 | 9 | 4 | 11.4 | 80.0 |
| 6 | 1:5:700 | 22 | 100 | 66 | 5 | — | 25 | 3 | 13.2 | 66.0 |
| 7 | 1:5:700 | 72 | 100 | 75 | 9 | — | 13 | 1 | 8.3 | 75.0 |
| 8 | 1:5:1000 | 72 | >99.8 | 70 | 5 | 0.2 | 3 | 20 | 13.5 | 69.9 |
| 9 | 1:2.5:4000 | 72 | >99.7 | 66 | 5 | — | 25 | 3 | 13.2 | 65.8 |
| 10 | 1:2.5:8000 | 72 | 89 | 63 | 5 | — | 29 | 3 | 12.6 | 56.1 |

[1] determined by GC;; 3 being 3-(4,4-dimethylcyclohex-1-en-1-yl)propanal, 4 being 2-(4,4-dimethylcyclohex-1-en-1-yl)propanal, 5 being 2-(4,4-dimethylcyclohexylidene)propanal, 6 being 6-ethylidene-3,3-dimethylcyclohex-1-ene and 7 being 1-ethyl-4,4-dimethylcyclohex-1-ene.

[2] $H_2$:CO (2:1)

Example 16

Hydroformylation of 4,4-dimethyl-1-vinylcyclohex-1-ene with BIPHEPHOS-Rh Catalyst a) General Procedure:

4,4-dimethyl-1-vinylcyclohex-1-ene (136 mg, 1.0 mmol), BIPHEPHOS (in EtOAc) and $HRh(CO)(PPh_3)_3$ (in EtOAc) were added to an autoclave (HEL 20 mL/200 bar) according to Table 3 (total volume of EtOAc=3.5 mL). The autoclave was purged 3 times with 8 bar Argon and 4 times with 10 bar syngas ($H_2$:CO, 1:1) under stirring (500 rpm). The autoclave was then charged with 10 bar syngas and the reaction mixture was heated until the temperature reached 95° C. The autoclave was then further pressurized with syngas to 20 bar, the stirring rate adjusted at 900 rpm and the temperature was set to 100° C. The hydroformylation was continued compensating the gas uptake with $H_2$:CO (1:1). After 72 h the reaction mixture was cooled to room temperature, the pressure released, and the autoclave was purged 5 times with 12 bar Argon. Product analysis was performed by gas chromatography using tetradecane as internal standard.

The results obtained are shown in Table 7.

TABLE 7

Hydroformylation of 4,4-dimethyl-1-vinylcyclohex-1-ene catalyzed by BIPHEPHOS-Rh catalyst at different catalyst loadings.

| Entry | R:L:S | Conv. (%) [1] | Selectivity (%) [1] 3 | 4 | 5 | 6 | 7 | l:b ratio (3/[4 + 5]) | Yield of (3) (%) [1] |
|---|---|---|---|---|---|---|---|---|---|
| 1 | 1:1:1000 | 100 | 71 | 6 | — | 19 | 4 | 11.8 | 71.0 |
| 2 | 1:2.5:1000 | >99.9 | 71 | 6 | 0.1 | 16 | 5 | 11.6 | 71.0 |
| 3 | 1:2.5:2000 | >99.8 | 69 | 5 | — | 23 | 3 | 13.8 | 68.9 |
| 4 | 1:2.5:4000 | >99.7 | 67 | 5 | — | 25 | 3 | 13.4 | 66.8 |
| 5 | 1:2.5:8000 | >99.4 | 65 | 5 | — | 27 | 3 | 13.0 | 64.6 |
| 6 | 1:2.5:16000 | 96 | 66 | 5 | — | 26 | 3 | 13.2 | 63.4 |

[1] determined by GC;; 3 being 3-(4,4-dimethylcyclohex-1-en-1-yl)propanal, 4 being 2-(4,4-dimethylcyclohex-1-en-1-yl)propanal, 5 being 2-(4,4-dimethylcyclohexylidene)propanal, 6 being 6-ethylidene-3,3-dimethylcyclohex-1-ene and 7 being 1-ethyl-4,4-dimethylcyclohex-1-ene.
2) $H_2$:CO (2:1)

Example 17

Hydroformylation of 4,4-dimethyl-1-vinylcyclohex-1-ene with Xantphos-Rh Catalyst a) General Procedure:

4,4-dimethyl-1-vinylcyclohex-1-ene (136 mg, 1.0 mmol), Xantphos (in EtOAc) and $Rh(acac)(CO)_2$ (in EtOAc) were added to an autoclave (HEL 20 mL/200 bar) according to Table 2 (total volume of EtOAc=3.5 mL if no other volume is indicated). The autoclave was purged 3 times with 8 bar Argon and 4 times with 10 bar syngas ($H_2$:CO, 1:1) under stirring (500 rpm). The autoclave was then charged with 10 bar syngas and the reaction mixture was heated until the temperature reached 65-105° C. The autoclave was then further pressurized with syngas to 60 bar, the stirring rate adjusted at 900 rpm and the temperature was set to 70-110° C. The hydroformylation was continued compensating the gas uptake with $H_2$:CO (1:1). After 72 h the reaction mixture was cooled to room temperature, the pressure released, and the autoclave was purged 5 times with 12 bar Argon. Product analysis was performed by gas chromatography.

The results obtained are shown in Table 8.

TABLE 8

Hydroformylation of 4,4-dimethyl-1-vinylcyclohex-1-ene catalyzed by Xantphos-Rh catalyst under different conditions.

| Entry | R:L:S | T (° C.) | Conv. (%) [1] | Selectivity (%) [1] 3 | 4 | 5 | 6 | 7 | l:b ratio (3/[4 + 5]) | Yield of (3) (%) [1] |
|---|---|---|---|---|---|---|---|---|---|---|
| 1 | 1:5:700 | 80 | 48 | 67 | 30 | — | 1 | 2 | 2.2 | 32.2 |
| 2 | 1:5:700 | 110 | 99 | 62 | 32 | 2 | 0.5 | 2 | 1.8 | 61.4 |
| 3 | 1:5:300 | 90 | 96 | 66 | 29 | 2 | — | 2 | 2.1 | 63.4 |

[1] determined by GC; 3 being 3-(4,4-dimethylcyclohex-1-en-1-yl)propanal, 4 being 2-(4,4-dimethylcyclohex-1-en-1-yl)propanal, 5 being 2-(4,4-dimethylcyclohexylidene)propanal, 6 being 6-ethylidene-3,3-dimethylcyclohex-1-ene and 7 being 1-ethyl-4,4-dimethylcyclohex-1-ene.
2) total volume of EtOAc = 0.9 mL

Example 18

Hydroformylation of 4,4-dimethyl-1-vinylcyclohex-1-ene with Xantphos Analogs-Rh Catalysts a) General Procedure:

4,4-dimethyl-1-vinylcyclohex-1-ene (136 mg, 1.0 mmol), Ligand (3.5 mM in EtOAc, 2.0 mL) and Rh(acac)$(CO)_2$ (0.67 mM in EtOAc, 1.49 mL) were added to an autoclave (HEL 20 mL/200 bar). The autoclave was purged 3 times with 8 bar Argon and 4 times with 10 bar syngas ($H_2$:CO, 1:1) under stirring (500 rpm). The autoclave was then charged with 10 bar syngas and the reaction mixture was heated until the temperature reached 85° C. The autoclave was then further pressurized with syngas to 60 bar, the stirring rate adjusted at 900 rpm and the temperature was set to 90° C. The hydroformylation was continued compensating the gas uptake with $H_2$:CO (1:1). After 72 h the reaction mixture was cooled to room temperature, the pressure released, and the autoclave was purged 5 times with 12 bar Argon. Product analysis was performed by gas chromatography.

The results obtained are shown in Table 9.

TABLE 9

Hydroformylation of 4,4-dimethyl-1-vinylcyclohex-1-ene catalyzed by Xantphos analogs-Rh catalysts.

| Entry | Ligand | Conv. (%) [1] | Selectivity (%) [1] 3 | 4 | 5 | 6 | 7 | l:b ratio (3/[4 + 5]) | Yield of (3) (%) [1] |
|---|---|---|---|---|---|---|---|---|---|
| 1 | L5[2] | 31 | 62 | 38 | — | — | — | 1.6 | 19.2 |
| 2 | L6[3] | 46 | 61 | 34 | — | — | 2 | 1.8 | 28.1 |
| 3 | L7[4] | 38 | 64 | 31 | — | — | 3 | 2.1 | 24.3 |
| 4 | L8[5] | 52 | 67 | 28 | — | — | 4 | 2.4 | 34.8 |
| 5 | L9[6] | 62 | 71 | 26 | — | — | 3 | 2.7 | 44.0 |

[1] determined by GC; 3 being 3-(4,4-dimethylcyclohex-1-en-1-yl)propanal, 4 being 2-(4,4-dimethylcyclohex-1-en-1-yl)propanal, 5 being 2-(4,4-dimethylcyclohexylidene)propanal, 6 being 6-ethylidene-3,3-dimethylcyclohex-1-ene and 7 being 1-ethyl-4,4-dimethylcyclohex-1-ene.
[2] (1S,1'S)-(+)-(2,7-di-tert-butyl-9,9-dimethyl-9H-xanthene-4,5-diyl)bis((2-methoxyphenyl)(phenyl)phosphine); prepared according to *Tetrahedron*, 2020, 76, 131142.
[3] (1S,1'S)-(−)-(9,9-Dimethyl-9H-xanthene-4,5-diyl)bis(naphthalen-2-yl(phenyl)phosphine); prepared according to ACS *Catalysis*, 2017, 7, 6162-6169.
[4] (1S,1'S)-(−)-(9,9-Dimethyl-9H-xanthene-4,5-diyl)bis((4-methoxyphenyl)(phenyl)phosphine); prepared according to ACS *Catalysis*, 2017, 7, 6162-6169.
[5] (1S,1'S)-(−)-(2,7-di-tert-butyl-9,9-dimethyl-9H-xanthene-4,5-diyl)bis((1-naphthyl)(phenyl)phosphine); prepared according to *Tetrahedron*, 2020, 76, 131142.
[6] (1S,1'S)-(−)-(2,7-di-tert-butyl-9,9-dimethyl-9H-xanthene-4,5-diyl)bis((4-methylphenyl)(phenyl)phosphine); prepared according to *Tetrahedron*, 2020, 76, 131142.

Example 19

Hydroformylation of 4,4-dimethyl-1-vinylcyclohex-1-ene with BIPHEPHOS-Rh Catalyst Rh(acac)$(CO)_2$ (6.0 mM in EtOAc, 4.6 mL), BIPHEPHOS (14.6 mM in EtOAc, 9.5 mL) and a solution of 4,4-dimethyl-1-vinylcyclohex-1-ene (3.75 g, 27.52 mmol) in EtOAc (80 mL) were added to an autoclave (Premex 200 mL/200 bar) kept under 1 bar Ar. The autoclave was charged with 10 bar syngas ($H_2$:CO, 1:1) and the reaction mixture was heated under vigorous stirring until the temperature reached 100° C. The autoclave was then further pressurized with syngas to 23 bar and the hydroformylation was continued compensating the gas uptake with $H_2$:CO (1:1). After 24 h, the reaction mixture was cooled to room temperature, the pressure released and the autoclave purged with Ar. (GC yield (with internal standard) 66%). The solvent was evaporated under reduced pressure (45° C., 200 mbar). The crude was purified by flash chromatography (120 g $SiO_2$, eluent from cyclohexane/AcOEt 99/1 to cyclohexane/AcOEt 95/5). 4.9 g of product 3-(4,4-dimethylcyclohex-1-en-1-yl)propanal/2-(4,4-dimethylcyclohex-1-en-1-yl)propanal 93/6 were obtained, which contained still some solvent. A Kugelrohr distillation gave 2.90 g of 3-(4,4-dimethylcyclohex-1-en-1-yl)propanal (92.8% GC purity, 16.18 mmol, 59% yield) and 2-(4,4-dimethylcyclohex-1-en-1-yl)propanal (6.3% GC purity). Some product is lost because of the volatility.

Example 20

Hydroformylation of 6-ethylidene-3,3-dimethylcyclohex-1-ene—Recycling of Side Product 6 Formed During Hydroformylation 6-ethylidene-3,3-dimethylcyclohex-1-ene (136 mg, 1.0 mmol), Ligand (3.5 mM in EtOAc, 2.0 mL) and Rh(acac)$(CO)_2$ (1.0 mM in EtOAc, 1.43 mL) were added to an autoclave (HEL 20 mL/200 bar). The autoclave was purged 3 times with 8 bar Argon and 4 times with 10 bar syngas ($H_2$:CO, 1:1) under stirring (500 rpm). The autoclave was then charged with 10 bar syngas and the reaction mixture was heated until the temperature reached 95° C. The autoclave was then further pressurized with syngas to 20 bar, the stirring rate adjusted at 900 rpm and the temperature was set to 100° C. The hydroformylation was continued compensating the gas uptake with $H_2$:CO (1:1). After the reaction time indicated in Table 6, the reaction mixture was cooled to room temperature, the pressure released, and the autoclave was purged 5 times with 12 bar Argon. Product analysis was performed by gas chromatography.

The results obtained are shown in Table 10.

TABLE 10

Hydroformylation of 6-ethylidene-3,3-dimethylcyclohex-1-ene catalyzed by BIPHEPHOS-modified Rh catalyst.

| Entry | R:L:S | Time (h) | Conv. (%) [1] | Selectivity (%) [1] 3 | 4 | 5 | 7 | l:b ratio (3/[4 + 5]) | Yield of (3) (%) [1] |
|---|---|---|---|---|---|---|---|---|---|
| 1 | 1:5:500 | 92 | 65 | 85 | 10 | — | 4 | 8.5 | 55.3 |
| 2 | 1:5:300 | 92 | 81 | 85 | 9 | — | 4 | 9.4 | 68.9 |
| 3 | 1:5:150 | 72 | 90 | 83 | 10 | 3 | 2 | 8.3 | 74.7 |
| 4 [2] | 1:5:150 | 72 | 75 | 80 | 14 | 4 | 0.7 | 5.7 | 60.0 |

TABLE 10-continued

Hydroformylation of 6-ethylidene-3,3-dimethylcyclohex-1-ene catalyzed by BIPHEPHOS-modified Rh catalyst.

| Entry | R:L:S | Time (h) | Conv. (%) [1] | Selectivity (%) [1] 3 | 4 | 5 | 7 | l:b ratio (3/[4 + 5]) | Yield of (3) (%) [1] |
|---|---|---|---|---|---|---|---|---|---|
| 5 [3] | 1:5:150 | 72 | 95 | 84 | 8 | 2 | 4 | 10.5 | 79.8 |
| 6 [4] | 1:5:150 | 72 | 98 | 84 | 7 | 2 | 6 | 12.0 | 82.3 |

[1] determined by GC; 3 being 3-(4,4-dimethylcyclohex-1-en-1-yl)propanal, 4 being 2-(4,4-dimethylcyclohex-1-en-1-yl)propanal, 5 being 2-(4,4-dimethylcyclohexylidene)propanal and 7 being 1-ethyl-4,4-dimethylcyclohex-1-ene.
[2] $H_2$:CO = 1:2
[3] $H_2$:CO = 2:1
[4] $H_2$:CO = 3:1

Example 21

Preparation of Different Compounds of Formula (II)

The starting materials 4-(tert-butyl)cyclohexan-1-one (CAS 98-53-3, Aldrich), 3-isopropylcyclohexan-1-one (CAS 23396-36-3, Aldrich), 4-butylcyclohexan-1-one (CAS 61203-82-5, Aurumpharmatech), 2-ethyl-4,4-dimethylcyclohexan-1-one (CAS 55739-89-4, Aurorafinechemicals), 3-isopropylcyclopentan-1-one (CAS 10264-56-9, Alfa-chemistry) are either commercially available or can be prepared according to literature procedures.

a) Step 1: Preparation of Vinylalcohols by the Addition of a Vinylgrignard Reagent to the Cyclic Substituted Ketone General Procedure for the Addition of the Cyclic Substituted Ketone to a Solution of Vinylmagnesium Chloride:

To a cooled solution (0° C.) of 196.6 mL vinylmagnesium chloride (1.6 M in THF, 314.5 mmol, 1.1 eq) and 150 mL THF was added slowly a solution of the cyclic ketone (285.9 mmol) in 60 mL THF. The internal temperature did not exceed 5° C. during the addition of the cyclic substituted ketone. The mixture was further stirred at 0° C. over night (16 hours) and analysed by GC. The reaction mixture was added slowly to a cooled solution of 21 g AcOH (343.1 mmol) in 200 ml water. The phases were separated and the aqueous phase was extracted with 150 mL TBME. The combined organic phase were washed with a saturated aqueous $NaHCO_3$ solution and a saturated aqueous NaCl solution. After drying over $Na_2SO_4$ the solvent was evaporated under reduced pressure (500-50 mbar, 50° C.). The crude was purified by flash chromatography or by a distillation through a Vigreux column under reduced pressure.

4-(tert-butyl)-1-vinylcyclohexan-1-ol

The compound was prepared according the general procedure and by using 4-(tert-butyl)cyclohexan-1-one as a cyclic ketone.

GC crude: 91.2% 4-(tert-butyl)-1-vinylcyclohexan-1-ol.

94.0% purity (GC) after purification. (78% yield)

NMR analysis results in $CDCl_3$ were in accordance with data from literature (N. Miralles, R. Alam, K. J. Szabó, E. Fernández, *Angew. Chem. Int. Ed.* 2016, SS, 4303-4307).

trans-4-(tert-butyl)-1-vinylcyclohexan-1-ol: major isomer (52/48 trans/cis)

$^{13}C$ NMR (100 MHz, $CDCl_3$): δ 24.5, 27.6, 32.3, 39.2, 47.5, 72.2, 113.8, 147.0.

cis-4-(tert-butyl)-1-vinylcyclohexan-1-ol: minor isomer $^{13}C$ NMR (100 MHz, $CDCl_3$): δ 22.3, 27.6, 32.4, 37.7, 47.6, 71.3, 110.9, 142.8.

3-isopropyl-1-vinylcyclohexan-1-ol

The compound was prepared according the general procedure and using 3-isopropylcyclohexan-1-one (containing 10% 4-isopropylcyclohexan-1-one) as a cyclic ketone.

GC crude: 82.6% purity 3-isopropyl-1-vinylcyclohexan-1-ol from 3-isopropylcyclohexan-1-one (85.7% purity)

88.8% purity (GC) after purification (86% yield) containing 10% 4-isopropyl-1-vinylcyclohexan-1-ol, mixture of trans/cis isomers).

(1SR,3SR)-3-isopropyl-1-vinylcyclohexan-1-ol: Major Isomer (51/49 trans/cis)

$^1H$-NMR (500.15 MHz): 0.86 (d, 3H, J=6.8 Hz), 0.87 (d, 3H, J=6.8 Hz), 1.14 (t, 1H, J=12.8 Hz), 1.28 (s, 1H), 1.33-1.47 (m, 3H), 1.34-1.53 (m, 1H), 1.54-1.61 (m, 2H), 1.62-1.68 (m, 2H), 1.69-1.75 (m, 1H), 5.00 (dd, 1H, J=10.8 Hz, J=1.2 Hz), 5.23 (dd, 1H, J=17.4 Hz, J=1.2 Hz), 5.94 (dd, 1H, J=17.4 Hz, J=10.8 Hz).

$^{13}C$ NMR (125 MHz, $CDCl_3$): δ 19.5, 19.7, 21.5, 28.7, 32.6, 37.0, 38.5, 40.6, 72.4, 110.7, 147.2.

(1SR,3RS)-3-isopropyl-1-vinylcyclohexan-1-ol: Minor Isomer $^1H$-NMR (500.15 MHz): 0.86 (d, 6H, J=6.9 Hz), 0.89-1.01 (m, 1H), 1.18-1.25 (m, 2H), 1.27-1.38 (m, 1H), 1.39-1.48 (m, 2H), 1.58 (s, 1H), 1.63-1.76 (m, 3H), 1.78-1.88 (m, 2H), 5.15 (dd, 1H, J=10.8 Hz, J=1.2 Hz), 5.31 (dd, 1H, J=17.6 Hz, J=1.3 Hz), 6.08 (dd, 1H, J=17.5 Hz, J=10.8 Hz).

$^{13}C$ NMR (125 MHz, $CDCl_3$): δ 19.7, 19.7, 23.3, 28.9, 32.7, 38.9, 41.2, 42.5, 72.9, 113.7, 143.3.

4-isopropyl-1-vinylcyclohexan-1-ol (mixture of trans/cis isomers): NMR analysis results in $CDCl_3$ were in accordance with data from literature (C. A. Discolo, E. E. Touney, S. V. Pronin, *J. Am. Chem. Soc.* 2019 141 (44), 17527-17532).

4-butyl-1-vinylcyclohexan-1-ol

The compound was prepared according the general procedure and using 4-butylcyclohexan-1-one as a cyclic ketone.

GC crude: 96.1% 4-butyl-1-vinylcyclohexan-1-ol.

94.5% purity (GC) after purification (99% yield).

trans-4-butyl-1-vinylcyclohexan-1-ol: major isomer (58/42 trans/cis)

$^1$H-NMR (500.15 MHz): 0.89 (t, 3H, J=7.0 Hz), 1.02-1.12 (m, 2H), 1.17-1.36 (m, 7H), 1.46-1.57 (m, 3H), 1.68-1.78 (m, 2H), 1.78-1.86 (m, 2H), 5.13 (dd, 1H, J=10.9 Hz, J=1.2 Hz), 5.31 (dd, 1H, J=17.5 Hz, J=1.2 Hz), 6.07 (dd, 1H, J=17.5 Hz, J=10.9 Hz).

$^{13}$C NMR (125 MHz, $CDCl_3$): δ 14.1, 23.0, 29.5, 29.5, 35.5, 36.3, 37.9, 72.4, 113.4, 143.4.

cis-4-butyl-1-vinylcyclohexan-1-ol: minor isomer $^1$H-NMR (500.15 MHz): 0.86-0.92 (m, 3H), 1.16-1.36 (m, 12H), 1.42-1.51 (m, 2H), 1.56-1.64 (m, 4H), 4.99 (dd, 1H, J=10.8 Hz, J=1.3 Hz), 5.23 (dd, 1H, J=17.4 Hz, J=1.3 Hz), 5.93 (dd, 1H, J=17.4 Hz, J=10.8 Hz).

$^1$C NMR (125 MHz, $CDCl_3$): δ 14.1, 23.0, 28.1, 29.2, 36.7, 36.9, 37.0, 71.6, 110.9, 146.9.

2-ethyl-4,4-dimethyl-1-vinylcyclohexan-1-ol

The compound was prepared according the general procedure and using 2-ethyl-4,4-dimethylcyclohexan-1-one as a cyclic ketone.

GC crude: 94.1% 2-ethyl-4,4-dimethyl-1-vinylcyclohexan-1-ol.

95.5% purity (GC) after purification (85% yield).

(1SR,2SR)-2-ethyl-4,4-dimethyl-1-vinylcyclohexan-1-ol (major isomer, cis/trans 87/13)

$^1$H-NMR (500.15 MHz): 0.83 (t, 3H, J=7.3 Hz), 0.91 (s, 3H), 0.95 (s, 3H), 1.10-1.23 (m, 2H), 1.27-1.43 (m, 4H), 1.48-1.59 (m, 2H), 1.61.1.70 (m, 1H), 5.07 (dd, 1H, J=10.8 Hz, J=1.4 Hz), 5.24 (dd, 1H, J=17.3 Hz, J=1.4 Hz), 5.84 (dd, 1H, J=17.3 Hz, J=10.8 Hz).

$^{13}$C NMR (125 MHz, $CDCl_3$): δ 12.3, 22.3, 24.2, 30.2, 33.1, 34.0, 35.3, 39.4, 41.8, 74.5, 111.6, 146.4.

(1SR,2RS)-2-ethyl-4,4-dimethyl-1-vinylcyclohexan-1-ol (minor isomer)

$^1$H-NMR (500.15 MHz): 0.99 (s, 3H), 1.74-1.80 (m, 1H), 5.14 (dd, 1H, J=11.0 Hz, J=1.7 Hz), 5.31 (dd, 1H, J=17.3 Hz, J=1.7 Hz), 6.19 (dd, 1H, J=17.3 Hz, J=11.0 Hz).

$^{13}$C NMR (125 MHz, $CDCl_3$): δ 12.2, 22.3, 25.1, 30.6, 32.8, 36.6, 37.5, 41.8, 44.8, 75.5, 113.3, 139.5.

3-isopropyl-1-vinylcyclopentan-1-ol

The compound was prepared according the general procedure and using 3-isopropylcyclopentan-1-one as a cyclic ketone.

GC crude: 94.8% 3-isopropyl-1-vinylcyclopentan-1-ol (57/43 mixture of isomers (cis/trans)).

96.7% purity (GC) after purification (84% yield).

(1SR,3RS)-3-isopropyl-1-vinylcyclopentan-1-ol/(1SR, 3SR)-3-isopropyl-1-vinylcyclopentan-1-ol (57/43 cis/trans)

$^1$H-NMR (500.15 MHz): 0.88 major isomer (d, 3H, J=6.4 Hz), 0.89 minor isomer (d, 1.5H J=6.6 Hz), 0.90 minor isomer (d, 1.5H, J=6.6 Hz), 1.31-1.85 (m, 7.5H), 1.94-2.05 (m, 1.5H), 5.00 major isomer (dd, 0.5H, J=10.7 Hz, J=1.2 Hz), 5.01 minor isomer (dd, 0.5H, J=10.7 Hz, J=1.3 Hz), 5.23 major isomer (dd, 0.5H, J=17.3 Hz, J=1.2 Hz), 5.26 minor isomer (dd, 0.5H, J=17.3 Hz, J=1.3 Hz), 6.01 (dd, 0.5H, J=17.3 Hz, J=10.7 Hz), 6.01 (dd, 0.5H, J=17.3 Hz, J=10.7 Hz).

$^{13}$C NMR (125 MHz, $CDCl_3$): δ 21.2, 21.3, 21.4, 21.6, 28.7, 29.5, 33.7, 34.1, 39.7, 40.8, 45.0, 45.6, 45.6, 46.7, 29.5, 34.0, 40.8, 45.6, 46.7, 82.3, 110.9, 145.0, 81.6, 82.3, 110.5, 110.9, 144.7, 145.0.

b) Step 2: Preparation of Vinyl Acetates from Vinylalcohols (Compounds of Formula (II)

The procedure from example 1 b was used for the vinyl acetate preparation using alcohols prepared in Example 21 a). For the preparation 2-ethyl-4,4-dimethyl-1-vinylcyclohexyl acetate the solvent was switched from toluene to THF and 5 mol % DMAP were used (21% conversion after one day). The crude was purified by flash chromatography or by a distillation through a Vigreux column under reduced pressure.

4-(tert-butyl)-1-vinylcyclohexyl acetate

The compound was prepared according the general procedure and using trans-4-(tert-butyl)-1-vinylcyclohexan-1-ol/cis-4-(tert-butyl)-1-vinylcyclohexan-1-ol as starting alcohol.

GC crude: 89.7% 4-(tert-butyl)-1-vinylcyclohexyl acetate from 4-(tert-butyl)-1-vinylcyclohexan-1-ol (94.0% purity).

98.2% purity (GC) after purification (86% yield).

NMR analysis results in $CDCl_3$ of the trans isomer were in accordance with data from literature (J. C. Fiaud, J. Y. Legros, *J. Organomet. Chem.* 1989, 370, 383).

Trans-4-(tert-butyl)-1-vinylcyclohexyl acetate/Cis-4-(tert-butyl)-1-vinylcyclohexyl acetate (trans/cis 54.5/44.5)

$^1$H-NMR (500.15 MHz): 0.83 major isomer (s, 5H), 0.87 minor isomer (s, 4H), 0.98-1.16 (m, 2H), 1.21-1.29 (m, 1H, 1.32-1.42 (m, 1H), 1.55-1.73 (m, 3H), 1.95 major isomer (s, 1.6H), 2.03 minor isomer (s, 1.4H), 2.34-2.47 (m, 2H), 5.08 (d, 0.5H, J=11.0 Hz), 5.12 (d, 0.5H, J=17.7 Hz), 5.30 (d, 0.5H, J=10.1 Hz), 5.32 (d, 0.5H, J=16.9 Hz), 6.10 minor isomer (dd, 0.5H, J=17.7 Hz, J=11.0 Hz), 6.15 major isomer (dd, 0.5H, J=17.7 Hz, J=10.9 Hz).

Trans-4-(tert-butyl)-1-vinylcyclohexyl acetate $^{13}$C NMR (100 MHz, $CDCl_3$): δ 22.4, 24.1, 27.5, 32.2, 36.0, 47.5, 82.1, 116.6, 139.3, 169.7.

Cis-4-(tert-butyl)-1-vinylcyclohexyl acetate $^{13}$C NMR (100 MHz, $CDCl_3$): δ 22.0, 22.3, 27.5, 32.4, 35.0, 47.0, 81.3, 112.8, 142.3, 169.9.

3-isopropyl-1-vinylcyclohexyl acetate

The compound was prepared according the general procedure and using (1SR,3SR)-3-isopropyl-1-vinylcyclohexan-1-ol/(1SR,3RS)-3-isopropyl-1-vinylcyclohexan-1-ol as starting alcohol (containing 10% 4-isopropyl-1-vinylcyclohexan-1-ol, mixture of trans/cis isomers).

GC crude: 83.8% 3-isopropyl-1-vinylcyclohexyl acetate from 3-isopropyl-1-vinylcyclohexan-1-ol (88.8% purity).

88.7% purity (GC) after purification (83% yield, 42/47 mixture of isomers (cis/trans)). (1SR,3RS-3-isopropyl-1-vinylcyclohexyl acetate/(1SR,3SR)-3-isopropyl-1-vinylcyclohexyl acetate (containing 10% 4-isopropyl-1-vinylcyclohexyl acetate, mixture of trans/cis isomers).

$^1$H-NMR (500.15 MHz): 0.86 (d, 3H, J=5.8 Hz), 0.87 (d, 3H, J=5.8 Hz), 0.90-1.08 (m, 1H), 1.17-1.76 (m, 7H), 1.95 minor isomer (s 1.5H), 2.03 major isomer (s, 1.5H), 2.28-2.45 (m, 2H), 5.08 (d, 0.5H, J=11.0 Hz), 5.12 (d, 0.5H, J=17.7 Hz), 5.28 (d, 0.5H, J=10.0 Hz), 5.31 (d, 0.5H, J=17.1 Hz), 6.10 major isomer (dd, 0.5H, J=17.7 Hz, J=11.0 Hz), 6.16 minor isomer (dd, 0.5H, J=17.8 Hz, J=10.9 Hz).

(1SR,3SR)-3-isopropyl-1-vinylcyclohexyl acetate: trans isomer (major)

$^{13}$C NMR (125 MHz, $CDCl_3$): δ 19.4, 19.7, 21.5, 22.1, 28.4, 32.5, 34.4, 38.4, 38.6, 82.5, 112.6, 142.7, 169.9.

(1SR,3RS)-3-isopropyl-1-vinylcyclohexyl acetate: cis isomer (minor)

$^{13}$C NMR (125 MHz, $CDCl_3$): δ 19.5, 19.7, 22.4, 22.8, 28.8, 32.6, 35.6, 39.4, 40.6, 82.9, 116.4, 139.7, 169.7.

4-isopropyl-1-vinylcyclohexyl acetate (10% in the mixture, mixture of trans/cis isomers):

$^1$H-NMR (500.15 MHz): 1.96 (s, 3H) characteristic signal.

4-butyl-1-vinylcyclohexyl acetate

The compound was prepared according the general procedure and using (trans-4-butyl-1-vinylcyclohexan-1-ol/cis-4-butyl-1-vinylcyclohexan-1-ol as starting alcohol.

GC crude: 95.2% 4-butyl-1-vinylcyclohexyl acetate from 4-butyl-1-vinylcyclohexan-1-ol (95.2% purity).

97.0% purity (GC) after purification (86% yield, 61/36 mixture of isomers (trans/cis)).

trans-4-butyl-1-vinylcyclohexyl acetate/cis-4-butyl-1-vinylcyclohexyl acetate $^1$H-NMR (500.15 MHz): 0.83 (t, 2H, J=7.0 Hz), 0.89 (t, 1H, J=7.0 Hz) 1.02-1.40 (m, 10H), 1.57-1.73 (m, 3H), 1.46-1.57 (m, 3H), 1.96 major isomer (s, 2H), 2.02 minor isomer (s, 1H), 2.20-2.37 (m, 2H), 5.09 (d, 0.4H, J=11.1 Hz), 5.11 (d, 0.4H, J=17.6 Hz), 5.25 (d, 0.6H, J=10.6 Hz), 5.28 (d, 0.6H, J=17.4 Hz), 6.09 minor isomer (dd, 0.4H, J=17.6 Hz, J=11.1 Hz), 6.15 major isomer (dd, 0.6H, J=17.7 Hz, J=11.0 Hz).

$^{13}$C NMR (100 MHz, $CDCl_3$): δ 14.11, 14.13, 22.09, 22.32, 22.94, 22.96, 28.17, 28.97, 29.18, 29.47, 34.54, 34.57, 35.31, 36.05, 36.65, 36.69, 81.66, 82.27, 112.85, 115.93, 139.89, 142.42, 169.82, 169.97.

2-ethyl-4,4-dimethyl-1-vinylcyclohexyl acetate

The compound was prepared according the general procedure (THF as solvent) and using (1SR,2SR)-2-ethyl-4,4-dimethyl-1-vinylcyclohexan-1-ol/(1SR,2RS)-2-ethyl-4,4-dimethyl-1-vinylcyclohexan-1-ol as starting alcohol.

The reaction was performed at 21% conversion (1 day). Unreacted starting material (2-ethyl-4,4-dimethyl-1-vinylcyclohexan-1-ol) was easily recycled by distillation or column chromatography.

95.7% purity (GC) after purification ((49.5/46.2 mixture of isomers (cis/trans)).

(1SR,2SR)-2-ethyl-4,4-dimethyl-1-vinylcyclohexan-1-ol/(1SR,2RS)-2-ethyl-4,4-dimethyl-1-vinylcyclohexan-1-ol (mixture of cis/trans isomers)

$^1$H-NMR (500.15 MHz): 0.79-0.88 (m, 3H), 0.93 (s, 1.5H), 0.94 (s, 3H), 1.02 (s, 1.5H) 1.06-1.47 (m, 4H), 1.57-1.72 (m, 2H), 1.48-1.59 (m, 2H), 2.02 major isomer (s, 1.5H), 2.03 minor isomer (s, 1.5H) 2.06-2.20 (m, 2H), 2.28-2.34 (m, 0.5H). 2.59-2.66 (m, 0.5H), 4.99 (d, 0.5H, J=17.7 Hz), 5.12 (d, 0.5H, J=11.3 Hz), 5.21 (dd, 0.5H, J=17.3 Hz, J=1.4 Hz), 5.24 (dd, 0.5H, J=8.7 Hz, J=2.8 Hz), 5.99 (dd, 0.5H, J=17.3 Hz, J=11.5 Hz), 6.05 (dd, 0.5H, J=15.7 Hz, J=11.3 Hz).

$^{13}$C NMR (100 MHz, $CDCl_3$): δ 12.12, 12.18, 21.90, 21.92, 22.27, 22.60, 24.7, 25.26, 28.68, 29.90, 30.31, 30.90, 32.47, 33.01, 34.20, 36.58, 39.66, 41.46, 41.67, 44.92, 84.92 (minor isomer), 86.65 (major isomer), 112.41, 115.45, 134.51, 142.07, 169.89 (major isomer), 170.11 (minor isomer).

3-isopropyl-1-vinylcyclopentyl acetate

The compound was prepared according the general procedure and using (1SR,3RS)-3-isopropyl-1-vinylcyclopentan-1-ol/(1SR,3SR)-3-isopropyl-1-vinylcyclopentan-1-ol as starting alcohol.

GC crude: 95.4% 3-isopropyl-1-vinylcyclopentyl acetate from 3-isopropyl-1-vinylcyclopentan-1-ol (96.7% purity).

97.5% purity (GC) after purification (94.4% yield, mixture of cis/trans isomers): 59/39.

(1SR,3RS)-3-isopropyl-1-vinylcyclopentyl acetate/(1SR,3SR)-3-isopropyl-1-vinylcyclopentyl acetate $^1$H-NMR (500.15 MHz): 0.88 major isomer (d, 3.6H, J=6.6 Hz), 0.89 minor isomer (d, 1.2H J=6.1 Hz), 0.90 minor isomer (d, 1.2H, J=6.1 Hz), 1.25-1.34 (m, 0.4H), 1.36-1.46 (m, 2H), 1.56-1.65 (m, 0.6H), 1.71-1.99 (m, 3H), 2.00 major isomer (s, 1.2H), 2.01 minor isomer (s, 1.8H), 2.06-2.12 (m, 1H), 2.20-2.25 (m, 0.6H), 2.29-2.34 (m, 0.4H), 5.07 (d, 0.4H, J=10.6 Hz), 5.08 (d, 0.6H, J=11.0 Hz), 5.11 (d, 0.4H, J=18.1 Hz), 5.12 (d, 0.6H, J=17.6 Hz), 6.12 (dd, 0.6H, J=17.8 Hz, J=10.7 Hz), 6.15 (dd, 0.4H, J=17.8 Hz, J=10.9 Hz).

Major Isomer (cis)

$^{13}$C NMR (125 MHz, $CDCl_3$): δ 21.12, 21.29, 22.05, 28.51, 33.64, 37.79, 42.61, 45.38, 89.64, 112.76, 141.04, 170.15.

Minor Isomer (trans)

$^{13}$C NMR (125 MHz, $CDCl_3$): δ 21.28, 21.33, 22.13, 28.55, 33.53, 37.56, 42.84, 45.38, 90.71, 112.64, 140.86, 170.22.

c) Preparation of ((4,4-dimethyl-)-vinylcyclohexyl) oxy)trimethylsilane compounds of Formula (II)

To a stirred solution of 4,4-dimethyl-1-vinyl-cyclohexanol obtained in Example 1 a) (30 g 95.9% purity, 186.5 mmol) in dichloromethane (750 mL) was added under water cooling triethylamine (56.62 g, 559.6 mmol, 3 eq) and chlorotrimethylsilane (28.37 g 261.1 mmol, 1.4 eq) under $N_2$. After 22 h at room temperature a full conversion of starting material was observed. A saturated aqueous $NaHCO_3$ solution (750 mL) was added slowly and the organic phase was separated. The aqueous phase was extracted twice with 500 mL diethyl ether and with 250 mL dichloromethane. The combined organic phases were washed with a saturated aqueous NaCl solution and dried over sodium sulfate. The solvent was evaporated under reduced pressure (40° C., 500-4.8 mbar). A red solid of the crude (44.8 g, 96.1% purity) was filtered off (crude 40.9 g).

The crude was purified by distillation (Vigreux) 0.2-0.099 mbar, bp 32.6-36.7° C., wok 70° C., curve 83° C.). ((4,4-dimethyl-1-vinylcyclohexyl)oxy)trimethylsilane was isolated in 94.5% yield (40.0 g, 99.8% purity, 176.3 mmol).

$^1$H-NMR (500.15 MHz): 0.09 (s, 9H), 0.86 (s, 3H), 0.93 (s, 3H), 1.14-1.12 (m, 2H), 1.46-1.63 (m, 6H), 5.03 (d, 1H, J=10.8 Hz), 5.15 (d, 1H, J=17.6 Hz), 5.95 (1H, dd, J=17.7 Hz, J=10.8 Hz).

$^{13}$C NMR (125 MHz, $CDCl_3$): δ 2.6, 26.3, 29.5, 33.5, 34.0, 35.1, 74.3, 112.2, 145.8.

Example 22

Preparation of different compounds of formula (I)

a) Preparation of 3-(4-(tert-butyl)cyclohex-1-en-1-yl)propanal

Step 1: Hydroformylation of (4-tert-butyl-1-vinyl-cyclohexyl) acetate with BIPHEPHOS-Rh The autoclave was charged with (4-tert-butyl-1-vinylcyclohexyl) acetate (trans/cis ratio: 54.5%/44.5%, 5.06 g, 22.56 mmol), $Rh(CO)_2acac$ (3.2 mg, 0.0124 mmol) and BiPhePhos (26.8 mg, 0.034 mmol). The vessel was purged with $H_2/CO$ (1:1, 4×5 bar) and heated under vigorous stirring at 90° C. and 10 bar syngas pressure for 24h. After cooling and depressurization, GLC analysis (DB-1, 10 meters, 100 microns, 80° C., 1 min; 40°/min. to 240° C.; 5 min. or DB-WAX, 10 meters, 100 microns, 80° C., 1 min.; 40°/min. to 240° C.; 5 min.) of the semi-crystallized crude revealed total conversion and the presence of 4-(tert-butyl)-1-(3-oxopropyl)cyclohexyl acetate (92.2%; trans/cis ratio: 54.4%/37.8%).

cis-4-(tert-butyl)-1-(3-oxopropyl)cyclohexyl acetate:

$^1$H-NMR (600.15 MHz): δ 0.85 (s, 9H, 4-(C($CH_3$)$_3$), 1.14-1.24 (m, 4H), 1.55-1.66 (m, 3H), 2.02 (s, 3H, $COCH_3$), 2.21 (t, 2H) 2.33-2.37 (m, 2H, H-1'), 2.43 (t, 2H, H-2'), 9.74 (t, 1H, $^2J_{1,2}$=1.54 Hz, H-1).

$^{13}$C NMR (125 MHz, $CDCl_3$): δ 22.1 (q), 22.2 (t), 27.4 (q), 30.4 (t), 32.3 (s), 34.8 (t), 38.3 (t), 47.2 (d), 82.2 (s), 170.4 (s), 202.0 (d).

trans-4-(tert-butyl)-1-(3-oxopropyl)cyclohexyl acetate:

$^1$H-NMR (600.15 MHz): δ 0.85 (s, 9H, 4-(C($CH_3$)$_3$), 1.06-1.16 (m, 3H), 1.67-1.77 (m, 4H), 1.97 (s, 3H, $COCH_3$), 2.13-2.19 (m, 2H), 2.27-2.32 (m, 2H, H-1'), 2.40-2.46 (m, 2H, H-2'), 9.78 (t, 1H, $^2J_{1,2}$=1.60 Hz, H-1').

$^{13}$C NMR (100 MHz, $CDCl_3$): δ 22.4 (q), 23.9 (t), 24.8 (t), 27.6 (q), 32.2 (s), 34.6 (t), 38.3 (t), 47.3 (d), 84.2 (s), 170.3 (s), 202.0 (d).

Step 2: Preparation of trans-1-(2-(1,3-dioxolan-2-yl)ethyl)-4-(tert-butyl)cyclohexyl acetate/cis-1-(2-(1,3-dioxolan-2-yl)ethyl)-4-(tert-butyl)cyclohexyl acetate The compound was prepared according to the procedure reported in Example 10 using, as a starting material, the compound prepared in the previous step.

GC crude: 52.0%/30.6% 1-(2-(1,3-dioxolan-2-yl)ethyl)-4-(tert-butyl)cyclohexyl acetate from 4-(tert-butyl)-1-(3-oxopropyl)cyclohexyl acetate (54.4%/37.8%). 55.2%/38.3% purity (GC) after purification. Product contains 2.6% 4-(tert-butyl)-1-(3-oxopropyl)cyclohexyl acetate and 3.9% trans-4-(tert-butyl)-1-(3-oxopropyl)cyclohexyl acetate.

1-(2-(1,3-dioxolan-2-yl)ethyl)-4-(tert-butyl)cyclohexyl acetate $^1$H-NMR (500.15 MHz): 0.85 (s, 9H), 0.97-1.27 (m, 4H, 1.55-1.72 (m, 6H), 1.92 (trans isomer) and 2.00 (cis isomer) (s, 3H), 2.04-2.10 (m, 1H), 2.18-2.27 (m, 1H), 2.33-2.45 (m, 1H), 3.80-3.87 (m, 2H), 3.94-4.00 (m, 2H), 4.82 (cis isomer) and 4.85 (trans isomer) (t, 1H, J=4.8 Hz).

Trans Isomer (major)

$^{13}$C NMR (125 MHz, $CDCl_3$): δ 22.5, 23.9, 26.3, 27.6, 27.7, 32.2, 34.9, 47.4, 64.9, 84.6, 104.6, 170.3.

Cis Isomer (minor)

$^{13}$C NMR (125 MHz, $CDCl_3$): δ 22.1, 22.3, 27.5, 27.9, 32.4, 32.5, 34.8, 47.3, 64.9, 82.7, 104.6, 170.3.

Step 3: Preparation of 2-(2-(4-(tert-butyl)cyclohex-1-en-1-yl)ethyl)-1,3-dioxolane To a solution of the dioxolane acetate prepared in previous step (3.126 mmol) in 5 mL dry Toluene was added 0.15 eq of $BF_3 \cdot Et_2O$. The mixture was stirred at RT for 30 min (full conversion of starting material) and was then added to 20 mL of a saturated aqueous $NaHCO_3$ solution. When no more gas formation was observed 15 mL MTBE was added and the mixture was stirred for 10 minutes. The organic phase was separated and was washed with water and a saturated aqueous NaCl solution. After drying over $Na_2SO_4$ the solvent was evaporated under reduced pressure (500-50 mbar, 50° C.). The crude was purified by flash chromatography GC crude: 91.8% 2-(2-(4-(tert-butyl)cyclohex-1-en-1-yl)ethyl)-1,3-dioxolane/3.7% 2-(2-(4-(tert-butyl)cyclohexylidene)ethyl)-1,3-dioxolane from 1-(2-(1,3-dioxolan-2-yl)ethyl)-4-(tert-butyl)cyclohexyl acetate (93.5% purity).

94.0%/3.5% purity (GC) after purification.

2-(2-(4-(tert-butyl)cyclohex-1-en-1-yl)ethyl)-1,3-dioxolane $^1$H-NMR (500.15 MHz): 0.86 (s, 9H), 1.10-1.26 (m, 2H), 1.71-1.84 (m, 4H), 1.94-2.08 (m, 5H), 3.82-3.89 (m, 2H), 3.93-4.00 (m, 2H), 4.85 (t, 1H, J=4.9 Hz), 5.40-5.44 (m, 1H).

$^{13}$C NMR (90 MHz, $CDCl_3$): δ 24.3, 26.8, 27.2, 29.9, 31.7, 32.2, 32.2, 44.2, 64.8, 104.4, 121.2, 136.7.

Step 4: Preparation of 3-(4-(tert-butyl)cyclohex-1-en-1-yl)propanal

The compound was prepared according to procedure reported in Example 13 using, as a starting material, the compound prepared in the previous step.

The $^1$H and $^{13}$C-NMR analysis results in $CDCl_3$ were in accordance with data from literature (see B. Winter EP 1054053 A2).

3-(4-(tert-butyl)cyclohex-1-en-1-yl)propanal $^{13}$C NMR (90 MHz, $CDCl_3$): δ 24.1, 26.8, 27.2, 29.7, 29.9, 32.2, 41.9, 44.0, 122.1, 135.5, 202.8.

b) Preparation of 3-(S-isopropylcyclohex-1-en-1-yl)propanal/3-(3-isopropylcyclohex-1-en-1-yl)propanal

Step 1: Hydroformylation of (3-isopropyl-1-vinyl-cyclohexyl) acetate with BIPHEPHOS-Rh The autoclave was charged with a mixture of 3-isopropyl-1-vinyl-cyclohexyl acetate (1SR,3RS/1SR,3SR, 42%/47%) and 4-isopropyl-1-vinyl-cyclohexyl acetate (cis/trans, 4%/6.5%) (5.04 g, 23.965 mmol), $Rh(CO)_2acac$ (2.5 mg, 0.0119 mmol) and BiPhePhos (28.7 mg, 0.0365 mmol). The vessel was purged with $H_2/CO$ (1:1, 4×5 bar) and heated under vigorous stirring at 90° C. and 10 bar syngas pressure for 24h. After cooling and depressurization, GLC analysis of the crude colorless oil revealed total conversion and the presence of the linear 3-isopropyl-1-(3-oxopropyl)cyclohexyl acetate (1SR,3SR/1SR,3RS, 39.7%/45.3%) and 4-isopropyl-1-(3-oxopropyl)cyclohexyl acetate (cis/trans, 4%/6.3%).

1SR,3SR/1SR,3RS-3-isopropyl-1-(3-oxopropyl)cyclohexyl acetates $^1$H-NMR (500.15 MHz): δ 0.83-0.88 (m, 6H), 0.89-1.01 (m, 1H), 1.04-1.51 (m, 4H), 1.57-1.79 (m, 3H), 1.95-2.03 (2×s, 3H, $COCH_3$), 2.04-2.14 (m, 1H), 2.17-2.37 (m, 3H), 2.41-2.47 (m, 2H), 9.78 (t, $^2J_{1,2}$=1.60 Hz), 9.75 (t, $^2J_{1,2}$=1.76 Hz) both aldehyde proton signals together 1H.

$^{13}$C NMR (125 MHz, $CDCl_3$): δ 19.4 (q), 19.6 (q), 19.74 (q), 19.75 (q), 21.5 (t), 22.2 (q), 22.5 (q), 22.7 (t), 25.6 (t), 28.5 (t), 28.7 (t), 30.9 (t), 32.4 (d), 32.7 (d), 34.4 (t), 34.5 (t), 37.9 (t), 38.0 (t), 38.2 (t), 38.3 (t), 38.6 (d), 40.6 (d), 83.4 (s), 85.1 (s), 170.27 (s), 170.33 (s), 201.93 (s), 201.96 (s).

Step 2: Preparation of 1-(2-(1,3-dioxolan-2-yl)ethyl)-3-isopropylcyclohexyl acetate The compound was prepared according to the procedure reported in Example 10 using, as a starting material, the compound prepared in the previous step.

GC crude: 40.5%/46.1% 1-(2-(1,3-dioxolan-2-yl)ethyl)-3-isopropylcyclohexyl acetate and 2.7% 2-(2-(5-isopropyl-cyclohex-1-en-1-yl)ethyl)-1,3-dioxolane from 3-isopropyl-1-(3-oxopropyl)cyclohexyl acetate (39.7%/45.3%).

41.9%/47.4% purity (GC) after purification (the product contained 10% 1-(2-(1,3-dioxolan-2-yl)ethyl)-4-isopropyl-cyclohexyl acetate, mixture of trans/cis isomers).

(1SR,3RS)-1-(2-(1,3-dioxolan-2-yl)ethyl)-3-isopropylcyclohexyl acetate (major isomer)

(1SR,3SR)-1-(2-(1,3-dioxolan-2-yl)ethyl)-3-isopropylcyclohexyl acetate (minor isomer)

$^1$H-NMR (500.15 MHz): 0.83-0.86 (m, 6H), 0.89-1.49 (m, 5H), 1.54-1.74 (m, 5H), 1.87 (cis isomer) and 2.00 (trans isomer) (s, 3H), 1.98-2.19 (m, 3H), 2.28-2.37 (m, 1H), 3.81-3.88 (m, 2H), 3.93-4.00 (m, 2H), 4.83 (cis isomer) and 4.85 (trans isomer) (t, 1H, J=4.8 Hz).

$^{13}$C NMR (100 MHz, $CDCl_3$): δ 19.37, 19.64, 19.74, 19.76, 21.58, 22.20, 22.54, 22.71, 27.12, 27.65, 27.83, 28.59, 28.78, 32.47, 32.69, 32.96, 34.46, 34.65, 38.07, 38.13, 38.62, 40.51, 64.90 (2C), 83.82, 85.52, 104.58, 104.62, 170.23, 170.27.

1-(2-(1,3-dioxolan-2-yl)ethyl)-4-isopropylcyclohexyl acetate (characteristic signals, mixture of trans/cis isomers)

$^{13}$C NMR (100 MHz, $CDCl_3$): δ 19.85, 20.18, 22.14, 22.45, 24.81, 26.05, 26.99, 27.68, 27.86, 31.69, 32.50, 34.07, 34.53, 43.00 (major isomer), 43.31 (minor isomer), 64.90, 82.89 (minor isomer), 84.58 (major isomer), 104.56, 104.60, 170.30, 170.33.

Step 3: Preparation of 2-(2-(5-isopropylcyclohex-1-en-1-yl)ethyl)-1,3-dioxolane/2-(2-(3-isopropylcyclohex-1-en-1-yl)ethyl)-1,3-dioxolane The compound was prepared according to the procedure reported for the preparation of 2-(2-(4-(tert-butyl)cyclohex-1-en-1-yl)ethyl)-1,3-dioxolane using, as a starting material, the compound prepared in the previous step.

GC crude: 55.8% 2-(2-(5-isopropylcyclohex-1-en-1-yl)ethyl)-1,3-dioxolane, 23.9% 2-(2-(3-isopropylcyclohex-1-en-1-yl)ethyl)-1,3-dioxolane, 7.2% 2-(2-(3-isopropylcyclohexylidene)ethyl)-1,3-dioxolane from 1-(2-(1,3-dioxolan-2-yl)ethyl)-3-isopropylcyclohexyl acetate 41.9%/47.4%

57.2%/24.7%/7.3% purity (GC) after purification (the product contained 10% of 2-(2-(4-isopropylcyclohex-1-en-1-yl)ethyl)-1,3-dioxolane).

2-(2-(5-isopropylcyclohex-1-en-1-yl)ethyl)-1,3-dioxolane (major isomer)/2-(2-(3-isopropylcyclohex-1-en-1-yl)ethyl)-1,3-dioxolane (minor isomer)

$^1$H-NMR (500.15 MHz): 0.82-0.92 (m, 6H), 1.06-1.35 (m, 2H), 1.39-1.59 (m, 1H), 1.63-2.10 (m, 9H), 3.81-3.90 (m, 2H), 3.91-4.00 (m, 2H), 4.85 (minor isomer) and 4.86 (major isomer) (t, 1H, J=4.8 Hz), 5.34 (m, 0.3H), 5.41 (m, 0.7H).

2-(2-(5-isopropylcyclohex-1-en-1-yl)ethyl)-1,3-dioxolane (major isomer)

$^{13}$C NMR (125 MHz, $CDCl_3$): δ 19.6, 19.9, 25.9, 26.0, 32.1, 32.2, 32.2, 32.4, 40.5, 64.9, 104.5, 120.8, 136.8.

2-(2-(3-isopropylcyclohex-1-en-1-yl)ethyl)-1,3-dioxolane (minor isomer)

$^{13}$C NMR (125 MHz, $CDCl_3$): δ 19.3, 19.6, 22.6, 25.4, 28.7, 32.2, 32.3, 32.4, 41.8, 64.9, 104.4, 124.9, 137.2.

2-(2-(4-isopropylcyclohex-1-en-1-yl)ethyl)-1,3-dioxolane (10% in the mixture).

$^{13}$C NMR (100 MHz, $CDCl_3$): δ 19.7, 20.0, 26.4, 28.9, 29.1, 31.8, 32.2, 32.3, 40.2, 64.8, 104.6, 120.9, 136.7.

Step 4: Preparation of 3-(5-isopropylcyclohex-1-en-1-yl)propanal/3-(3-isopropylcyclohex-1-en-1-yl)propanal/3-(4-butylcyclohex-1-en-1-yl)propanal The compound (7/3 mixture) was prepared according to procedure reported in Example 13 using, as a starting material, the compound prepared in the previous step. The $^1$H and $^{13}$C-NMR analysis results in $CDCl_3$ were in accordance with data from literature (see R. Moretti, A. Birkbeck WO 2017046071 A1).

3-(5-isopropylcyclohex-1-en-1-yl)propanal (major isomer)

$^{13}$C NMR (125 MHz, $CDCl_3$): δ 19.6, 19.9, 25.8, 25.9, 30.1, 32.3, 32.3, 40.4, 41.9, 121.7, 135.6, 202.8.

3-(3-isopropylcyclohex-1-en-1-yl)propanal (minor isomer)

$^{13}$C NMR (125 MHz, $CDCl_3$): δ 19.3, 19.7, 22.4, 25.2, 28.7, 30.4, 32.3, 41.8, 42.0, 125.8, 136.1, 202.8.

3-(4-isopropylcyclohex-1-en-1-yl)propanal (10% in the mixture)

NMR analysis results in $CDCl_3$ were in accordance with data from literature (E. Singer, B, Holscher, US2013/90390, 2013, A1).

$^{13}$C NMR (90 MHz, $CDCl_3$): δ 19.7, 19.9, 26.3, 28.9, 29.2, 29.8, 32.2, 40.0, 41.9, 121.8, 135.6, 202.8.

c) Preparation of 3-(4-butylcyclohex-1-en-1-yl)propanal

Step 1: Hydroformylation of (4-butyl-1-vinylcyclohexyl acetate with BIPHEPHOS-Rh The autoclave was charged with a mixture of (4-butyl-1-vinyl-cyclohexyl) acetate (cis/trans, 36%/61%, 5.06 g, 22.555 mmol), $Rh(CO)_2acac$ (3.1 mg, 0.012 mmol) and BiPhePhos (26.3 mg, 0.0334 mmol). The vessel was purged with $H_2$/CO (1:1, 4×5 bar) and heated under vigorous stirring at 90° C. and 10 bar syngas pressure for 24h. After cooling and depressurization, GLC analysis of the crude colorless oil revealed total conversion and the presence of the linear 4-butyl-1-(3-oxopropyl)cyclohexyl acetate (89.9%, cis/trans, 33.2%/56.7%.

4-butyl-1-(3-oxopropyl)cyclohexyl acetates:

$^1$H-NMR (500.15 MHz): δ 0.85-0.92 (m, 3H), 1.03-1.14 (m, 2H), 1.15-1.40 (m, 8H), 1.55-1.62 (m, 1H), 1.64-1.72 (m, 1H), 1.77-1.84 (m, 1H), 1.93-1.97 (m, 1H), 1.98, 2.02 (2×s, 3H, $COCH_3$), 2.20-2.25 (m, 1H), 2.27-2.34 (m, 2H), 2.40-2.46 (m, 2H), 9.77 (t, 1H, $^2J_{1,2}$=1.60 Hz, H-1), 9.75 (t, 1H, $^2J_{1,2}$=1.76 Hz, H-1) both aldehyde proton signals together 1H.

$^{13}$C NMR (125 MHz, $CDCl_3$): δ 14.10, 14.11 (q), 22.12, 22.42 (q), 22.92, 22.95 (t). 25.92 (t), 28.1, 28.75 (t), 29.15, 29.46 (t), 30.45, 33.32, 34.38, 35.16 (t), 35.87 (d), 36.66 (t), 36.80 (d), 38.25, 38.29 (t), 82.56, 84.17 (s), 170.35, 170.4 (s), 201.95, 201.98 (s).

Step 2: Preparation of 1-(2-(1,3-dioxolan-2-yl)ethyl)-4-butylcyclohexyl acetate The compound was prepared according to procedure reported in Example 10 using, as a starting material, the compound prepared in the previous step.

GC crude: 50.1%/31.7% 1-(2-(1,3-dioxolan-2-yl)ethyl)-4-butylcyclohexyl acetate and 4.3% 2-(2-(4-butylcyclohex-1-en-1-yl)ethyl)-1,3-dioxolane/1.8% 2-(2-(4-butylcyclohexylidene)ethyl)-1,3-dioxolane from 4-butyl-1-(3-oxopropyl) cyclohexyl acetates (33.2%/56.7%).

33.8%/66.2% purity (GC) after purification.

(2-(4-(tert-butyl)cyclohex-1-en-1-yl)ethyl)-1,3-dioxolane $^{1}$H-NMR (500.15 MHz): 0.88 and 0.89 (t, 3H, J=7.0 Hz), 1.03-1.14 (m, 2H), 1.15-1.38 (m, 8H), 1.53-1.78 (m, 6H), 1.97 (trans isomer) and 2.00 (cis isomer) (s, 3H), 1.99-2.09 (m, 2.4H), 2.30-2.36 (m, 0.6H), 3.81-3.88 (m 2H), 3.93-4.00 (m, 2H), 4.82 (cis isomer) and 4.84 (trans isomer) (t, 1H, J=4.8 Hz).

Major Isomer Trans $^{13}$C NMR (125 MHz, $CDCl_3$): δ 14.1, 22.4, 22.9, 27.7, 28.2, 28.8, 29.5, 33.5, 34.4, 35.9, 64.9, 84.5, 104.6, 170.3.

Minor Isomer Cis $^{13}$C NMR (125 MHz, $CDCl_3$): δ 14.1, 22.2, 23.0, 27.6, 27.9, 29.2, 32.5, 35.2, 36.7, 36.9, 64.9, 83.0, 104.6, 170.3.

Step 3: Preparation of 2-(2-(4-butylcyclohex-1-en-1-yl)ethyl)-1,3-dioxolane

The compound was prepared according to the procedure reported for the preparation of 2-(2-(4-(tert-butyl)cyclohex-1-en-1-yl)ethyl)-1,3-dioxolane using, as a starting material, the compound prepared in the previous step.

GC crude: 91.2% 2-(2-(4-butylcyclohex-1-en-1-yl)ethyl)-1,3-dioxolane/5.2% 2-(2-(4-butylcyclohexylidene)ethyl)-1,3-dioxolane from 1-(2-(1,3-dioxolan-2-yl)ethyl)-4-butylcyclohexyl acetate (33.8%/66.2% purity).

92.9%/5.8% purity (GC) after purification.

2-(2-(4-butylcyclohex-1-en-1-yl)ethyl)-1,3-dioxolane $^{1}$H-NMR (500.15 MHz): 0.89 (t, 3H, J=7.0 Hz), 1.14-1.34 (m, 7H), 1.39-1.40 (m, 1H), 1.55-1.65 (m, 1H), 1.70-1.79 (m, 3H), 1.89-2.12 (m, 5H), 3.82-3.89 (m, 2H), 3.92-4.01 (m, 2H), 4.85 (t, 1H, J=4.8 Hz), 5.38-5.42 (m, 1H).

$^{13}$C NMR (125 MHz, $CDCl_3$): δ 14.2, 23.0, 28.5, 29.3, 29.4, 31.9, 32.1, 32.2, 33.5, 36.2, 64.9, 104.5, 120.6, 136.8.

Step 4: Preparation of 3-(4-butylcyclohex-1-en-1-yl)propanal

The compound was prepared according to procedure reported in Example 13 using, as a starting material, the compound prepared in the previous step. The $^{1}$H and $^{13}$C-NMR analysis results in $CDCl_3$ were in accordance with data from literature (see R. Moretti WO 2019185599 A1).

3-(4-butylcyclohex-1-en-1-yl)propanal $^{13}$C NMR (125 MHz, $CDCl_3$): δ 14.1, 23.0, 28.6, 29.2, 29.2, 29.9, 32.0, 33.4, 36.1, 41.9, 121.5, 135.6, 202.8.

d) Preparation of 3-(2-ethyl-4,4-dimethylcyclohex-1-en-1-yl)propanal/3-(6-ethyl-4,4-dimethylcyclohex-1-en-1-yl)propanal

Step 1: Hydroformylation of 2-ethyl-4,4-dimethyl-1-vinyl-cyclohexyl acetate with BIPHEPHOS-Rh The autoclave was charged with a mixture of (1SR,2SR)- and (1SR,2RS)-2-ethyl-4,4-dimethyl-1-vinyl-cyclohexyl acetate (49.5%/46.2%, 3.02 g, 13.462 mmol), $Rh(CO)_2acac$ (2.1 mg, 0.0081 mmol) and BiPhePhos (16.8 mg, 0.0214 mmol). The vessel was purged with $H_2/CO$ (1:1, 4×5 bar) and heated under vigorous stirring at 90° C. and 10 bar syngas pressure for 24h. After cooling and depressurization, GLC analysis of the crude yellow oil revealed total conversion and the presence of the linear (1SR,2SR)- and (1SR,2RS)-2-ethyl-4,4-dimethyl-1-(3-oxopropyl)cyclohexyl acetates (49%/42%).

(1SR,2SR)- and (1SR,2RS)-2-ethyl-4,4-dimethyl-1-(3-oxopropyl)cyclohexyl acetates:

$^{1}$H-NMR (500.15 MHz): δ 0.82-1.06 (m, 11H), 1.11-1.25 (m, 2H), 1.26-1.38 (m, 1H), 1.40-1.62 (m, 2H), 1.62-1.67 (dt, 1H), 1.91-2.09 (m, 4H), 2.37-2.73 (m, 4H), 9.78 (t, 1H, $^{2}J_{1,2}$=1.60 Hz, H-1), 9.75 (t, 1H, $^{2}J_{1,2}$=1.76 Hz) both aldehyde proton signals together 1H.

$^{13}$C NMR (125 MHz, $CDCl_3$): δ 11.97, 12.29 (q), 21.23, 21.87 (t), 22.11 (q), 22.53 (t), 22.67, 24.74, 25.70 (q), 27.14, 27.85, 28.00 (t), 29.82, 30.45 (s), 32.28, 32.91, 34.39, 36.32, 38.37, 39.20 (t), 39.48, 41.14 (d), 41.95 (t), 85.28, 88.31, 170.28, 170.56 (s), 201.52, 202.39 (d).

Step 2: Preparation of 1-(2-(1,3-dioxolan-2-yl)ethyl)-2-ethyl-4,4-dimethylcyclohexyl acetate The compound was prepared according to procedure reported in Example 10 using, as a starting material, the compound prepared in the previous step.

GC crude: 44.1%/38.4% 1-(2-(1,3-dioxolan-2-yl)ethyl)-2-ethyl-4,4-dimethylcyclohexyl acetate and 2-(2-(2-ethyl-4,4-dimethylcyclohex-1-en-1-yl)ethyl)-1,3-dioxolane/2-(2-(6-ethyl-4,4-dimethylcyclohex-1-en-1-yl)ethyl)-1,3-dioxolane (5.6%/2.6%) from 2-ethyl-4,4-dimethyl-1-(3-oxopropyl)cyclohexyl acetates 49%/42%.

51.9%/45.3% purity (GC) after purification (contains 2.7% 2-ethyl-4,4-dimethyl-1-(3-oxopropyl)cyclohexyl acetates).

1-(2-(1,3-dioxolan-2-yl)ethyl)-2-ethyl-4,4-dimethylcyclohexyl acetate $^{1}$H-NMR (500.15 MHz): 0.85 major isomer (t, 1.5H, J=7.3 Hz), 0.86 minor isomer (t, 1.5H, J=7.5 Hz), 0.88 (s, 1.5H), 0.91 (s, 3H), 0.93-1.00 (m, 1H), 1.02 (s, 1.5H), 1.10-1.37 (m, 4H), 1.43-1.73 (m, 5H), 1.78-1.90 (m, 1H), 1.97 (s, 3H), 2.44-2.69 (m, 2H), 3.82-3.91 (m, 2H), 3.93-4.02 (m, 2H), 4.83 major isomer (t, 0.5H, J=4.6 Hz), 4.85 minor isomer (t, 0.5H, J=4.2 Hz).

(1SR,2SR)-1-(2-(1,3-dioxolan-2-yl)ethyl)-2-ethyl-4,4-dimethylcyclohexyl acetate (major isomer)

$^{13}$C NMR (125 MHz, $CDCl_3$): δ 12.3, 21.9, 22.8, 24.4, 24.7, 27.7, 29.8, 30.4, 33.0, 34.5, 39.1, 39.5, 64.9, 88.7, 104.9, 170.6.

(1SR,2RS)-1-(2-(1,3-dioxolan-2-yl)ethyl)-2-ethyl-4,4-dimethylcyclohexyl acetate (minor isomer)

$^{13}$C NMR (125 MHz, $CDCl_3$): δ 11.9, 21.1, 22.2, 25.9, 27.1, 27.7, 29.2, 29.9, 32.3, 36.3, 40.2, 41.9, 64.9, 86.1, 104.5, 170.4.

Step 3: Preparation of 2-(2-(2-ethyl-4,4-dimethylcyclohex-1-en-1-yl)ethyl)-1,3-dioxolane/2-(2-(6-ethyl-4,4-dimethylcyclohex-1-en-1-yl)ethyl)-1,3-dioxolane The compound was prepared according to the procedure reported for the preparation of 2-(2-(4-(tert-butyl)cyclohex-1-en-1-yl)ethyl)-1,3-dioxolane using, as a starting material, the compound prepared in the previous step.

GC crude: 71.9%/13.8% 2-(2-(2-ethyl-4,4-dimethylcyclohex-1-en-1-yl)ethyl)-1,3-dioxolane/2-(2-(6-ethyl-4,4-dimethylcyclohex-1-en-1-yl)ethyl)-1,3-dioxolane and 2.9% 2-(2-(2-ethyl-4,4-dimethylcyclohexylidene)ethyl)-1,3-dioxolane from 1-(2-(1,3-dioxolan-2-yl)ethyl)-2-ethyl-4,4-dimethylcyclohexyl acetate (51.9%/45.3% purity).

81.8%/15.4%/2.7% purity (GC) after purification.

2-(2-(2-ethyl-4,4-dimethylcyclohex-1-en-1-yl)ethyl)-1,3-dioxolane/2-(2-(6-ethyl-4,4-dimethylcyclohex-1-en-1-yl)ethyl)-1,3-dioxolane $^1$H-NMR (500.15 MHz): 0.83 minor isomer (t, 0.5H, J=7.4 Hz), 0.86 major isomer (s, 5H), 0.92 major isomer (t, 2.5H, J=7.5 Hz), 0.93 minor isomer (s, 1H), 1.31 major isomer (t, 1.7H, J=6.5 Hz), 1.39-1.45 (m, 0.15H), 1.59-1.73 (m, 4.3H), 1.75-1.87 (m, 0.3H), 1.93-2.01 (m, 3.4H), 2.11 (t, 2H, J=8.5 Hz), 3.81-3.89 (m, 2H), 3.93-4.01 (m, 2H), 4.83 major isomer (t, 0.85H, J=4.6 Hz), 4.86 minor isomer (t, 0.15H, J=4.2 Hz), 5.39-5.42 minor isomer (m, 0.15H).

2-(2-(2-ethyl-4,4-dimethylcyclohex-1-en-1-yl)ethyl)-1,3-dioxolane (major isomer)

$^{13}$C NMR (125 MHz, $CDCl_3$): δ 13.0, 26.0, 26.9, 27.2, 28.1, 28.1, 29.0, 32.9, 35.9, 43.0, 64.9, 104.5, 126.8, 131.4.

2-(2-(6-ethyl-4,4-dimethylcyclohex-1-en-1-yl)ethyl)-1,3-dioxolane (minor isomer)

$^{13}$C NMR (125 MHz, $CDCl_3$): δ 10.4, 24.9, 25.0, 28.9, 29.2, 31.9, 32.5, 35.5, 39.5, 41.5, 64.9, 104.5, 121.7, 138.2.

Step 4: Preparation of 3-(2-ethyl-4,4-dimethylcyclohex-1-en-1-yl)propanal and 3-(6-ethyl-4,4-dimethylcyclohex-1-en-1-yl)propanal The compound (84/16 mixture) was prepared according to procedure reported in Example 13 using, as a starting material, the compound prepared in the previous step.

3-(2-ethyl-4,4-dimethylcyclohex-1-en-1-yl)propanal (major isomer)

$^{13}$C NMR (125 MHz, $CDCl_3$): δ 13.0, 25.1, 26.1, 27.0, 28.1, 29.0, 35.8, 43.0, 43.1, 125.5, 132.6, 202.8.

3-(6-ethyl-4,4-dimethylcyclohex-1-en-1-yl)propanal (minor isomer)

C NMR (125 MHz, $CDCl_3$): δ 10.2, 24.9, 24.9, 27.0, 29.2, 32.0, 35.7, 39.4, 41.4, 122.7, 137.0, 202.8.

e) Preparation of 3-(4-isopropylcyclopent-1-en-1-yl)propanal/3-(3-isopropylcyclopent-1-en-1-yl)propanal Step 1: Hydroformylation of 3-isopropyl-1-vinylcyclopentyl acetate with BIPHEPHOS-Rh The autoclave was charged with a mixture of (1SR,3RS)- and (1SR,3SR)-(3-isopropyl-1-vinyl-cyclopentyl) acetate (59%/39%, 5.02 g, 25.574 mmol), [Rh(CO)$_2$acac] (3.3 mg, 0.0128 mmol) and BiPhePhos (30.7 mg, 0.039 mmol). The vessel was purged with $H_2$/CO (1:1, 4×5 bar) and heated under vigorous stirring at 90° C. and 10 bar syngas pressure for 24h. After cooling and depressurization, GLC analysis of the crude yellow oil revealed total conversion and the presence of the linear (1SR,3SR)- and (1SR,3RS)-3-isopropyl-1-(3-oxopropyl)cyclopentyl acetates (57%/35%).

(1SR,3SR)- and (1SR,3RS)-3-isopropyl-1-(3-oxopropyl)cyclopentyl acetates:

$^1$H-NMR (500.15 MHz): δ 0.86-0.90 (m, 6H), 1.14-1.25 (m, 1H), 1.33-1.46 (m, 1H), 1.50-1.63 (m, 1H), 1.70-1.89 (m, 3H), 1.97-2.00 (2×s, 3H, $COCH_3$), 2.00-2.32 (m, 3H), 2.33-2.42 (m, 1H), 2.42-2.48 (m, 2H), 9.75 (m, 1H).

(1SR,3SR)-3-isopropyl-1-(3-oxopropyl)cyclopentyl acetate (major)

$^{13}$C NMR (125 MHz, $CDCl_3$): δ 21.2 (q), 21.4 (q), 22.1 (q), 28.9 (t), 30.2 (t), 33.5 (d), 37.7 (t), 39.4 (t), 42.6 (t), 46.2 (d), 91.0 (s), 170.5 (s), 201.9 (d).

(1SR,3RS)-3-isopropyl-1-(3-oxopropyl)cyclopentyl acetate (minor)

$^{13}$C NMR (125 MHz, $CDCl_3$): δ 21.2 (q), 21.4 (q), 22.2 (q), 29.0 (t), 30.1 (t), 33.5 (d), 37.4 (t), 39.5 (t), 42.7 (t), 45.6 (d), 91.7 (s), 170.6 (s), 201.8 (d).

Step 2: Preparation of 1-(2-(1,3-dioxolan-2-yl)ethyl)-3-isopropylcyclopentyl acetate The compound was prepared according to procedure reported in Example 10 using, as a starting material, the compound prepared in the previous step.

GC crude: 38.2%/27.6% 1-(2-(1,3-dioxolan-2-yl)ethyl)-3-isopropylcyclopentyl acetate and 7.3%/6.0 2-(2-(4-isopropylcyclopent-1-en-1-yl)ethyl)-1,3-dioxolane/2-(2-(3-isopropylcyclopent-1-en-1-yl)ethyl)-1,3-dioxolane from 3-isopropyl-1-(3-oxopropyl)cyclopentyl acetates (57%/35%).

57.4%/41.6% purity (GC) after purification.

1-(2-(1,3-dioxolan-2-yl)ethyl)-3-isopropylcyclopentyl acetate $^1$H-NMR (500.15 MHz): 0.85-0.89 (m, 6H), 1.15-1.44 (m, 2H), 1.48-1.88 (m, 6H), 1.88-1.98 (m, 1H), 1.97 (major isomer) and 1.98 (minor isomer) (s, 3H), 2.04-2.18 (m, 2.6H), 2.25-2.32 (m, 0.4H), 3.80-3.88 (m, 2H), 3.92-4.00 (m, 2H), 4.83 (t, J=4.8 Hz, 1H).

(1SR,3SR)-1-(2-(1,3-dioxolan-2-yl)ethyl)-3-isopropylcyclopentyl acetate (major isomer)

$^{13}$C NMR (125 MHz, $CDCl_3$): δ 21.2, 21.4, 22.2, 28.9, 29.0, 31.9, 33.6, 37.7, 42.8, 46.3, 64.9, 91.5, 104.4, 170.4.

(1SR,3RS)-1-(2-(1,3-dioxolan-2-yl)ethyl)-3-isopropylcyclopentyl acetate (minor isomer)

$^{13}$C NMR (125 MHz, $CDCl_3$): δ 21.3, 21.4, 22.2, 29.1, 29.1, 31.9, 33.5, 37.5, 42.7, 45.7, 64.9, 92.2, 104.4, 170.4.

Step 3: Preparation of 2-(2-(4-isopropylcyclopent-1-en-1-yl)ethyl)-1,3-dioxolane/2-(2-(3-isopropylcyclopent-1-en-1-yl)ethyl)-1,3-dioxolane The compound was prepared according to the procedure reported for the preparation of 2-(2-(4-(tert-butyl)cyclohex-1-en-1-yl)ethyl)-1,3-dioxolane using, as a starting material, the compound prepared in the previous step.

GC crude: 42.9%/40.2% 2-(2-(4-isopropylcyclopent-1-en-1-yl)ethyl)-1,3-dioxolane/2-(2-(3-isopropylcyclopent-1-en-1-yl)ethyl)-1,3-dioxolane and 7.3% 2-(2-(3-isopropylcyclopentylidene)ethyl)-1,3-dioxolane from 1-(2-(1,3-dioxolan-2-yl)ethyl)-3-isopropylcyclopentyl acetate (57.4%/41.6% purity).

47.8%/47.6%/4.6% purity (GC) after purification.

2-(2-(4-isopropylcyclopent-1-en-1-yl)ethyl)-1,3-dioxolane/2-(2-(3-isopropylcyclopent-1-en-1-yl)ethyl)-1,3-dioxolane $^1$H-NMR (500.15 MHz): 0.83, 0.86, 0.87, 0.87 (d, 6H, J=6.7 Hz), 1.42-1.54 (m, 1.5H) 1.77-1.84 (m, 2H), 1.92-2.02 (m, 2H), 2.12-2.45 (m, 4.5H), 3.82-3.89 (m, 2H), 3.93-4.01 (m, 2H), 4.87 (t, J=4.8 Hz, 0.5H), 4.88 (t, J=4.8 Hz, 0.5H), 5.29-5.32 (m, 0.5H), 5.33-5.35 (m, 0.5H).

$^{13}$C NMR (125 MHz, $CDCl_3$): δ 20.3, 20.5, 20.9, 21.0, 25.7, 25.8, 27.8, 32.1, 32.3, 33.0, 33.6, 34.9, 36.9, 39.6, 46.2, 52.8, 64.9, 64.9, 104.3, 104.3, 123.0, 126.6, 143.2, 143.9.

Characteristic signal for 2-(2-(4-isopropylcyclopent-1-en-1-yl)ethyl)-1,3-dioxolane: $^{13}$C NMR (125 MHz, $CDCl_3$): 46.2 ppm Characteristic signal for 2-(2-(3-isopropylcyclopent-1-en-1-yl)ethyl)-1,3-dioxolane: $^{13}$C NMR (125 MHz, $CDCl_3$): 52.8 ppm Step 4: Preparation of 3-(4-isopropylcyclopent-1-en-1-yl)propanal/3-(3-isopropylcyclopent-1-en-1-yl) propanal The compound (1/1 mixture) was prepared according to procedure reported in Example 13 using, as a starting material, the compound prepared in the previous step.

$^1$H-NMR (500.15 MHz): 0.83, 0.86, 0.86, 0.87 (d, 6H, J=6.7 Hz), 1.43-1.54 (m, 1.5H) 1.94-2.03 (m, 2H), 2.18-2.45 (m, 4.5H), 2.54-2.60 (m, 2H), 5.28-5.31 (m, 0.5H), 5.32-5.34 (m, 0.5H), 9.75 (t, 0.5H, J=1.86 Hz), 9.77 (t, 0.5H, J=1.74 Hz).

3-(4-isopropylcyclopent-1-en-1-yl)propanal $^{13}$C NMR (150 MHz, $CDCl_3$): δ 20.9, 21.0, 23.9, 33.5, 36.9, 39.7, 41.8, 46.1, 124.0, 142.0, 202.6.

3-(3-isopropylcyclopent-1-en-1-yl)propanal $^{13}$C NMR (150 MHz, $CDCl_3$): δ 20.2, 20.5, 23.8, 27.7, 32.9, 35.0, 42.0, 52.8, 127.5, 142.7, 202.6.

Example 23

Hydroformylation of ((4,4-dimethyl-1-vinylcyclohexyl) oxy)trimethylsilane with BIPHEPHOS-Rh The autoclave was charged with (4,4-dimethyl-1-vinylcyclohexoxy)-trimethyl-silane (96%, 5.04 g, 22.26 mmol), $Rh(CO)_2acac$ (3.3 mg, 0.0128 mmol) and BiPhePhos (27.3 mg, 0.0347 mmol). The vessel was purged with $H_2$/CO (1:1, 4×5 bar) and heated under vigorous stirring at 90° C. and 10 bar syngas pressure for 24h. After cooling and depressurization, GLC analysis of the crude revealed total conversion and the presence of 3-(4,4-dimethyl-1-((trimethylsilyl)oxy) cyclohexyl) propanal (92.2%) and ((1-ethyl-4,4-dimethylcyclohexyl)oxy) trimethylsilane (6.8%).

3-(4,4-dimethyl-1-((trimethylsilyl)oxy)cyclohexyl) propanal:

$^1$H-NMR (600.15 MHz): δ 0.12 (s, 9H, $Si(CH_3)_3$), 0.88, 0.93 (2×s, 6H, $C(CH_3)_2$), 1.15-1.22 (m, 2H), 1.36-1.49 (m, 4H), 1.55-1.62 (m, 2H), 1.82 (t, J=7.6 Hz, 2H, H-3'), 2.48 (t, J=7.27 Hz, $J_{H-H}$=1.69 Hz, 2H, H-2'), 9.67 (t, 1H, $^2J_{1,2}$=1.60 Hz).

$^{13}$C NMR (125 MHz, $CDCl_3$): δ 2.6 (q), 28.4 (q), 29.6 (s), 32.3 (t), 34.2 (t), 35.7 (t), 38.7 (t), 74.9 (s), 203.0 (d).

Example 24

Acid/Lewis Acid Screening for the Transformation of Dioxolane Acetates to Unsaturated Dioxolanes For the acid/lewis acid screening the substrate (1-(2-(1,3-dioxolan-2-yl)ethyl)-4,4-dimethylcyclohexyl acetate, 216 mg, 0.8 mmol) was heated in a sealed glass vial in the presence of the catalyst (acid, lewis acid) in 1 mL dry toluene (1h at RT, 1h at 50° C., 1h at 120° C., 2h at 120° C.). The conversion of the starting material to the desired products ((2-(2-(4,4-dimethylcyclohex-1-en-1-yl)ethyl)-1,3-dioxolane, 3-(4,4-dimethylcyclohex-1-en-1-yl)propanal (minor product)) was determined by GC analysis.

The results obtained are shown in Table 11.

TABLE 11

Screening of acids/lewis acids for the transformation of 1-(2-(1,3-dioxolan-2-yl)ethyl)-4,4-dimethylcyclohexyl acetate to (2-(2-(4,4-dimethylcyclohex-1-en-1-yl)ethyl)-1,3-dioxolane

| Entry | acid (LA) | quantity | Temperature/ time | Conversion of acetate | ratio endo/exo[1)] |
|---|---|---|---|---|---|
| 1 | MsOH | 10 mol % | RT (1 h)<br>50° C. (1 h)<br>120° C. (1 h) | 100% | 96.9/3.1 |
| 2 | $H_2SO_4$ | 2 mol % | RT (1 h)<br>50° (1 h)<br>120° C. (1 h) | 100% | 97.9/2.1 |
| 3 | oxalic acid | 14 mol % | RT (1 h)<br>50° (1 h)<br>120° C. (3 h) | 51.8% | 87.5/12.5 |
| 4 | $BF_3 \cdot Et_2O$ | 22 mol % | RT (1 h)<br>50° (1 h) | 100% | 98.7/1.3 |
| 5 | $H_3PO_4$ (85%) | 4.5 mol % | RT (1 h)<br>50° (1 h)<br>120° C. (1 h) | 100% | 93.9/6.1 |
| 6 | pTsOH $H_2O$ | 5 mol % | RT (1 h)<br>50° (1 h)<br>120° C. (1 h) | 100% | 98.0/2.0 |
| 7 | $KHSO_4$ | 10 mol % | RT (1 h)<br>50° (1 h)<br>120° C. (3 h) | 51.1% | 85.5/14.5 |
| 8 | CSA | 5 mol % | RT (1 h)<br>50° (1 h)<br>120° C. (3 h) | 98.6% | 96.5/3.5 |
| 9 | PPTS | 10 mol % | RT (1 h)<br>50° (1 h)<br>120° C. (3 h) | 63.7% | 93.6/6.4 |
| 10 | $BF_3 \cdot Et_2O$ | 11 mol % | RT (1 h)<br>50° (1 h) | 99.7% | 95.6/4.4 |
| 11 | $BF_3 \cdot Et_2O$ | 21 mol % | RT (1 h) | 99.8% | 97.2/2.8 |
| 12 | $ZnBr_2$ | 10 mol % | RT (1 h)<br>50° (1 h)<br>120° C. (1 h) | 100% | 94.8/5.2 |
| 13 | Clariant K10-S300 | 10 weight % | RT (1 h)<br>50° (1 h)<br>120° C. (1 h) | 100% | 90.5/9.5 |

TABLE 11-continued

Screening of acids/lewis acids for the transformation of 1-(2-(1,3-dioxolan-2-yl)ethyl)-4,4-dimethylcyclohexyl acetate to (2-(2-(4,4-dimethylcyclohex-1-en-1-yl)ethyl)-1,3-dioxolane

| Entry | acid (LA) | quantity | Temperature/ time | Conversion of acetate | ratio endo/exo[1)] |
|---|---|---|---|---|---|
| 14 | CBV 21A Zeolite | 10 weight % | RT (1 h)<br>50° (1 h)<br>120° C. (1 h) | 45.3% | 82.4/17.6 |
| 15 | CBV 780 Zeolite | 10 weight % | RT (1 h)<br>50° (1 h)<br>120° C. (1 h) | 100% | 95.1/4.9 |
| 16 | CP814E Zeolite | 10 weight % | RT (1 h)<br>50° (1 h)<br>120° C. (1 h) | 99.8% | 87.0/13.0 |
| 17 | Siral ® 40 HPV | 10 weight % | RT (1 h)<br>50° (1 h)<br>120° C. (3 h) | 83.8% | 85.7/14.3 |
| 18 | F24 X Bentonite | 10 weight % | RT (1 h)<br>50° (1 h)<br>120° C. (1 h) | 100% | 92.8/7.2 |

[1)]Ratio endo/exo (2-(2-(4,4-dimethylcyclohex-1-en-1-yl)ethyl)-1,3-dioxolane (endo)/2-(2-(4,4-dimethylcyclohexylidene)ethyl)-1,3-dioxolane (exo)

The invention claimed is:

1. A process for the preparation of a compound of formula (I):

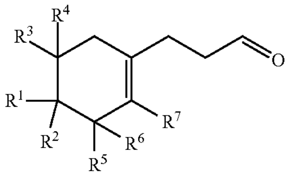

(I)

in the form of any one of its stereoisomers or a mixture thereof, and wherein each $R^1$, $R^2$, $R^3$, $R^4$, $R^5$, $R^6$ and $R^7$, independently from each other, is selected from the group consisting of a hydrogen atom, a $C_{1-6}$ alkyl group and a $C_{2-6}$ alkenyl group, each optionally substituted by a hydroxy or a $C_{1-3}$ alkoxy group; or two groups among $R^1$, $R^2$, $R^3$, $R^4$, $R^5$, $R^6$ and $R^7$ are taken together and form a $C_{3-8}$ cycloalkyl or a $C_{5-8}$ cycloalkenyl group;

comprising a hydroformylation and an elimination step starting from a compound of formula (II):

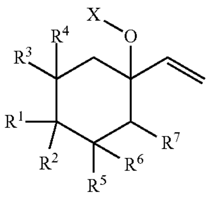

(II)

in the form of any one of its stereoisomers or a mixture thereof, and wherein $R^1$, $R^2$, $R^3$, $R^4$, $R^5$, $R^6$ and $R^7$ have the same meaning as defined in formula (I) and X represents a C (O) R group or a $Si(R')_3$ group wherein R is selected from the group consisting of a hydrogen atom, a $C_{1-4}$ alkyl group, a $C_{1-4}$ alkoxy group or a phenyl group, and each R', independently from each other, is a $C_{1-4}$ alkyl group wherein the process comprises a) hydroformylation of the compound of formula (II) to obtain a compound of formula (III):

(III)

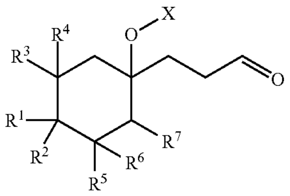

in the form of any one of its stereoisomers or a mixture thereof, and wherein X, $R^1$, $R^2$, $R^3$, $R^4$, $R^5$, $R^6$ and $R^7$ have the same meaning as defined for formula (I);

b) protection of the aldehyde group of the compound of formula (III) obtained in step a) in the form of an acetal of formula (IV):

(IV)

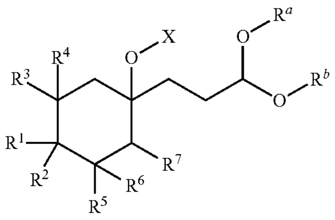

in the form of any one of its stereoisomers or a mixture thereof, and wherein X, $R^1$, $R^2$, $R^3$, $R^4$, $R^5$, $R^6$ and $R^7$ have the same meaning as defined for formula (I) and each $R^a$ and $R^b$, independently from each other, represents a $C_{1-4}$ alkyl group or $R^a$ and $R^b$ are taken together and represent a $C_{2-6}$ alkanediyl group;

c) elimination of the OX group of the compound of formula (IV) followed by an isomerization to form a compound of formula (V):

(V)

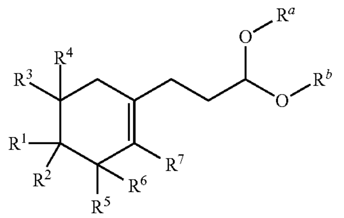

in the form of any one of its stereoisomers or a mixture thereof, and wherein $R^1$, $R^2$, $R^3$, $R^4$, $R^5$, $R^6$ and $R^7$ have the same meaning as defined for formula (I) and $R^a$ and $R^b$ have the same meaning as defined in step b); and d) deprotection of the acetal group to obtain the compound of formula (I).

2. The process according to claim 1, wherein each $R^3$, $R^4$, $R^5$, $R^6$ and $R^7$, independently from each other, is selected from the group consisting of a hydrogen atom and a $C_{1-3}$ alkyl group.

3. The process according to claim 1, wherein the compound of formula (I) is of formula (I');

(I')

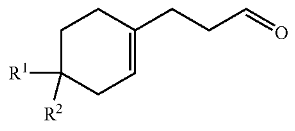

in the form of any one of its stereoisomers or a mixture thereof, and wherein $R^1$ and $R^2$ have the same meaning as defined in claim 1;

and said compound of formula (II) is of formula (II'):

(II')

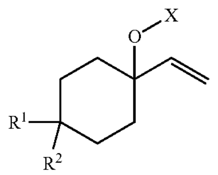

in the form of any one of its stereoisomers or a mixture thereof, and wherein X, $R^1$ and $R^2$ have the same meaning as defined in claim 1.

4. The process according to claim 1, wherein $R^1$ is a $C_{1-4}$ alkyl group or a $C_{2-4}$ alkenyl group.

5. The process according to claim 1, wherein $R^1$ is a methyl group.

6. The process according to claim 1, wherein $R^2$ is selected from the group consisting of a hydrogen atom, a $C_{1-3}$ alkyl group and a $C_{2-3}$ alkenyl group.

7. The process according to claim 1, wherein $R^2$ is a methyl group.

8. The process according to claim 1, wherein the hydroformylation is performed in the presence of a rhodium catalyst.

9. The process according to claim 1, wherein the preparation of the compound of formula (II):

(II)

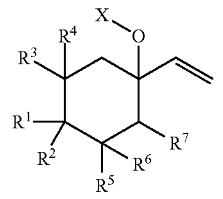

in the form of any one of its stereoisomers or a mixture thereof, and wherein X represents a C(O)R group or a $Si(R')_3$ group wherein R is a hydrogen atom, a $C_{1-4}$ alkyl group, a $C_{1-4}$ alkoxy group or a phenyl group, and each R', independently from each other, is a $C_{1-4}$ alkyl group; each $R^1$, $R^2$, $R^3$, $R^4$, $R^5$, $R^6$ and $R^7$, independently from each other, represents a hydrogen atom, a $C_{1-6}$ alkyl group or a $C_{2-6}$ alkenyl group, each optionally substituted by a hydroxy or $C_{1-3}$ alkoxy group; or two groups among $R^1$, $R^2$, $R^3$, $R^4$, $R^5$, $R^6$ and $R^7$ are taken together and form $C_{3-8}$ cycloalkyl or $C_{5-8}$ cycloalkenyl group;

comprising the step of reducing a compound of formula (VII):

(VII)

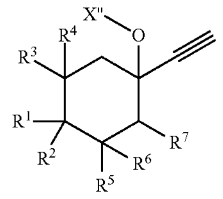

in the form of any one of its stereoisomers or a mixture thereof, wherein X" is a hydrogen atom, a C(O)R group or a $Si(R')_3$ group wherein R is a hydrogen atom, a $C_{1-4}$ alkyl group, a $C_{1-4}$ alkoxy group or a phenyl group, and each R', independently from each other, is a $C_{1-4}$ alkyl group; and wherein $R^1$, $R^2$, $R^3$, $R^4$, $R^5$, $R^6$ and $R^7$ have the same meaning as in claim 1.

10. The process according to claim 1, wherein $R^1$ is a $C_{1-4}$ alkyl group or a $C_{2-4}$ alkenyl group and $R^2$ is selected from the group consisting of a hydrogen atom, a $C_{1-3}$ alkyl group and a $C_{2-3}$ alkenyl group.

11. The process according to claim 1, wherein $R^1$ is a methyl group and $R^2$ is a methyl group.

12. The process according to claim 3, wherein $R^1$ is a $C_{1-4}$ alkyl group or a $C_{2-4}$ alkenyl group and $R^2$ is selected from the group consisting of a hydrogen atom, a $C_{1-3}$ alkyl group and a $C_{2-3}$ alkenyl group.

13. The process according to claim 3, wherein $R^1$ is a methyl group and $R^2$ is a methyl group.

14. The process according to claim 8, wherein $R^a$ and $R^b$ are taken together and represent a $(CH_2)_n$ group wherein n is 2 or 3.

* * * * *